(12) United States Patent
Prabhakaran

(10) Patent No.: US 8,835,602 B2
(45) Date of Patent: *Sep. 16, 2014

(54) TEMPLATES FOR NUCLEATION AND PROPAGATION OF PEPTIDE SECONDARY STRUCTURE

(75) Inventor: Erode N. Prabhakaran, Bangalore (IN)

(73) Assignee: Indian Institute of Science, Bangalore (IN)

( * ) Notice: Subject to any disclaimer, the term of this patent is extended or adjusted under 35 U.S.C. 154(b) by 690 days.

This patent is subject to a terminal disclaimer.

(21) Appl. No.: 12/550,977

(22) Filed: Aug. 31, 2009

(65) Prior Publication Data

US 2010/0228004 A1 Sep. 9, 2010

(30) Foreign Application Priority Data

Mar. 6, 2009 (IN) .............................. 505/CHE/2009

(51) Int. Cl.
C07K 5/00 (2006.01)
C07K 5/083 (2006.01)
C07K 5/062 (2006.01)

(52) U.S. Cl.
CPC ........... *C07K 5/0806* (2013.01); *C07K 5/06026* (2013.01)
USPC ........................................... 530/314; 514/34

(58) Field of Classification Search
CPC .... C07K 14/001; C07K 1/107; C07K 5/0812; C07K 5/06026; C07K 5/0806
See application file for complete search history.

(56) References Cited

U.S. PATENT DOCUMENTS 4,703,034 A 10/1987 Freidinger et al.
7,202,332 B2 4/2007 Arora et al.
2006/0258646 A1* 11/2006 Biftu et al. .................... 514/221

FOREIGN PATENT DOCUMENTS

WO WO/2007/142381 12/2007

OTHER PUBLICATIONS

Davies et. al., Cyclization of Peptides and Depsipeptides. J. Peptide Sci. 9: 471-501, 2003.*
Wen and Spatola, Synthesis of a cyclic pseudopeptide containing a flexible Beta-Ala_[CH2NH] unit, Department of Chemistry, Pharmacopeia Drug, Tetrahedron Letters (2005), 46(14), 2499-2501).*
Bughin et. al. (5-Aminaooxazole as an Internal Traceless Activator of C-Terminal Carboxylic Acid: Rapid Access to Diversely Functionalized Cyclodepsipeptides, Chemistry Eur.(2006), 12, 1174-1184).*
Ankersen, M. et al., "Discovery of a Novel Non-Peptide Somatostatin Agonist with SST$_4$ Selectivity," *J. Am. Chem. Soc.*, vol. 120, 1998, pp. 1368-1373.

Bass, M. B. et al., "A Method for Determining the Positions of Polar Hydrogens Added to a Protein Structure That Maximizes Protein Hydrogen Bonding," *Proteins: Structure, Function, and Genetics*, vol. 12, 1992, pp. 266-277.
Baumeister, R. et al., "Contacts between Tet Repressor and *tet* Operator Revealed by New Recognition Specificities of Single Amino Acid Replacement Mutants," *J. Mol. Biol.*, vol. 226, 1992, pp. 1257-1270.
Bigott-Hennkens, H. et al., "Synthesis and in Vitro Evaluation of a Rhenium-Cyclized Somatostatin Derivative Series," *J. Med. Chem.*, vol. 51, 2008, pp. 1223-1230.
Bisang, C. et al., "Synthesis, Conformational Properties, and Immunogenicity of a Cyclic Template-Bound Peptide Mimetic Containing an NPNA Motif from the Circumsporozoite Protein of *Plasmodium falciparum*," *J. Am. Chem. Soc.*, vol. 120, 1998, pp. 7439-7449.
Brickmann, K. et al., "Synthesis of Conformationally Restricted Mimetics of γ-Turns and Incorporation into Desmopressin, an Analogue of the Peptide Hormone Vasopressin," *Chem. Eur. J.*, vol. 5, No. 8, 1999, pp. 2241-2253.
Chapman, R. N. et al., "A Highly Stable Short α-Helix Constrained by a Main-Chain Hydrogen-Bond Surrogate," *J. Am. Chem. Soc.*, vol. 126, 2004, pp. 12252-12253.
Chen, F. W. et al., "Ribosomal Proteins in Cell Proliferation and Apoptosis," *Intern. Rev. Immunol.*, vol. 18, 1999, pp. 429-448.
Classen, J. et al., "Gramicidin-Induced Enhancement of Transbilayer Reorientation of Lipids in the Erythrocyte Membrane," *Biochemistry*, vol. 26, 1987, pp. 6604-6612.
Cluzeau, J. et al., "Design and synthesis of all diastereomers of cyclic pseudo-dipeptides as mimics of cyclic CXCR4 pentapeptide antagonists," *Org. Biomol. Chem.*, vol. 5, 2007, pp. 1915-1923.
Coin, I. et al., "Solid-phase peptide synthesis: from standard procedures to the synthesis of difficult sequences," *Nature Protocols*, vol. 2, No. 12, 2007, pp. 3247-3256.
Collins, J. M. et al., "Microwave-enhanced Solid-phase Peptide Synthesis," *Microwaves in Organic Synthesis* 2$^{nd}$ Edition, 2006, pp. 898-930.
Cudic, P. et al., "Pseudopeptide Synthesis via Fmoc Solid-Phase Synthetic Methodology," *Mini-Reviews in Organic Chemistry*, vol. 4, 2007, pp. 268-280.
Desjarlais, J. R. et al., "Redesigning the DNA-Binding Specificity of a Zinc Finger Protein : A Data Base-Guided Approach," *Proteins: Structure, Function, and Genetics*, vol. 12, 1992, pp. 101-104.

(Continued)

Primary Examiner — James H Alstrum Acevedo
Assistant Examiner — Jeanette Lieb
(74) Attorney, Agent, or Firm — Foley & Lardner LLP

(57) ABSTRACT

Compounds having the Formula I and pharmaceutically acceptable salts thereof are provided in which the variables are described herein.

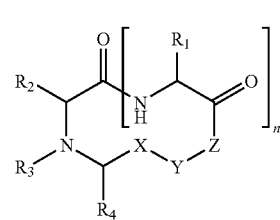

Methods of making the compounds of Formula I are also disclosed.

20 Claims, 2 Drawing Sheets

(56) References Cited

OTHER PUBLICATIONS

Du, Y. et al., "The synthesis and evaluation of 10- and 12-membered ring benzofused enediyne amino acids," *Bioorganic and Medicinal Chemistry*, vol. 13, 2005, pp. 5936-5948.

Durai, S. et al., "Zinc finger nucleases: custom-designed molecular scissors for genome engineering of plant and mammalian cells," *Nucleic Acids Research*, vol. 33, No. 18, 2005, pp. 5978-5990.

Evans, P. et al., "Synthesis of a 6-aryloxymethyl-5-hydroxy-2,3,4,5-tetrahydro-[1H]-2-benzazepin-4-one: a muscarinic ($M_3$) antagonist," *Org. Biomol. Chem.*, vol. 6, 2008, pp. 2158-2167.

Fu, H. et al., "A Bactericidal Cecropin-A Peptide with a Stabilized α-Helical Structure Possess an Increased Killing Capacity But No Proinflammatory Activity," *Inflammation*, vol. 28, No. 6, Dec. 2004, pp. 337-343

Fukuyama, T. et al., "2,4-Dinitrobenzenesulfonamides: A Simple and Practical Method for the Preparation of a Variety of Secondary Amines and Diamines," *Tetrahedron Letters*, vol. 38, No. 33, 1997, pp. 5831-5834.

Galloux, M. et al., "Infectious Bursal Disease Virus, a Non-enveloped Virus, Possesses a Capsid-associated Peptide That Deforms and Perforates Biological Membranes," *Journal of Biological Chemistry*, vol. 282, No. 28, Jul. 13, 2007, pp. 20774-20784.

Gilon, C. et al., "A Backbone-Cyclic, Receptor 5-Selective Somatostatin Analogue: Synthesis, Bioactivity, and Nuclear Magnetic Resonance Conformational Analysis," *J. Med. Chem.*, vol. 41, 1998, pp. 919-929.

Graminski, G. et al., "A Rapid Bioassay for Platelet-Derived Growth Factor β-Receptor Tyrosine Kinase Function," *Biotechnology*, vol. 12, 1994, pp. 1008-1011.

Hadley, M., "Discovery that a melanocortin regulates sexual functions in male and female humans," *Peptides*, vol. 26, 2005, pp. 1687-1689.

He, Y. et al., "Probing *met* repressor—operator recognition in solution," *Nature*, vol. 359, Oct. 1, 1992, pp. 431-433.

Hemmerich, P. et al., "Human ribosomal protein L7 binds RNA with a α-helical arginine-rich and lysine-rich domain," *Eur. J. Biochem.*, vol. 245, 1997, pp. 549-556.

Hocart, S. et al., "Potent Antagonists of Somatostatin: Synthesis and Biology," *J. Med. Chem.*, vol. 41, 1998, pp. 1146-1154.

Hojo, K. et al., "Development of a Method for the Solid-Phase Peptide Synthesis in Water," *Int. J. Pept. Res. Ther.*, vol. 14, 2008, pp. 373-380.

Jamieson, A. C. et al., "A zinc finger directory for high-affinity DNA recognition," *Proc. Natl. Acad. Sci.*, vol. 93, Nov. 1996, pp. 12834-12839.

Jelokhani-Niaraki, M. et al., "Interaction of Gramicidin S and its Aromatic Amino-Acid Analog with Phospholipid Membranes," *Biophysical Journal*, vol. 95, Oct. 2008, pp. 3306-3321.

Jerić, I. et al., "A synthetic route to enediyne-bridged amino acids," *Tetrahedron Letters*, vol. 48, 2007, pp. 4687-4690.

Kim, C. A. et al., "Serine at Position 2 in the DNA Recognition Helix of a $Cys_2$-$His_2$ Zinc Finger Peptide is Not, in General, Responsible for Base Recognition," *J. Mol. Biol.*, vol. 252, 1995, pp. 1-5.

Klee, M. et al., "Bcl-$X_L$ specifically activates Bak to induce swelling and restructuring of the endoplasmic reticulum," *Journal of Cell Biology*, vol. 168, No. 5, Feb. 28, 2005, pp. 723-734.

Koppan, M. et al., "Targeted Cytotoxic Analogue of Somatostatin AN-238 Inhibits Growth of Androgen-independent Dunning R-3327-AT-1 Prostate Cancer in Rats at Nontoxic Doses," *Cancer Research*, vol. 58, Sep. 15, 1998, pp. 4132-4137.

Lam, K. et al., "A new type of synthetic peptide library for identifying ligand-binding activity," *Nature*, vol. 354, Nov. 7, 1991, pp. 82-84.

Liu, S. et al., "Nonpeptide Somatostatin Agonists with $sst_4$ Selectivity: Synthesis and Structure—Activity Relationships of Thioureas," *J. Med. Chem.*, vol. 41, 1998, pp. 4693-4705.

Mattern, R. et al., "Conformational Analyses of Somatostatin-Related Cyclic Hexapeptides Containing Peptoid Residues," *J. Med. Chem.*, vol. 41, 1998, pp. 2686-2692.

McKennon, M. et al., "A Convenient Reduction of Amino Acids and Their Derivatives," *J. Org. Chem.*, vol. 58, 1993, pp. 3568-3571.

Mercier, C. et al., "The amphipathic alpha helices of the Toxoplasma protein GRA2 mediate post-secretory membrane association," *Journal of Cell Science*, vol. 111, 1998, pp. 2171-2180.

Mikecz, A. et al., "Human Ribosomal Protein L7 Carries Two Nucleic Acid-Binding Domains with Distinct Specificities," *Biochemical and Biophysical Research Communications*, vol. 258, 1999, pp. 530-536.

Minin, P. L. et al., "Radical Ring Closures of 4-Isocyanato Carbon-Centered Radicals," *J. Org. Chem.*, vol. 68, 2003, pp. 2960-2963.

Moore, S. B. at al., "Discovery of Iodinated Somatostatin Analogues Selective for hsst2 and hsst5 with Excellent Inhibition of Growth Hormone and Prolactin Release from Rat Pituitary Cells," *J. Med. Chem.*, vol. 48, 2005, pp. 6643-6652.

Moya, E. at al., "Total Syntheses of Polyamine Amides PhTX-4.3.3 and PhTX-3.4.3: Reductive Alkylation is a Rapid, Practical Route to Philanthotoxins," *Tetrahedron Letters*, vol. 36, No. 51, 1995, pp. 9401-9404.

Mujeeb, A. et al., "NMR structure of a biologically active peptide containing the RNA-binding domain of human immunodeficiency virus type 1 Tat," *Proc. Natl. Acad. Sci.*, vol. 91, Aug. 1994, pp. 8248-8252.

Murray, P. J. et al., "A Novel Series of Arylpiperazines with High Affinity and Selectivity for the Dopamine $D_3$ Receptor," *Bioorganic & Medicinal Chemistry Letters*, vol. 5, No. 3, 1995, pp. 219-222.

Nagy, A. et al., "Synthesis and biological evaluation of cytotoxic analogs of somatostatin containing doxorubicin or its intensely potent derivative, 2-pyrrolinodoxorubicin," *Proc. Natl. Acad. Sci.*, vol. 95, Feb. 1998, pp. 1794-1799.

Olsen, C. A. et al., "Aminolysis of Resin-Bound N-Nosylaziridine-2-carboxylic Acids," *Organic Letters*, vol. 8, No. 15, 2006, pp. 3371-3374.

Pabo, C. O. et al., "Protein-DNA Recognition," *Ann. Rev. Biochem.*, vol. 53, 1984, pp. 293-321.

Patino, N. et al., "Modelling, synthesis and biological evaluation of an ethidium—arginine conjugate linked to a ribonuclease mimic directed against TAR RNA of HIV-1," *Eur. J. Med. Chem.*, vol. 37, 2002, pp. 573-584.

Penso, M. et al., "Chemoselective N-Alkylation of Di-N,O-protected Tyrosine through Specific Oxy-Anion Solvation by Non-Hydrogen Bonding Donor Solvents," *Synlett*, vol. 5, 2006, pp. 0741-0744.

Pérez-Payá, E. at al., "The Role of Amphipathicity in the Folding, Self-association and Biological Activity of Multiple Subunit Small Proteins," *Journal of Biological Chemistry*, vol. 270, No. 3, Jan. 20, 1995, pp. 1048-1056.

Piró, J. et al., "Solid phase synthesis of enantiomerically pure polyhydroxyvalerolactams," *Tetrahedron Letters*, vol. 42, 2001, pp. 871-873.

Pouliquin, P. et al., "Effects of an α-helical ryanodine receceptor C-terminal tail peptide on ryanodine receptor activity: Modulation by Homer," *International Journal of Biochemistry & Cell Biology*, vol. 38, 2006, pp. 1700-1715.

Resende, J. M. et al., "Solution NMR structures of the antimicrobial peptides phylloseptin-1, -2, and -3 and biological activity: The role of charges and hydrogen bonding interactions in stabilizing helix conformations," *Peptides*, vol. 29, 2008, pp. 1633-1644.

Rivier, J. et al., "Minimal-Size, Constrained Corticotropin-Releasing Factor Agonists with i-(i+3) Glu-Lys and Lys-Glu Bridges," *J. Med. Chem.*, vol. 41, 1998, pp. 2614-2620.

Sabatino, G. et al., "Advances in automatic, manual and microwave-assisted solid-phase peptide synthesis," *Current Opinion Drug Discovery & Development*, vol. 11, No. 6, 2008, pp. 762-770.

Saruta, K. et al., "A traceless solid phase synthesis of thiomorpholin-3-ones," *Tetrahedron Letters*, vol. 49, 2008, pp. 424-427.

Sattler, M. et al., "Structure of Bcl-$x_L$-Bak Peptide Complex: Recognition Between Regulators of Apoptosis," *Science*, vol. 275, Feb. 14, 1997, pp. 983-986.

Singh, Y. et al., "Structural Mimicry of Two Cytochrome $b_{562}$ Interhelical Loops Using Macrocycles Constrained by Oxazoles and Thiazoles," *J. Am. Chem. Soc.*, vol. 127, 2005, pp. 6563-6572.

Sohma, Y. et al., "Development of O-Acyl Isopeptide Method," *Peptide Science*, vol. 88, No. 2, 2007, pp. 253-262.

(56) References Cited

OTHER PUBLICATIONS

Somers, W. S. et al., "The Met Repressor-Operator Complex: DNA Recognition by α-Strands[a]," *Annals of the New York Academy of Sciences*, vol. 726, 1994, pp. 105-117.

Somers, W. S. et al., "Crystal structure of the *met* repressor—operator complex at 2.8 Å resolution reveals DNA recognition by α-strands," *Nature*, vol. 359, Oct. 1, 1992, pp. 387-393.

Sørensen, M. D. et al., "Cyclic Phosphinamides and Phosphonamides, Novel Series of Potent Matric Metalloproteinase Inhibitors with Antitumour Activity," *Bioorganic & Medicinal Chemistry*, vol. 11, 2003, pp. 5461-5484.

Tamaki, M. et al., "A Novel, Antimicrobially Active Analog of Gramicidin S without Amphiphilic Conformation," *J. Antibiot.*, vol. 59, No. 6, 2006, pp. 370-372.

Timofeeva, O. A. et al., "Rationally Designed Inhibitors Identify STAT3 N-Domain as a Promising Anticancer Drug," *ACS Chemical Biology*, vol. 2, No. 12, 2007, pp. 799-809.

Tran, T. et al., "Design, Synthesis, and Biological Activities of Potent and Selective Somatostatin Analogues Incorporating Novel Peptoid Residues," *J. Med. Chem.*, vol. 41, 1998, pp. 2679-2685.

Turner, J. J. et al., "Synthesis of novel amino acid carbohydrate hybrids via Mitsunobu glycosylation of nitrobenzenesulfonamides," *Tetrahedron Letters*, vol. 42, 2001, pp. 5763-5767.

Van Horn, B. A. et al., "Toward Cross-Linked Degradable Polyester Materials: Investigations into the Compatibility and Use of Reductive Amination Chemistry for Cross-Linking," *Macromolecules*, vol. 40, 2007, pp. 1480-1488.

Walensky, L. D. et al., "Activation of Apoptosis in Vivo by a Hydrocarbon-Stapled BH3 Helix," *Science*, vol. 305, Sep. 3, 2004, pp. 1466-1470.

Wang, D. et al., "Enhanced Metabolic Stability and Protein-Binding Properties of Artificial α Helices Derived from a Hydrogen-Bond Surrogate: Application to Bcl-xL," *Angew. Chem. Int. Ed.*, vol. 44, 2005, pp. 6525-6529.

Wang, M. et al., "Evaluation of Enantiopure *N*-(Ferrocenylmethyl)azetidin-2-yl(diphenyl)methanol for Catalytic Asymmetric Addition of Organozinc Reagents to Aldehydes," *J. Org. Chem.*, vol. 73, 2008, pp. 168-176.

Williams, G. D. et al., "A One-Pot Process for the Enantioselective Synthesis of Amines via Reductive Amination under Transfer Hydrogenation Conditions," *Organic Letters*, vol. 5, No. 22, 2003, pp. 4227-4230.

Wohlrab, A. et al., "Total Synthesis of Plusbacin $A_3$: A Depsipeptide Antibiotic Active Against Vancomycin-Resistant Bacteria," *J. Am. Chem. Soc.*, vol. 129, 2007, pp. 4175-4177.

Yang, L. et al., "Spiro[1*H*-indene-1,4'-piperidine] Derivatives As Potent and Selective Non-Peptide Human Somatostatin Receptor Subtype 2 ($sst_2$) Agonists," *Journal of Medicinal Chemistry*, vol. 41, No. 13, Jun. 18, 1998, pp. 2175-2179.

Yang, L. et al., "Synthesis and biological activities of potent peptidomimetics selective for somatostatin receptor subtype 2," *Proc. Natl. Acad. Sci.*, vol. 95, Sep. 1998, pp. 10836-10841.

Ying, J. et al., "Design, Synthesis, and Biological Evaluation of New Cyclic Melanotropin Peptide Analogues Selective for the Human Melanocortin-4 Receptor," *J. Med. Chem.*, vol. 49, 2006, pp. 6888-6896.

Zapf, C. W. et al., "Utilizing the intramolecular Fukuyama—Mitsunobu reaction for a flexible synthesis of novel heterocyclic scaffolds for peptidomimetic drug design," *Bioorganic and Medicinal Chemistry Letters*, vol. 15, 2005, pp. 4033-4036.

Zheleva, D. I. et al., "The p53-Mdm2 Pathway: Targets for the Development of New Anticancer Therapeutics," *Mini Reviews in Medicinal Chemistry*, vol. 3, 2003, pp. 257-270.

Rajagopal, S, et al., et al., "Catalytic Transfer Hydrogenation and Hydrogenolysis by Formic Acid and its Salts," Peptides Design, Synthesis and Biological Activity, Peptide synthesis and methodology, 1994, Ch.1, pp. 11-77.

Elmore, D.T., Amino Acids, Peptides, and Proteins, 2007, vol. 36, pp. 82-130.

Garcia, J., et al., "Stabilization of the biologically active conformation of the principal neutralizing determinant of HIV-1(IIIB) containing a cis-proline surrogate: 1H NMR and molecular modeling study," *Biochemistry*, 2006, vol. 45, Issue: 13, pp. 4284-4294.

Basséne, C. E. et al., "Studies towards the conception of new selective PPARβ/δ ligands," Bioorganic and Medicinal Chemistry Letters, 16:4528-4532 (2006).

Bisseger, P. et al., "Solid-phase synthesis of cyclic polyamines," Tetrahedron, 64(32):7531-7536 (2008).

Bouffard, J. et al., "A Highly Selective Fluorescent Probe for Thiol Bioimaging," Organic Letters, 10(1):37-40 (2008).

Buil, M. et al., "Preparation of Half-Sandwich Alkyl-Titanium(IV) Complexes Stabilized by a Cyclopentadienyl Ligand with a Pendant Phosphine Tether and Their Use in the Catalytic Hydroamination of Aliphatic and Aromatic Alkynes," Organometallics, 25(17):4079-4089 (2006).

But, T. et al., "The Mitsunobu Reaction: Origin, Mechanism, Improvements, and Applications," Chemistry—An Asian Journal, 2:1340-1355 (2007).

Chae, J. et al., "Palladium-Catalyzed Regioselective Hydrodebromination of Dibromoindoles: Application to the Enantioselective Synthesis of Indolodioxane U86192A," Journal of Organic Chemistry, 69(10):3336-3339 (2004).

Ferrer, C. et al., "Intra- and Intermolecular Reactions of Indoles with Alkynes Catalyzed by Gold," Chemistry—A European Journal, 13(5):1358-1373 (2007).

Fukumoto, Y. et al., "Anti-Markovnikov Addition of Both Primary and Secondary Amines to Terminal Alkynes Catalyzed by the $TpRh(C_2H_4)_2/PPh_3$ System," Journal of the American Chemical Society, 129(45):13792-13793 (2007).

Gardner, R. A. et al., "Total Synthesis of Petrobactin and Its Homologues as Potential Growth Stimuli for *Marinobacter hydrocarbonoclasticus*, an Oil-Degrading Bacteria," Journal of Organic Chemistry, 69(10):3530-3537 (2004).

Grigg, R. et al., "Kinetic acidity of iminium ions. 2-Alkynyl- and 2,5-dialkynyl-pyrrolidines via the iminium ion route to azomethine ylides," Tetrahedron, 58:2627-2640 (2002).

Guisado, C. et al., "The facile preparation of primary and secondary amines via an improved Fukuyama—Mitsunobu procedure. Application to the synthesis of a lung-targeted gene delivery agent," Organic and Biomolecular Chemistry, 3:1049-1057 (2005).

Kan, T. et al., "Ns strategies: a highly versatile synthetic method for amines," Chemical Communications, 353-359 (2004).

Kolomiets, E. et al., "Structure and Properties of Supramolecular Polymers Generated from Heterocomplementary Monomers Linked through Sextuple Hydrogen-Bonding Arrays," Macromolecules, 39:1173-1181 (2006).

Lambers, M. et al., "Highly Selective Hydroformylation of the Cinchona Alkaloids," Journal of Organic Chemistry, 67(14):5022-5024 (2002).

Le Bourdonnec, B., et al., "Discovery of a series of aminopiperidines as novel iNOS inhibitors," Bioorganic and Medicinal Chemistry Letters, vol. 18, Issue 1, pp. 336-343 (2008).

Lehmler, H. et al., "Synthesis and structure of environmentally relevant perfluorinated sulfonamides," Journal of Fluorine Chemistry, 128:595-607 (2007).

Lehmler, H. et al., "Synthesis and structure of environmentally relevant perfluorinated sulfonamides," Journal of Fluorine Chemistry, Author manuscript, Jun. 2008, published in final edited form as J Fluor Chem. Jun. 2007; 128 (6): 595-607, 26 pages.

Leigh, D. et al., "An ammonium/bis-ammonium switchblade molecular shuttle," Tetrahedron, 64(36):8411-8416 (2008).

Lin, X. et al., "Utilization of Fukuyama's sulfonamide protecting group for the synthesis of N-substituted 061-amino acids and derivatives," Tetrahedron Letters, 41:3309-3313 (2000).

Matsumoto, S., et. al., "Novel Synthesis of α-Amino Carboxamides and Their Related Compounds via α-Oxo Sulfones Starting from 2,2 Disulfonyloxiranes," Bulletin of The Chemical Society of Japan, vol. 77, Issue 10, pp. 1897-1903 (2004).

Non Final Office Action mailed May 23, 2012 in U.S. Appl. No. 12/551,101 (9 pages).

Non Final Office Action mailed Nov. 23, 2011 in U.S. Appl. No. 12/551,101 (6 pages).

(56) References Cited

OTHER PUBLICATIONS

Notice of Allowance mailed Jan. 3, 2013 in U.S. Appl. No. 12/551,101 (14 pages).

Notice of Allowance mailed Jun. 13, 2013 in U.S. Appl. No. 12/551,101 (9 pages).

Olsen, C. et al., "Fukuyama-Mitsunobu alkylation in amine synthesis on solid phase revisited: N-alkylation with secondary alcohols and synthesis of curtatoxins," Tetrahedron, 61:6046-6055 (2005).

Ordóñez, M. et al., "Highly diastereoselective synthesis of anti-γ-N-benzylamino-β-hydroxyphosphonates," Chemical Communications, 672-673 (2004).

Ranu, B. et al., "Reduction of Imines with Zinc Borohydride Supported on Silica Gel. Highly Stereoselective Synthesis of Substituted Cyclohexylamines," Journal of Organic Chemistry, 62(6):1841-1842 (1997).

Restriction Requirement mailed Sep. 19, 2011 in U.S. Appl. No. 12/551,101 (6 pages).

Rew, Y. et al., "Solid-Phase Synthesis of Amine-Bridged Cyclic Enkephalin Analogues via On-Resin Cyclization Utilizing the Fukuyama-Mitsunobu Reaction," Journal of Organic Chemistry, 67:8820-8826 (2002).

Sakamoto, I. et al., "Preparation of (Cyanomethylene)tributylphosphorane: A New Mitsunobu-Type Reagent," Chemical & Pharmaceutical Bulletin, 53(11):1508-1509 (2005).

Thayumanavan, R. et al., "Direct Organocatalytic Asymmetric Aldol Reactions of α-Amino Aldehydes: Expedient Syntheses of Highly Enantiomerically Enriched anti-β-Hydroxy-α-amino Acids," Organic Letters, 6(20):3541-3544 (2004).

\* cited by examiner

```
SEQUENCE LISTING

<160> NUMBER OF SEQ ID NOS: 42

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gln Val Gly Arg Gln Leu Ala Ile Ile Gly Asp Asp Ile Asn Arg
1               5                   10                  15

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gln Val Gly Arg Gln Leu Ala Ile Ile
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Gly Arg Gln Leu Ala Ile Ile Gly Asp Asp Ile Asn Arg
1               5                   10

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Norleucine

<400> SEQUENCE: 4

Glu Asp Ile Ile Arg Asn Ile Ala Arg His Leu Ala Gln Val Gly Asp
1               5                   10                  15

Ser Leu Asp Arg Ser Ile Trp
            20

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Ser Ser Asn Leu Gln Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Ser Asp Leu Gln Lys
1               5

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(12)
<223> OTHER INFORMATION: Any amino acid

<400> SEQUENCE: 7

Val Lys Lys Ile Thr Val Ser Ile Xaa Xaa Xaa Xaa Ile Ser Val Thr
1               5                   10                  15

Ile Lys Lys Val
            20
```

```
<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(9)
<223> OTHER INFORMATION: Any amino acid

<400> SEQUENCE: 8

Pro Gln Phe Asn Leu Arg Thr Xaa Xaa Thr Arg Leu Asn Phe Gln Pro
1               5                   10                  15

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Leu Lys Ile Lys Arg Leu Arg Lys Lys Phe Ala Gln Lys Met Leu
1               5                   10                  15

Arg Lys Ala Arg Arg Lys
            20

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Arg Gln Ala Arg Arg Asn Arg Arg Arg Arg Trp Arg Glu Arg Gln
1               5                   10                  15

Arg

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Thr Arg Tyr Leu Glu Gln Leu His Lys Leu Tyr Ser
1               5                   10

<210> SEQ ID NO 12
<211> LENGTH: 19
<212> TYPE: PRT
<213> ORGANISM: Phyllomedusa hypochondrialis

<400> SEQUENCE: 12

Phe Leu Ser Leu Ile Pro His Ala Ile Asn Ala Val Ser Ala Ile Ala
1               5                   10                  15

Lys His Asn
```

```
<210> SEQ ID NO 13
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Gly Phe Lys Asp Ile Ile Arg Ala Ile Arg Arg Ile Ala Val Pro
1               5                   10                  15

Val Val Ser Thr Leu Phe
            20

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Asp Phe Phe Pro Ala Gly Asp Cys Phe Arg Lys Gln Tyr Glu Asp
1               5                   10                  15

Gln Leu Ser

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Trp Lys Val Phe Lys Lys Ile Glu Lys Val Phe Ser Asn Ile Arg
1               5                   10                  15

Asp Gly Ile

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gln Glu Thr Phe Ser Asp Leu Trp Lys Leu Leu Pro Glu Asn Asn
1               5                   10                  15

Val

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Gln Leu Glu Glu Asp Leu Lys Gly Tyr Leu Asp Trp Ile Thr Gln
1               5                   10                  15
```

```
<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ile Ala Arg Leu Glu Glu Lys Val Lys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ile Ala Arg Leu Glu Glu Lys Val Lys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Leu Ala Ser Thr Ala Asn Ala Leu Arg Glu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Val Ala Gln Leu Lys Gln Lys Val Ala
1               5                   10

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Leu Ala Ser Thr Ala Asn Ala Leu Arg Glu Gln Val Ala Gln Leu
1               5                   10                  15

Lys Gln Lys Val Ala Ala Tyr
            20

<210> SEQ ID NO 23
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 23

Arg Ile Ala Arg Leu Glu Glu Lys Val Lys Thr Leu Lys Ala Gln Asn
1               5                   10                  15

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Val Ala Gln Leu Glu Asp Glu Lys Ser Ala Leu Gln
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Ala Ala Trp Asp Arg Glu Ile Asn Asn Tyr Thr
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Ala Ala Trp Asp Arg Glu Ile Asn
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Arg Lys Lys Arg Arg Asn Arg Arg Arg
1               5                   10

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Trp Lys Thr
1
```

```
<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp

<400> SEQUENCE: 29

Phe Trp Lys Thr
1

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: Ornithine
<220> FEATURE:
<221> NAME/KEY: MOD_RES
<222> LOCATION: (6)..(6)
<223> OTHER INFORMATION: D-Phe
<220> FEATURE:
<221> NAME/KEY: MOD_RES
<222> LOCATION: (9)..(9)
<223> OTHER INFORMATION: Ornithine

<400> SEQUENCE: 30

Phe Pro Val Xaa Leu Phe Pro Val Xaa Leu
1               5                   10

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Arg

<400> SEQUENCE: 31

Tyr Phe Gln Asn Cys Pro Arg Gly
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Phe Trp Lys Thr Ala
1               5
```

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Phe Trp Lys Ala Ala
1               5

<210> SEQ ID NO 34
<211> LENGTH: 4
<212> TYPE: PRT
<213> ORGANISM: Plasmodium falciparum

<400> SEQUENCE: 34

Asn Pro Asn Ala
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

His Phe Arg Trp
1

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Tyr Phe Gln Asn Cys Pro Arg Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Arg or Gln

<400> SEQUENCE: 37

Gly Pro Gly Xaa Pro Gly Gln
1               5

<210> SEQ ID NO 38
<211> LENGTH: 19
<212> TYPE: PRT
<213> ORGANISM: Phyllomedusa hypochondrialis -continued

```
<400> SEQUENCE: 38

Phe Leu Ser Leu Ile Pro His Ala Ile Asn Ala Val Ser Thr Leu Val
1               5                   10                  15

His His Phe

<210> SEQ ID NO 39
<211> LENGTH: 19
<212> TYPE: PRT
<213> ORGANISM: Phyllomedusa hypochondrialis

<400> SEQUENCE: 39

Phe Leu Ser Leu Ile Pro His Ala Ile Asn Ala Val Ser Thr Leu Ala
1               5                   10                  15

Asn His Gly

<210> SEQ ID NO 40
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Gln Glu Pro Pro Ile Ser Leu Asp Leu Thr Phe His Leu Leu Arg
1               5                   10                  15

Glu Met Leu Glu Met Ala Lys Ala Glu Gln Glu Ala Glu Gln Ala Ala
            20                  25                  30

Leu Asn Arg Leu Leu Leu Glu Glu Ala
        35                  40

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp

<400> SEQUENCE: 41

Tyr Trp Lys Thr
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp

<400> SEQUENCE: 42

Tyr Trp Lys Val
1
```

TEMPLATES FOR NUCLEATION AND PROPAGATION OF PEPTIDE SECONDARY STRUCTURE

BACKGROUND

Due to their essential role in the regulation of all physiological metabolic pathways, proteins can be useful drugs (as both agonists and/or antagonists) for the treatment of a variety of physiological disorders or diseases. The biological activity of proteins is often mediated by the distinct conformations that they exist in or are able to access. Thus, for example, proteins exhibit structural motifs, known as secondary structure, which include various turn (e.g., gamma- and beta-turns), sheet (beta sheet) and helical (alpha helix and pi helix) conformations. However, limitations in the size of molecules allowed into cells through naturally occurring non-invasive transduction pathways (e.g., endocytosis) generally limits or precludes the use of whole proteins as drugs. Consequently, short peptide sequences containing the functional domain(s) of the whole protein are preferred drug candidates.

Proteins can also be the targets of small molecule drugs. Designing small molecule drugs often involves assaying the activity of the drug candidates against shorter peptide sequences containing the functional domain(s) of the whole protein target. In both cases, because short peptide sequences often lack sufficient binding interactions (e.g., hydrogen bonding interactions, solvophobic interactions, electrostatic interactions, disulphide bonds, etc.), they are unable to access the same native, folded conformations when removed from the whole protein, thereby limiting their usefulness as drugs or drug targets.

SUMMARY

Provided herein are novel compounds which constrain peptides in order to mimic their natural biologically active conformations. In the compounds disclosed herein, one or more hydrogen bonds

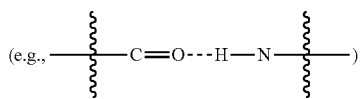

are replaced with a covalent hydrogen bond mimic,

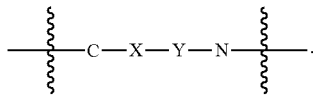

Compounds including such hydrogen bond mimics are capable of mimicking a variety of a secondary peptide structures, including γ-turns, β-turns, α-helical turns, and π-helical turns. Thus, the compounds of the present technology are also known herein as secondary structure mimics or templates for the nucleation and propagation of secondary structure. The compounds are useful as synthetic peptide drugs and as model targets for the design of small molecule drugs, as well as research tools for investigating the same. Also provided are methods of preparing the compounds and methods of using the compounds.

The foregoing summary is illustrative only and is not intended to be in any way limiting. In addition to the illustrative aspects, embodiments, and features described above, further aspects, embodiments, and features will become apparent by reference to the following drawings and the detailed description.

DETAILED DESCRIPTION

Figure 1A:
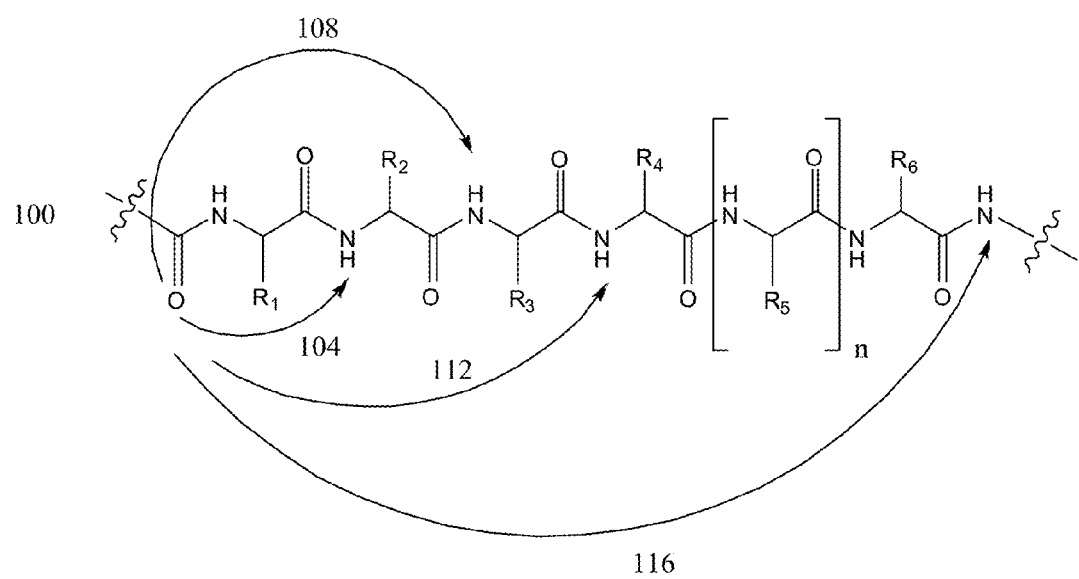
FIG. 1A depicts the hydrogen bonding interactions that lead to the formation of a variety of secondary structures.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The following terms are used throughout as described below, unless context clearly indicates otherwise.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the technology. Procedures for inserting such labels into the compounds of the technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. Substituted also includes multiple substitution e.g., disubstituted groups such as dialkyl, diaryl etc.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, carboxyalkyl, and the like.

Cycloalkyl groups include mono-, bi- or tricyclic alkyl groups having from 3 to 14 carbon atoms in the ring(s), or, in some embodiments, 3 to 12, 3 to 10, 3 to 8, or 3, 4, 5, or 6 carbon atoms. Illustrative monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups such as, but not limited to, adamantyl, and fused rings, such as, but not limited to, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Thus, alkenyl groups have from 2 to 12 carbon atoms, and typically from 2 to 10 carbons or, in some embodiments, from 2 to 8, 2 to 6, or 2 to 4 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 12 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass partially unsaturated and saturated ring systems, such as, for example, imidazolinyl and imidazolidinyl groups. The phrase "heterocyclyl group" includes fused ring species, including for example, hexahydropyrrolizine. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, pyrrolinyl, imidazolyl, imidazolinyl, pyrazolinyl, thiazolinyl, piperidyl, piperazinyl, morpholinyl, thiomorpholinyl, tetrahydropyranyl, tetrahydrothiopyranyl, oxathiane, dithianyl, pyranyl, dihydropyridyl, dihydrodithiinyl, dihydrodithionyl, homopiperazinyl, quinuclidyl, indolinyl, indolizinyl, benzoxazinyl, benzodithiinyl, benzoxathiinyl, benzothiazinyl, benzoxazolyl, benzothiazolyl, benzothiadiazolyl, benzo[1,3]dioxolyl, quinolizinyl, quinoxalinyl, quinazolinyl, cinnolinyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, piperazin-1-yl-methyl, tetrahydrofuran-2-yl-ethyl, and piperidinyl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the technology are not referred to using the "ene" designation. Thus, e.g., chloroethyl is not referred to herein as chloroethylene.

Alkoxy and cycloalkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The terms "carboxyl" and "carboxy" as used herein refers to a —COOH group.

The term "ester" as used herein refers to —COOR$^{30}$ groups. R$^{30}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H).

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently a substituted or unsubstituted alkyl, alkenyl, alkynyl, cycloalkyl, aryl, aralkyl, heterocyclylalkyl, or heterocyclyl group as defined herein. R$^{33}$ may also be —H.

The term "amine" (or "amino") as used herein refers to —NHR$^{35}$ and —NR$^{36}$R$^{37}$ groups, wherein R$^{35}$, R$^{36}$ and R$^{37}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{38}$R$^{39}$ and —NR$^{38}$SO$_2$R$^{39}$ groups, respectively. R$^{38}$ and R$^{39}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$).

The term "thiol" refers to —SH groups, while sulfides include —SR$^{40}$ groups, sulfoxides include —S(O)R$^{41}$ groups, sulfones include —SO$_2$R$^{42}$ groups, and sulfonyls include —SO$_2$OR$^{43}$. R$^{40}$, R$^{41}$, R$^{42}$, and R$^{43}$ are each independently a substituted or unsubstituted alkyl, cycloalkyl, alkenyl, alkynyl, aryl aralkyl, heterocyclyl or heterocyclylalkyl group as defined herein.

The term "urea" refers to —NR$^{44}$—C(O)—NR$^{45}$R$^{46}$ groups. R$^{44}$, R$^{45}$, and R$^{46}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{47}$)NR$^{48}$R$^{49}$ and —NR$^{47}$C(NR$^{48}$)R$^{49}$, wherein R$^{47}$, R$^{48}$, and R$^{49}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{50}$C(NR$^{51}$)NR$^{52}$R$^{53}$, wherein R$^{50}$, R$^{51}$, R$^{52}$ and R$^{53}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{54}$)=C(R$^{55}$)NR$^{56}$R$^{57}$ and —NR$^{54}$C(R$^{55}$)=C(R$^{56}$)R$^{57}$, wherein R$^{54}$, R$^{55}$, R$^{56}$ and R$^{57}$ are each independently hydrogen, a substituted or unsubstituted alkyl, cycloalkyl, alkenyl, alkynyl, aryl aralkyl, heterocyclyl or heterocyclylalkyl group as defined herein.

The term "imide" refers to —C(O)NR$^{58}$C(O)R$^{59}$, wherein R$^{58}$ and R$^{59}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{60}$(NR$^{61}$) and —N(CR$^{60}$R$^{61}$) groups, wherein R$^{60}$ and R$^{61}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{60}$ and R$^{61}$ are not both simultaneously hydrogen.

The term "leaving group" refers to an atom or group of atoms which may be replaced by another atom or group of atoms (e.g., a nucleophile, such as an amine, thiol, carbanion, and the like) during a chemical reaction. Illustrative leaving groups are well known in the art and include, but are not limited to halogen groups (e.g., I, Br, F, Cl), sulfonate groups (e.g., mesylate, tosylate, triflate), substituted alkylsulfonate groups (e.g., haloalkylsulfonate); C$_6$-aryloxy or substituted C$_6$-aryloxy groups; acyloxy groups and the like.

The term "protected" with respect to hydroxyl groups, amine groups, carboxy groups, and thiol groups refers to forms of these functionalities that are protected from undesirable reaction by means of protecting groups. Protecting groups such as hydroxyl, amino, carboxy, and thiol protecting groups, are known to those skilled in the art and can be added or removed using well-known procedures such as those set forth in Protective Groups in Organic Synthesis, Greene, T. W.; Wuts, P. G. M., John Wiley & Sons, New York, N.Y., (3rd Edition, 1999).

Hydroxyl groups may be protected as ethers, esters, and the like, including, but not limited to, substituted and unsubstituted ethyl, allyl, benzyl and silyl ethers, pyranyl ethers, and esters of substituted or unsubstituted acetate, benzoate and formate esters. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, t-butyl ether, allyl ether, benzyl ether; esters such as, but not limited to, benzoyl, formate, acetate, trichloroacetate, and trifluoroacetate.

Amino groups may be protected as substituted or unsubstituted amides, sulfonamides, carbamates, and the like, as well as silyl, alkyl, alkenyl and aralkyl amines. Amino-protecting groups (also known as N-protecting groups) comprise acyl groups such as formyl, acetyl, propionyl, pivaloyl, t-butylacetyl, phenylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, 4-nitrobenzenesulonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Typical amino-protecting groups include formyl, acetyl, benzoyl, pivaloyl, t-butylacetyl, phenylacetyl, phenylsulfonyl, 4-nitrobenzenesulfonyl, benzyl, 9-fluorenylmethyloxycarbonyl (Fmoc), t-butyloxycarbonyl (Boc) and benzyloxycarbonyl (Cbz).

Examples of protected thiol groups include, but are not limited to, thioethers such as S-benzyl thioether, S-t-butylthioether, and S—4-picolyl thioether; substituted S-methyl derivatives such as hemithio, dithio and aminothio acetals; and others.

Representative carboxy protecting groups are C$_1$ to C$_8$ alkyl (e.g., methyl, ethyl or tertiary butyl and the like); haloalkyl, such as trichloroethyl and the like; alkenyl, such as allyl and the like; cycloalkyl and substituted derivatives thereof such as cyclohexyl, cyclopentyl and the like; cycloalkylalkyl and substituted derivatives thereof such as cyclohexylmethyl, cyclopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocyclylcarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(alkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl) methyl and the like.

Those of skill in the art will appreciate that compounds of the technology may exhibit the phenomena of tautomerism, conformational isomerism, geometric isomerism and/or stereoisomerism. As the formula drawings within the specification and claims can represent only one of the possible tautomeric, conformational isomeric, stereoisomeric or geometric isomeric forms, it should be understood that the technology encompasses any tautomeric, conformational isomeric, stereoisomeric and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, imidazoles may exhibit the following isomeric forms, which are referred to as tautomers of each other:

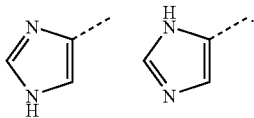

As readily understood by one skilled in the art, a wide variety of functional groups and other structures may exhibit tautomerism, and all tautomers of compounds as described herein are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the technology.

Pharmaceutically acceptable salts of the disclosed compounds are considered within the scope of the present invention. When such compound has a basic group, such as, for example, an amino group, pharmaceutically acceptable salts can be formed with inorganic acids (such as hydrochloric acid, sulfuric acid, and phosphoric acid), organic acids (e.g. formic acid, acetic acid, citric acid, succinic acid, trifluoroacetic acid, methanesulfonic acid, and p-toluenesulfonic acid) or acidic amino acids (such as aspartic acid and glutamic acid). When such compound has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. triethylamine, pyridine, picoline, ethanolamine) or basic amino acids (e.g. arginine, lysine and ornithine).

The compounds of the technology may exist as solvates, especially hydrates. Hydrates may form during manufacture of the compounds or compositions comprising the compounds, or hydrates may form over time due to the hygroscopic nature of the compounds. Compounds of the technology may exist as organic solvates as well, including DMF, ether, and alcohol solvates among others. The identification and preparation of any particular solvate is within the skill of the ordinary artisan of synthetic organic or medicinal chemistry.

Provided herein are novel compounds which are peptide secondary structure mimics and are useful as peptide drugs and model peptide drug targets, and research tools. Thus, in accordance with one aspect, provided herein is a group of compounds of Formula I:

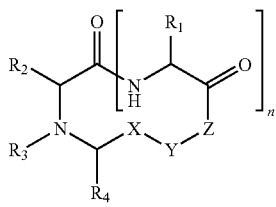

and stereoisomers, solvates, tautomers and pharmaceutically acceptable salts thereof, wherein Z is O or $—NR_5$ X is $—CR_aR_b—$;

Y is $—CR_cR_d—$;

$R_a$, $R_c$, $R_b$, and $R_d$ are independently —H or a substituted or unsubstituted alkyl or aralkyl group;

$R_1$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, $R_1$ together with the carbon to which it is attached and the adjacent nitrogen, forms a substituted or unsubstituted pyrrolidine, oxazolidine, thiazolidine, imidazolidine, or piperidine ring;

$R_2$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group; or $R_2$ and $R_3$ together with the atoms to which they are attached form a substituted or unsubstituted pyrrolidine, oxazolidine, thiazolidine, imidazolidine, or piperidine ring;

$R_3$ at each occurrence is independently —H, $—PG_3$, or a substituted or unsubstituted alkyl, cycloalkyl, cycloalkylalkyl, alkenyl, aryl, aralkyl, heterocyclyl, heterocyclylalkyl, heteroaryl or heteroaralkyl group; wherein $PG_3$ is an amino protecting group; or $R_2$ and $R_3$ together with the atoms to which they are attached form a substituted or unsubstituted pyrrolidine, oxazolidine, thiazolidine, imidazolidine, or piperidine ring;

$R_4$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, or a $—CHR_1—NH—R_6$ group;

$R_5$ is a —H, a substituted or unsubstituted alkyl, aryl, aralkyl, heteroaryl or a heteroaralkyl group, or a $—CHR_1—C(O)—R_7$ group;

$R_6$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, $—C(O)R_{10}$, $—C(O)OR_{10}$, $—[C(O)—CHR_1—NH]_m—R_{10}$, $—[C(O)—CHR_1—NH]_m—C(O)R_{10}$, or $—[C(O)—CHR_1—NH]_m—C(O)—OR_{10}$;

$R_7$ is a substituted or unsubstituted alkyl, cycloalkyl, cycloalkylalkyl, alkenyl, aryl, aralkyl, heterocyclyl, heterocyclylalkyl, heteroaryl or heteroaralkyl group, $—OR_{10}$, $—NR_{10}R_{10}$, or $—[NH—CHR_1—C(O)]_m—$;

$R_{10}$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group;

m is an integer from 1 to 20; and n is an integer from 0 to 20.

In some embodiments of the group of compounds of Formula I, $R_a$ is a substituted or unsubstituted $C_{1-6}$ alkyl group, $R_c$ is a substituted or unsubstituted $C_{1-6}$ alkyl group, or both $R_a$ and $R_c$ are substituted or unsubstituted $C_{1-6}$ alkyl groups. In other embodiments, $R_b$ is —H, $R_d$ is —H, or both $R_b$ and $R_d$ are —H.

In some embodiments of the group of compounds of Formula I, X is $CH_2$. In other embodiments, Y is $CH_2$. In yet other embodiments, each of X and Y is $CH_2$.

In certain embodiments of the group of compounds of Formula I, $R_1$ at each occurrence and $R_2$ are independently —H, benzyl optionally substituted with one or more OH or halogen, imidazolylmethyl, indolylmethyl, or a $C_{1-6}$ alkyl group optionally substituted with one or more substituents selected from F, Cl, Br, I, OH, $OPG_1$, SH, $SPG_2$, $NH_2$, $NHPG_3$, $C(O)OH$, $C(O)OPG_4$, $C(O)NH_2$, or $NHC(NH)NH_2$;

wherein $PG_1$ is a hydroxyl protecting group, $PG_2$ is a thiol protecting group, $PG_3$ is an amino protecting group, and $PG_4$ is a carboxyl protecting group. It will be understood by the skilled artisan that protecting groups are independently selected at each occurrence and that compatible protecting groups and, e.g., orthogonal protecting group strategies (where one protecting group may be selectively removed in the presence of another protecting group) are well known in the art.

In other embodiments of the group of compounds of Formula I, $R_1$ at each occurrence and $R_2$ are independently selected from the group consisting of —H, methyl, isopropyl, isobutyl, sec-butyl, hydroxymethyl, 1-hydroxyethyl, thiomethyl, 4-aminobutyl, 3-guanidinopropyl, benzyl, 4-hydroxybenzyl, indolylmethyl, methylthioethyl, carboxymethyl, carboxyethyl, carboxamidomethyl, carboxamidoethyl, and imidazolylmethyl.

In some embodiments, $R_3$ is —H or $PG_3$. In some embodiments, $R_3$ is an amino protecting group ($PG_3$) such as Phenylacetyl-(PhAc-), tert-butyloxycarbonyl-(′Boc-), 4-nitrobenzenesulfonyl (Nosyl) and fluoren-9-ylmethoxycarbonyl-(Fmoc-), etc. or a salt such as TFA or hydrohalide salts. In still other embodiments, $R_2$ and $R_3$ together form an unsubstituted pyrrolidine group.

In some embodiments of compounds of Formula I, $R_4$ is —H, $R_5$ is —H, or both $R_4$ and $R_5$ are —H. In other embodiments, $R_4$ is a —$CHR_1$—NH—$R_6$ group. In some embodiments, $R_6$ is —H, —$C(O)R_{10}$, —$C(O)OR_{10}$, —$[C(O)$—$CHR_1$—$NH]_m$—$R_{10}$, or —$[C(O)$—$CHR_1$—$NH]_m$—$C(O)$ $R_{10}$. In other embodiments, $R_5$ is a —$CHR_1$—$C(O)$—$R_7$ group. In some embodiments, $R_7$ is —$OR_{10}$, —$NR_{10}R_{10}$, or —$[NH$—$CHR_1$—$C(O)]_m$. In some embodiments, Z is —$NR_5$. In other embodiments, n is 0, 1, 2, or 3.

In another aspect, provided herein are methods of making compounds of Formula I. The methods involve the synthesis of various modified peptides and cyclization of the modified peptides to form the secondary structure mimics, i.e., compounds of Formula I. The modified peptides, methods of making the modified peptides, and methods of cyclizing the modified peptides are described below.

Modified Peptides

Provided herein are compounds of Formula III, useful in the synthesis of compounds of Formula I:

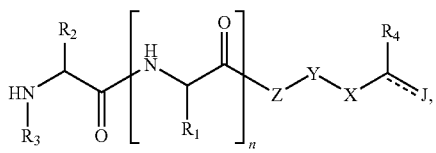

III wherein X, Y, Z, $R_1$, $R_2$, $R_3$, $R_4$, and n are defined as described above with respect to Formula I and J is a leaving group (L) or OH (the dashed line indicating a single bond) or an oxo group (the dashed line indicating a double bond). Illustrative leaving groups include halogen and sulfonyl groups such as, mesylate, tosylate, triflate, and the like. Compounds of Formula III are modified peptides, which are cyclized to form the compounds of Formula I, as further described below.

In some embodiments, the compound of Formula III is selected from the group of compounds of Formula IIIA:

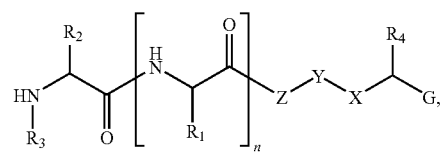

IIIA wherein X, Y, Z, $R_1$, $R_2$, $R_3$, $R_4$, and n are defined as described above with respect to Formula I and G is a halogen.

In other embodiments, the compound of Formula III is selected from a group of compounds of Formula IIIB:

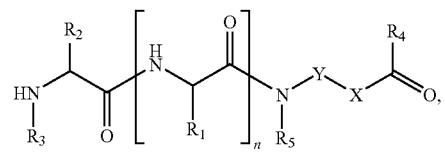

IIIB wherein X, Y, $R_1$, $R_2$, $R_3$, $R_4$, $R_5$, and n are defined as described above with respect to Formula I.

In yet other embodiments, the compound of Formula III is selected from a group of compounds of Formula IIIC:

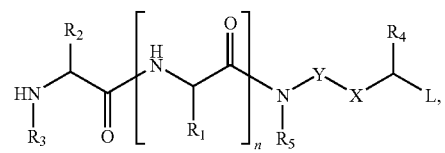

IIIC wherein X, Y, $R_1$, $R_2$, $R_3$, $R_4$, $R_5$, and n are defined as described above with respect to Formula I and L is a leaving group. Illustrative leaving groups include halogen and sulfonyl groups such as, mesylate, tosylate, triflate, and the like.

Synthesis of Modified Peptides

Also provided herein are methods for synthesizing the modified peptides described above. Modified peptides of Formula III may be prepared as depicted in Schemes 1-3. In each scheme X, Y, $R_1$, $R_2$, $R_3$, $R_4$, $R_5$, and n are defined as described above with respect to Formula I, $PG_3$ is an amino-protecting group, and G is a halogen.

Scheme 1

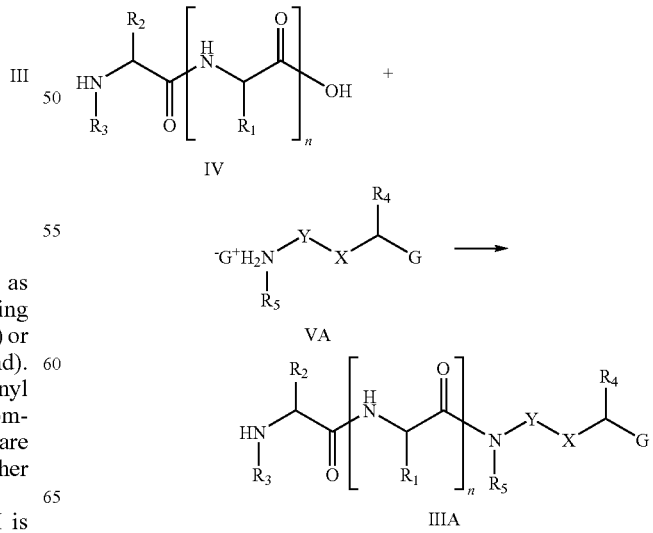

The compound of Formula III (e.g., IIIA, where Z is NR$_5$) may be prepared by coupling the compound of Formula IV (wherein R$_3$ is PG$_3$) to a compound of Formula VA using standard peptide coupling procedures and reagents including, but not limited to, coupling agents, acid halides, active esters, mixed anhydride, and the like. The amino-protecting group PG$_3$ may be removed (to give R$_3$=H) or removed and replaced with another R$_3$ group by techniques known in the art (e.g., reductive amination with an aldehyde or ketone or acylation). Those of skill in the art will understand that a variety amino protecting groups may be used, including, but not limited to, Boc, Nosyl, Fmoc, and Cbz. Alternatively, R$_3$ is not a protecting group but the nitrogen to which it is attached bears an N-protecting group which may be removed after reaction to give a compound of Formula III.

For illustration only, the procedures disclosed in the following references can be used to affect the peptide coupling reaction. "Peptide synthesis and methodology" in *Peptides Design, Synthesis and Biological Activity*, 1994, Ch. I:11-80; edited by Channa Basava and G. M. Ananthatamaiah, Birkhauser, Boston; Collins, J. M.; Collins, M. J., *Microwaves in Organic Synthesis* (2d Ed.), 2006, 2:898-930; Hojo, K.; Ichikawa, H.; Fukumori, Y.; Kawasaki, K., *Int. J. Pept. Res. Therapeutics*, 2008, 14(4):373-380; Sabatino, G.; Papini, A. M., *Curr. Opinion Drug Disc. Development*, 2008, 11(6):762-770; Elmore, D. T., *Amino Acids, Peptides, and Proteins*, 2007, 36:82-130; Cudic, P.; Stawikowski, M., *Mini-Rev. Org. Chem.*, 2007, 4(4):268-280; Coin, I.; Beyermann, M.; Bienert, M., *Nature Protocols*, 2007, 2(12):3247-3256.

For example, Boc-Ala-Ala-Ala-NH—(CH$_2$)$_3$—Br may be prepared by the coupling reaction between Boc-Ala-Ala-OH with 1-amino-3-propylbromide hydrobromide in the presence of NMM, and ECF using THF as solvent. ECF is added to a cold solution of Boc-Ala-Ala-OH and NMM in THF under an inert atmosphere (e.g., nitrogen, argon) and stirred. To this, a solution of 1-amino-3-propylbromide hydrobromide in a mixture of solvents such as THF and DMF is added followed by NMM. The cold solution can be warmed to a suitable temperature such as, for example, 25° C. or room temperature, and the reaction can continued for a suitable period of time to effect maximum yields. The reaction can be monitored by TLC and the product can be characterized using NMR.

As shown in Scheme 2, compounds of Formula III incorporating longer peptides can also be synthesized from shorter (di, tri, tetra, etc.) peptide amidoalkyl bromides by N-terminal extension, i.e., by coupling the free amine of the peptide amidoalkyl bromides with the free acids of the desired peptides. For example, Boc-protected peptides can be converted to their TFA salts by reaction with trifluoroacetic acid and coupled with a second Boc-protected amino acid as shown in Scheme 2. The latter steps may be repeated to provide peptides of desired length.

Scheme 2

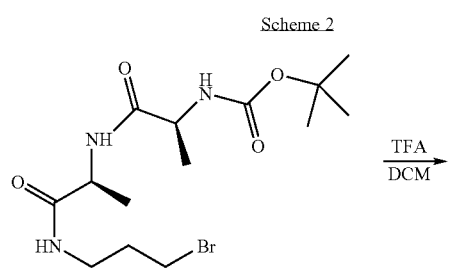

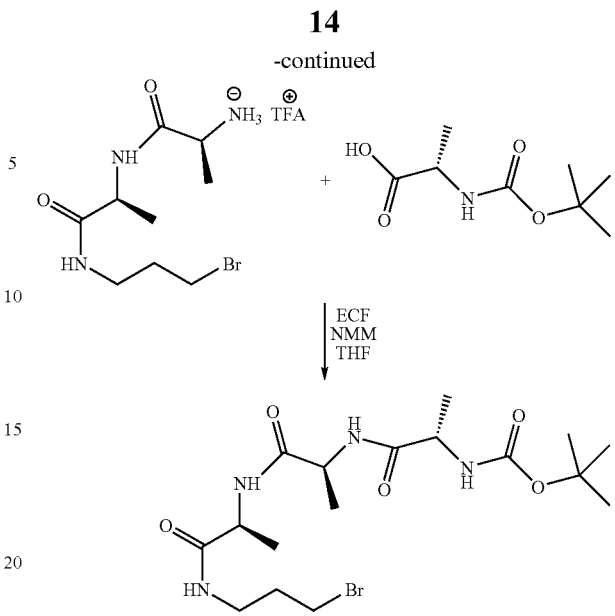

As shown in Scheme 3, compounds of Formula IV (wherein R$_3$ is PG$_3$) may also be alkylated with compounds of Formula VB to provide compounds of Formula III (i.e., IIIA where Z is O). The amino-protecting group PG$_3$ may be removed (to give R$_3$=H) or removed and replaced with another R$_3$ group by techniques known in the art (e.g., reductive amination with an aldehyde or ketone or acylation). Those of skill in the art will understand that a variety amino protecting groups may be used, including, but not limited to, Boc, Nosyl, Fmoc, and Cbz. Alternatively, R$_3$ is not a protecting group but the nitrogen to which it is attached bears an N-protecting group which may be removed after reaction to give a compound of Formula III.

Scheme 3

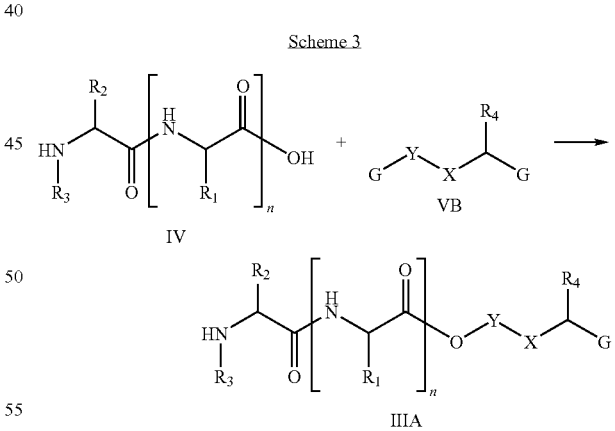

Thus, e.g., a nosyl-protected amino acid can be reacted with a dibromoalkane in presence of a base such as an alkali metal carbonate in a suitable solvent such as DMF. For illustration only, the procedure disclosed in *J. Am. Chem. Soc.*, 2004, 126:12252-12253 can be used to effect the alkylation reaction.

The starting materials for the above syntheses, compounds of Formula VA and VB, may be prepared according to Schemes 4A and 4B, respectively.

Scheme 4A

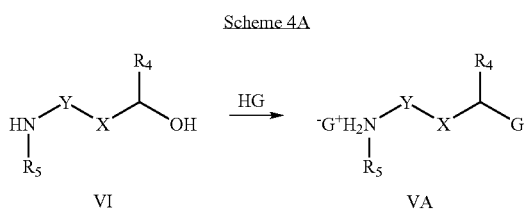

As shown in Scheme 4A, the hydroxyl group of a compound of Formula VI (prepared as described in Scheme 6 below) may be converted to a halogen via standard techniques including, but not limited to, treatment with HBr, PBr$_3$, POCl$_3$, or PPh$_3$ and N-bromosuccinimide (NBS) to form compounds of Formula VA. For example, halo-propyl amino halide compounds of Formula VA can be synthesized by halogenation of 3-halo-1-propyl alcohol in accordance with the synthetic protocol disclosed in *J. Org. Chem.*, 2008, 73:168-176 or *J. Org. Chem.*, 2003, 68:2960, as described in Step 1 of Example 1, herein.

Scheme 4B

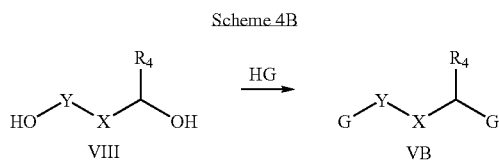

Similarly, as shown in Scheme 4B, bis hydroxy compounds of Formula VIII may be converted to bis halides by the same techniques described for making compounds of Formula VA above.

Compounds of Formula IIIB and IIIC may be prepared in a two step process according to Scheme 5. The variables X, Y, R$_1$, R$_2$, R$_3$, R$_4$, R$_5$ and n, are defined as described above with respect to Formula I, PG$_3$ is an amino-protecting group, and L is a leaving group.

active esters, mixed anhydride, and the like. For example, the N-protected amino acid of Formula IV can be coupled with the amino-propyl alcohol of Formula VI using NMM in THF and ECF as described above. The peptide coupling in Scheme 5 may also be achieved by using other methods known in the art, e.g., *Org. Biomol. Chem.*, 2007, 1915-1923, which describes coupling between an amine and an acid using HATU, TEA, DMF (compound 13a, 13b), or *European Journal of Medicinal Chemistry*, 2002, 37(7):573-584, which describes the use of several coupling reagents such as Bop, DIPEA, DCM. or, Bop, HOBt, DIEA, DMF or, DCC, HOSu, DMF, NMM.

In a second step, the hydroxyl group of compounds of Formula VII may be oxidized. For example, the hydroxyl group may be oxidized using the standard Swern oxidation protocol where oxalyl chloride and DMSO are mixed at −78° C. in a solvent like dichloromethane and the alcohol and a base such as triethyl amine is added to it. The mixture is warmed to a temperature of about 25° C. Solvent extraction in solvents like ethyl acetate or DCM or ether, followed by purification in silica gel flash column chromatography will yield the desired oxidized (carbonyl) compound. For illustration only, the procedure disclosed in, for example, *Tet. Lett.*, 1995, 36(51):9401-9404; or *Bioorg. Med. Chem. Lett.*, 1995, 5(3):219-22, can be employed for the oxidation reaction. Removal of the amino-protecting group PG$_3$ provides compounds of Formula IIIB. Standard deprotection methods known in the art, for example, *Protective Groups In Organic Synthesis* (3d Ed.), Theodora W. Greene and Peter G. M. Wuts, 1999, John Wiley & Sons, Inc., can be used to remove the amino protection group.

In an alternative second step, the hydroxyl group of compounds of Formula VII may be converted to a leaving group. For example, the hydroxyl may be sulfonylated with an appropriate sulfonyl chloride or anhydride such as mesyl chloride, tosyl chloride or triflic anhydride, in the presence of a base. Illustrative bases include tertiary amine (e.g., triethyl amine or diisopropyl ethylamine) or pyridine. By way of example only, the hydroxyl group may be converted to Br by Scheme 5

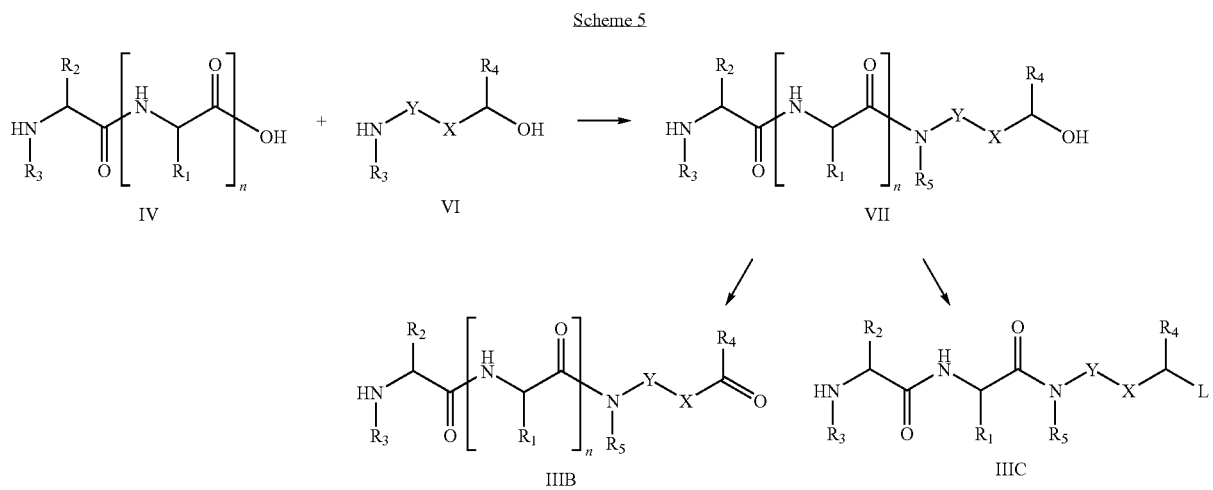

As shown in the first step of Scheme 5, compounds of Formula IV (wherein R$_3$ is PG$_3$) can be coupled with compounds of Formula VI to provide compounds of Formula VII using standard peptide coupling procedures and reagents, including, but not limited to, coupling agents, acid halides, exposing the compound of Formula IV to NBS and triphenylphosphine. This reaction for the conversion of an alcohol group to the bromide group can be conducted by dissolving the alcohol and PPh$_3$ in THF at a suitable temperature such as −15° C. and adding to it a solution of NBS in THF. The reaction can be monitored by TLC and the product can be characterized by NMR and IR. Removal of the amino-protecting group PG₃ provides compounds of Formula IIIC. The amino-protecting group PG₃ may also be removed prior to oxidation or from compounds of Formula IV prior to coupling with compounds of Formula VI.

In another embodiment, after the second step the amino-protecting group PG₃ may be removed and replaced with another R₃ group by techniques known in the art (e.g., reductive amination with an aldehyde or ketone or acylation). Alternatively, R₃ is not a protecting group but the nitrogen to which it is attached bears an N-protecting group which may be removed after reaction to give a compound of Formula IIIB or IIIC.

As shown in Scheme 6, compounds of Formula VI can be synthesized from the corresponding amino acids using a standard protocol for reducing amino acids to amino alcohols such as, e.g., treatment with I₂ and NaBH₄ in THF, with complete retention of stereochemistry. For example, the process disclosed in *J. Org. Chem.*, 1993, 58(13):3568-3571, can be used to convert the following amino acid to its corresponding amino alcohol in high yields by using NaBH₄ and I₂ in THF under refluxing conditions.

Scheme 6

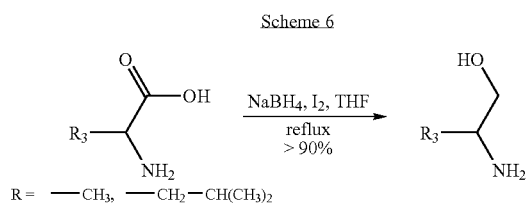

Schemes I, II, and III each begin from compounds of Formula IV. Such compounds can be made by either standard peptide synthesis solution-phase methods employing standard protecting group strategies and coupling strategies or solid phase peptide synthesis (SPPS) methodology. (See Example 3.)

Cyclization of Modified Peptides

The compounds of Formula III may be cyclized to form the secondary structure mimics described herein, i.e., the compounds of Formula I. The methods include cyclizing a compound of Formula III to produce a compound of Formula I:

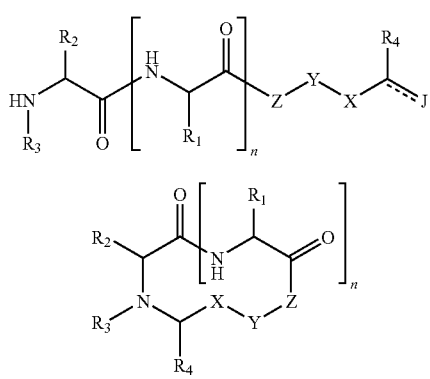

wherein
Z is O or NR₅
X is —CR$_a$R$_b$—;
Y is —CR$_c$R$_d$—;

J is —OH, a leaving group or an oxo group, and the dashed line indicates a single bond to OH or the leaving group or indicates a double bond to the oxo group;

R$_a$, R$_c$, R$_b$, and R$_d$ are independently —H or a substituted or unsubstituted alkyl or aralkyl group;

R₁ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, R₁ together with the carbon to which it is attached and the adjacent nitrogen, forms a substituted or unsubstituted pyrrolidine, oxazolidine, thiazolidine, imidazolidine, or piperidine ring;

R₂ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group; or R₂ and R₃ together with the atoms to which they are attached form a substituted or unsubstituted pyrrolidine, oxazolidine, thiazolidine, imidazolidine, or piperidine ring;

R₃ at each occurrence is independently —H, —PG₃, or a substituted or unsubstituted alkyl, cycloalkyl, cycloalkylalkyl, alkenyl, aryl, aralkyl, heterocyclyl, heterocyclylalkyl, heteroaryl or heteroaralkyl group; wherein PG₃ is an amino protecting group; or R₂ and R₃ together with the atoms to which they are attached form a substituted or unsubstituted pyrrolidine, oxazolidine, thiazolidine, imidazolidine, or piperidine ring;

R₄ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, or a —CHR₁—NH—R₆ group;

R₅ is a —H, a substituted or unsubstituted alkyl, aryl, aralkyl, heteroaryl or a heteroaralkyl group, or a —CHR₁—C(O)—R₇ group;

R₆ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —C(O)R₁₀, —C(O)OR₁₀, —[C(O)—CHR₁—NH]$_m$—R₁₀, —[C(O)—CHR₁—NH]$_m$—C(O)R₁₀, or —[C(O)—CHR₁—NH]$_m$—C(O)—OR₁₀;

R₇ is a substituted or unsubstituted alkyl, cycloalkyl, cycloalkylalkyl, alkenyl, aryl, aralkyl, heterocyclyl, heterocyclylalkyl, heteroaryl or heteroaralkyl group, —OR₁₀, —NR₁₀R₁₀, or —[NH—CHR₁—C(O)]$_m$—;

R₁₀ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group;

m is an integer from 1 to 20; and n is an integer from 0 to 20.

The cyclization reaction can be effected by several methods in which the compound of Formula III is selected from a compound of Formula IIIA, IIIB, or IIIC. For example, the cyclization reaction may be effected by intramolecular N-alkylation of compounds of, e.g., Formula IIIC, or reductive amination of compounds of, e.g., Formula IIIB. The N-alkylation can be effected by macrocyclic N-alkylation of nosyl amido peptides as in Scheme 7. Alternatively, cyclization may be effected by macrolactamization of N-protected β-sheet mimics as demonstrated in Scheme 8. The routes to protected β-turn mimics shown in the scheme may be extrapolated to synthesize larger cyclized peptide mimetics.

Scheme 7

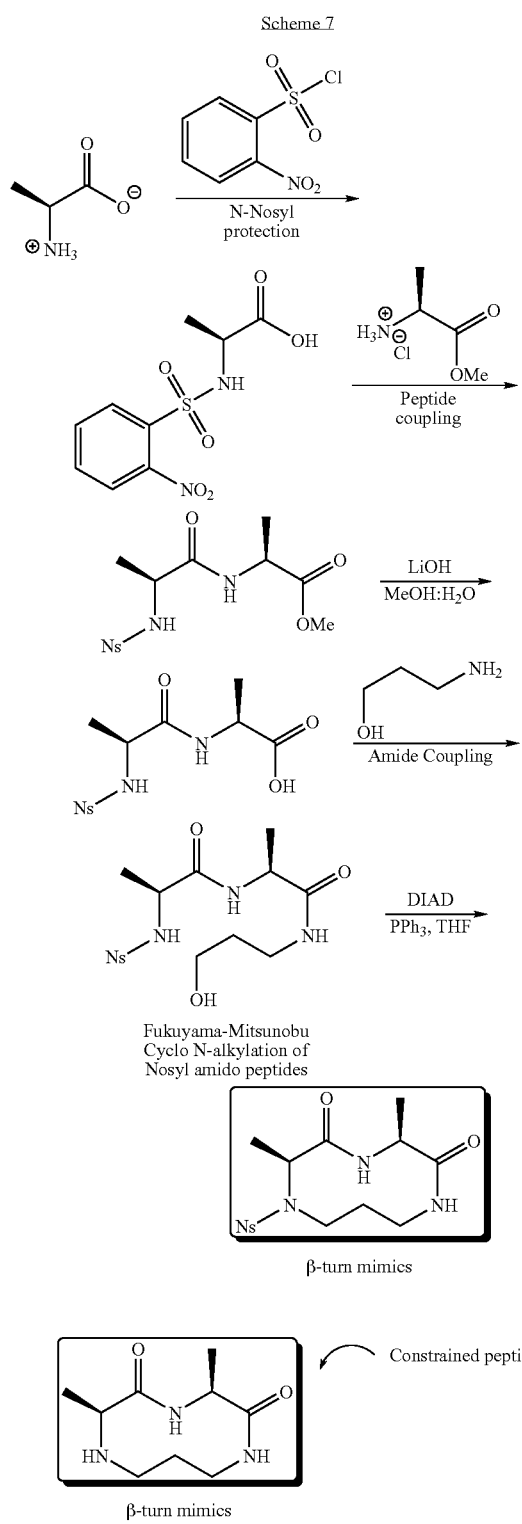

β-turn mimics

Constrained peptides

β-turn mimics

In accordance with Scheme 7, nosyl-protected amides can be synthesized from nosyl chloride and an amine, in the presence of a base such as TEA, in a DCM solution as disclosed in *Tet Lett.,* 2007, 4687-4690; or *Org. Biomol. Chem.,* 2007, 1915-1923; or *Bioorg. Med. Chem.,* 2003, 11:5461-5484. The synthesis can also be conducted using NsCl in NMM and DCM at 0° C. as disclosed in e.g. *European Journal of Medicinal Chemistry,* 2002, 37(7):573-584.

The N-nosyl protected amino acid can be subjected to peptide coupling with the hydrohalide salt of methyl-2-aminopropionate using standard conditions known in the art. This N-nosyl protected amino alkoxide can then be converted to the corresponding N-nosyl protected amino acid using a suitable strong base such as LiOH. The N-protected amino acid can be subjected to amide coupling with an aminoalkyl alcohol. The N-nosyl-peptide can then be cyclized under Fukuyama-Mitsunobu N-alkylating conditions. Fukuyama-Mitsunobu protocol uses DIAD or DEAD and a trialkyl phosphine like $PPh_3$ in a suitable solvent like THF or DMF. For illustration only, the Fukuyama-Mitsunobu procedure disclosed in the following references can be used.

Zapf, C. W.; Del V., Juan R.; Goodman, M., *Bioorg. Med. Chem. Lett.,* 2005, 15(18):4033-4036; (synthesis of compound 4 in FIG. 1 of) *Bioorg. Med. Chem.,* 2005, 13:5936-5948; (solid phase synthesis of compound 9 in scheme—2 in) Olsen, C. A.; Christensen, C.; Nielsen, B.; Mohamed, F. M.; Witt, M.; Clausen, R. P.; Kristensen, J. L.; Franzyk, H.; Jaroszewski, J. W. *Org. Lett.,* 2006, 8(15):3371-3374; Kunio Saruta, Tsuyoshi Ogiku, *Tet. Lett.* 2008, 49:424-427; Fukuyama T., Cheung M., Chung-Kuang Jow, Hidai Y., Kan T., *Tet. Lett.,* 1997, 38:5831-5834; Piró J., Rubiralta M., Giralt E., Diez A., *Tet. Lett.,* 2001, 42:871-873; Turner J. J., Filippov D. V., Overhand M., Van der Marel G. A., Van Boom J. H., *Tet. Lett.,* 2001, 42:5763-5767. Nosyl deprotection using standard methods in the art will provide the desired β-turn mimic.

Scheme 8

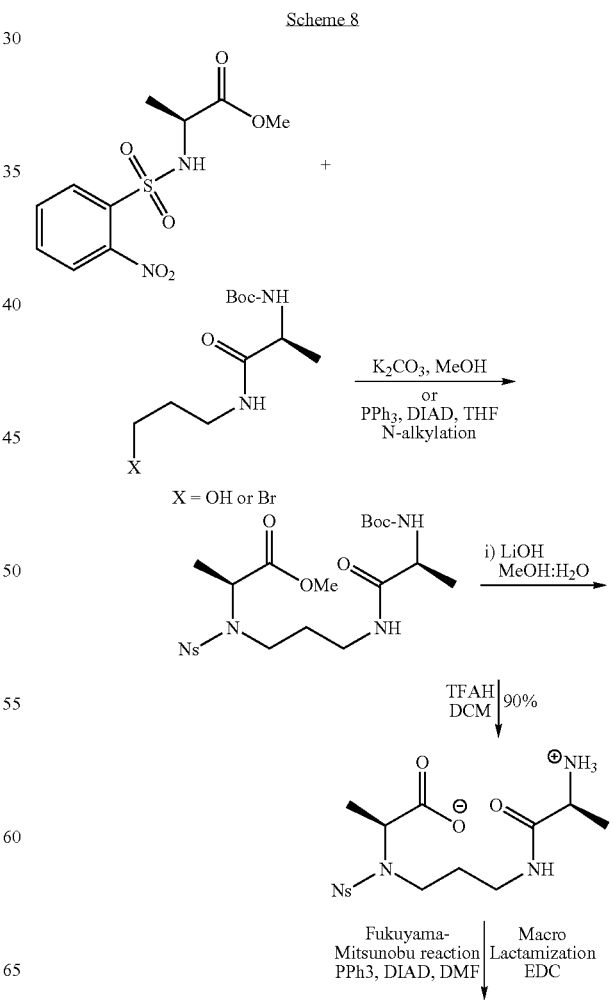

-continued

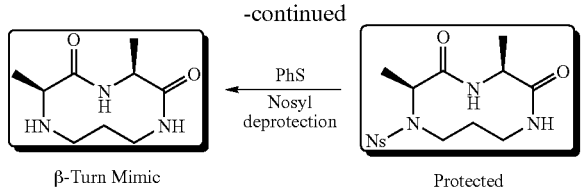

β-Turn Mimic     ← PhS / Nosyl deprotection     Protected β-Turn Mimic

N-nosyl protected peptides can be prepared as per the method disclosed in Scheme 8. Intermolecular N-alkylation may be accomplished for example by N-alkylation of N-nosyl protected amides with alkyl bromides, for example, as disclosed in Fukuyama T., Cheung M., Chung-Kuang Jow, Hidai Y., Kan T., *Tet. Lett.*, 1997, 38:5831-5834. This can be effected by known methods such as reacting the N-nosyl protected alkoxy amino acid with an alkyl bromide in a solvent like DMF or $CH_3CN$ using a base such as $K_2CO_3$ or $Na_2CO_3$. Alternatively, intermolecular N-alkylation may be accomplished, for example, by N-alkylation of N-Nosyl protected amides with alkyl alcohols. For illustration only, the process disclosed in Cheung M., Chung-Kuang Jow, Hidai Y., Kan T., *Tet. Lett.*, 1997, 38:5831-5834 can be used. This can be effected by the Fukuyama-Mitsunobu protocol where the N-nosyl amide is reacted with the alkyl alcohol in the presence of a trialkyl phosphine like $PPh_3$ and DIAD or DEAD in a solvent like THF or DMF. The Nosyl peptide can then be converted to the corresponding carboxylic acid using a base like LiOH in a mixture of solvents containing different proportions of MeOH and water. This compound can then be converted to the corresponding ammonium salt in the presence of a strong acid such as TFA (trifluoroacetic acid) in a solvent such as DCM. The N-nosyl amino acid thus prepared can be cyclized through macrolactamization under standard peptide coupling conditions, for example, in the presence of EDC and HOBT, in a solvent like THF or DMF. The formation of the Nosyl protected β-turn mimic can be confirmed by NMR. Nosyl deprotection using standard methods in the art will provide the β-turn mimic.

Alternative methods for inter molecular N-alkylation of nosyl amides described in the following publications can also be used. *J. Am. Chem. Soc.*, 2004, 126:12252-12253, describes the N-alkylation reaction using dibromoalkane. *Tet. Lett.*, 2007, 48(27):4687-90, describes the process using $K_2CO_3$, DMF, r.t. propargyl bromide. (87%)—in the presence of esters or amido ester. *Org. Biomolec. Chem.*, 2007, 5(12):1915-23, discloses the reaction using $K_2CO_3$ and DMF at r.t. for 3 h. Alkylation is 82% in presence of $O$—$Si(Pr-i)_3$, amido ester. N-alkylation using $Na_2CO_3$, $Bu_4N^+HSO_4^-$, DMSO for 8 h at 30° C. is described in *Synlett*, 2006, (5):741-744. *Bioorg. Med. Chem.*, 2003, 11(24):5461-5484 discloses the process using $Cs_2CO_3$, DMF, at r.t. to 60° C., overnight in bromo propyl alcohol. *European Journal of Medicinal Chemistry*, 2002, 37(7):573-584, describes N-alkylation using an amino alkyl bromide substrate with $Cs_2CO_3$ and DMF for 30 min at r.t.

Nosyl deprotection can be effected by standard methods known in the art e.g., using a thiol following the procedure described in: *J. Am. Chem. Soc.*, 2004, 126:12252-12253. Other methods such as those disclosed in *Bioorg. Med. Chem.*, 2003, 11:5461-5484, or *Org. Biomol. Chem.*, 2008, 6:2158-2167, using PhSH, $K_2CO_3$, acetonitrile; *European Journal of Medicinal Chemistry*, 2002, 37(7):573-584, using PhSH, DIEA, DMF, 2-6 h; and *Org. Biomol. Chem.*, 2007, 1915-1923, using $HSCH_2COOH$, LiOH, DMF, r.t., can also be used for nosyl deprotection.

In a further embodiment, traditional macrolactamization techniques may also be used to cyclize N-protected compounds to give of Formula I. For example, a compound of Formula IX may be cyclized with a variety of coupling reagents at high dilution.

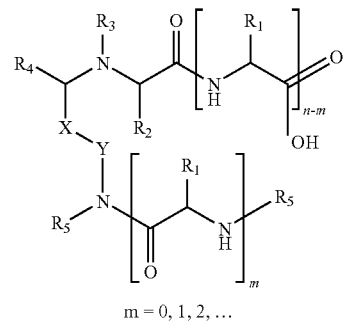

IX $m = 0, 1, 2, \ldots$

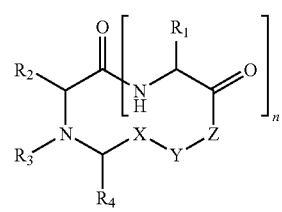

I

The variables of Formula IX are defined as described above with respect to Formula I. Such macrolactamization reactions can be conducted using methods described in the art such as, e.g., in *J. Am. Chem. Soc.*, 2007, 129(14):4175-4177. A TFA salt of the amino peptidic acid can be cyclized using HOBT, EDCl and DIPEA in DMF solvent by the macrolactamization technique. Alternatively, the process disclosed in *J. Am. Chem. Soc.*, 2005, 127(18):6563-6572, using BOP and DIPEA in DMF can also be employed to effect macrolactamization in good yields.

In some embodiments, the cyclization can be effected using the TFA salt of the peptide. Scheme 9 illustrates this procedure for conversion of TFA salt of the acyclic peptide to the cyclized product.

Scheme 9

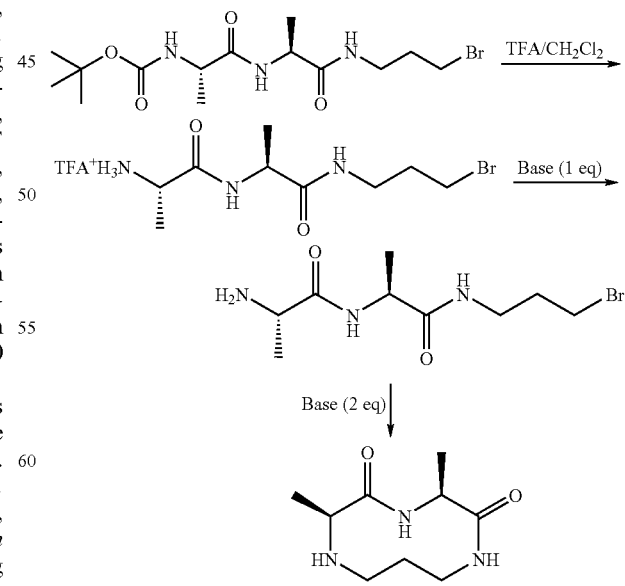

The TFA salt can be prepared by the general procedure for Boc-deprotection by treating the Boc-protected compound to trifluoroacetic acid in a standard solvent such as DCM or DMF. This TFA salt can be converted in to the corresponding free amine by reacting it with a suitable base such as for e.g., sodium or potassium bicarbonate. On continuation of the reaction, the acyclic free amine is converted to the cyclized product in high purity and yield.

A variety of solvents and bases may be used for the above processes. In some embodiments, the solvent is water, methanol, tetrahydrofuran, acetonitrile, or dimethylformamide. In some embodiments, the base is sodium carbonate, sodium bicarbonate, potassium carbonate, or potassium bicarbonate. In some embodiments, a buffer may be used with pH between 7-13 at millimolar concentrations such as 50 mM, 100 mM, 200 mM, 500 mM, 1 M or 2 M, using any of the standard polybasic, polyacidic, zwitter ionic or hydroxyl zwitter ionic buffers such as sodium phosphate, glycine, diglycine, sodium acetate, boric acid, TRIS, MOPS, succinic acid, MES, etc. that are known to buffer in the desired pH range. The buffers may or may not contain different other non-buffering salts like NaCl, $MgSO_4$, $MgCl_2$, or additives like EDTA, trifluoroethanol or ethanol, etc. Generally, only two equivalents of base are needed (one each for scavenging the two molar equivalents of protons that are formed during the N-alkylation cyclization reaction). Alternatively, greater equivalents of bases, like 3-20 equivalents, may be used to increase the rate of the reactions. The reaction times and reaction temperatures may vary. By way of example only, the reaction time may be no more than about 2 hours, about 5 hours, about 10 hours, about 20, about 50 hours, about 100 hours, or about 200 hours. In some embodiments, the reaction temperature is about 25° C. or about 35° C. or about 50° C. or about 70° C. or about 90° C. Both the ability to use a variety of solvents and bases under mild reaction conditions allows a wide variety of hydrophobic, hydrophilic, and amphipathic modified peptides to be cyclized via the disclosed intramolecular N-alkylation reaction. Moreover, the reaction yields are quite high. In some embodiments, the reaction yield is greater than about 75%, about 80%, greater than about 85%, greater than about 90%, greater than about 95%, greater than about 98%, or greater than about 99%. In other embodiments, the reaction yield is about 100%. Because by-products of the N-alkylation cyclization reaction are limited, separation of the desired product (the compounds of Formula I) is straightforward. By way of example only, the product may be recovered by filtering it from the reaction mixture.

Cyclization by reductive amination may be accomplished by exposing compounds of Formula III to a reducing agent such as $NaBH_3CN$, $NaB(OAc)_3H$ in the presence of an acid like acetic acid in a solvent like MeOH and in the presence of a dehydrating agent like 4A molecular sieves, or $Na_2SO_4$. For illustration only, the procedure disclosed in *Macromolecules*, 2007, 40(5):1480-1488; or *Org. Lett.*, 2003, 5(22):4227-4230 can be used to effect the reductive amination.

In some embodiments of the method, the compound of Formula III is selected from a compound of Formula IIIA or a compound of Formula IIIC and the cyclization reaction involves intramolecular N-alkylation. In other embodiments, the compound of Formula III is selected from a compound of Formula IX and the cyclization reaction involves macrolactamization.

Figure 1B:
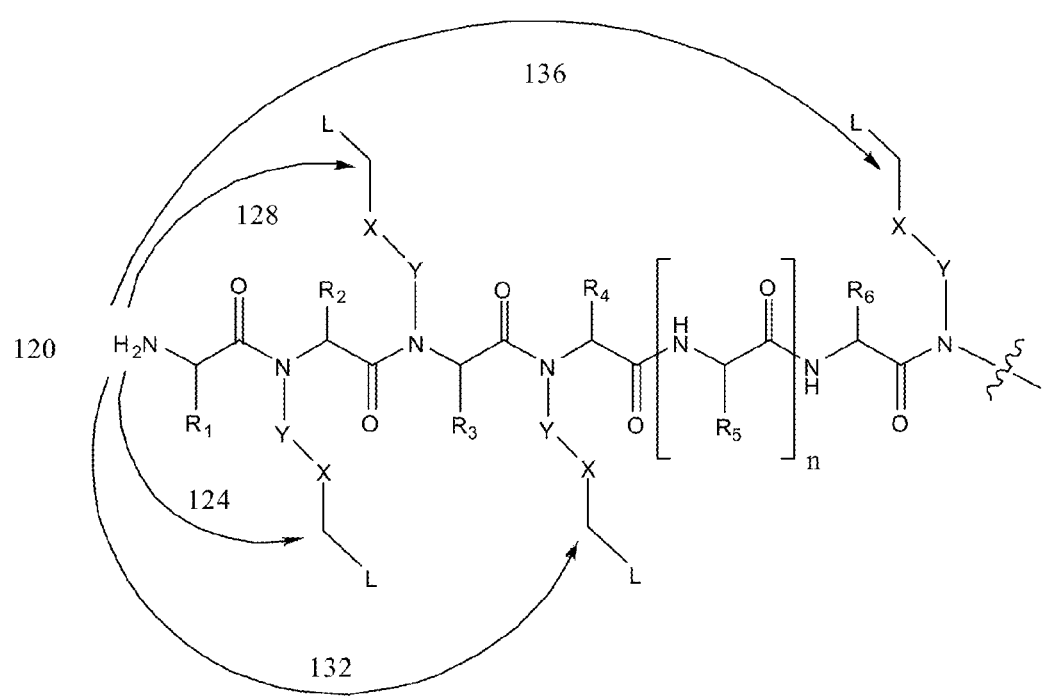
FIG. 1B depicts an illustrative embodiment of a modified peptide, which can be prepared and cyclized according to the methods described herein to provide a variety of secondary structure mimics.

The compounds disclosed herein can mimic and/or initiate and propagate a wide variety of peptide and protein secondary structure. FIG. 1A shows how hydrogen bond interactions in a linear peptide (100) lead to various illustrative secondary structures, including γ-turns (104), β-turns (108), α-helices (112) and sheets and folds (116). As shown in FIG. 1B, by modifying the amino nitrogen of different peptide bonds and subsequently cyclizing the modified peptide 120 using the disclosed reaction schemes, numerous secondary structure mimics may be achieved, including γ-turns (124), β-turns (128), α-helices (132) and sheets and folds (136). Other secondary structure mimics not shown in FIG. 1 are also possible.

In one aspect, the technology provides both beta-turn having variable sizes and bond angles and variable side chain constituents, and peptides containing such beta-turn mimetics internally or at either end or at the end, connecting both the termini. The key feature of the art is that such constrained beta-turn mimetics are made directly from native peptide sequences that are contained in natural agonists and antagonists, i.e., there is no need to first search for a drug lead. The natural sequence of the native peptide being mimicked in the biological system is itself the drug lead, and is constrained by this technology without mutation to any of its structural features. Hence, also, the molecular recognition surface of the natural substrate is completely retained. Such beta-turn mimetics, or peptides containing the same, are conformationally restricted, and as such are useful for the design and synthesis of conformationally restricted antigens for making synthetic vaccines or for making antibodies for diagnostic purposes. Additionally, they are useful for mapping critical receptor-ligand interactions for purposes of designing non-peptide therapeutics. They are useful not only for initial mapping, based upon which beta-turn mimetics bind the receptor, from knowledge of the natural peptide sequences that bind to the receptors or the biological target, but are also useful for subsequent investigation directed toward identification of molecular interactions and conformations critical to the binding. For example, if a beta-turn mimetic represented by the structural formula Ala-Phe-Trp-Lys-Thr-Ala (SEQ ID NO: 32) (containing the Phe-Trp-Lys-Thr (SEQ ID NO: 28) tetrapeptide pharmacophore of Somatostatins) was found to bind to a receptor of interest, the significance of particular hydrogen bonds in its binding, for example between the side chain of Thr and either the carbonyl of the peptide of Trp or the carbonyl of the peptide of Phe, can easily be tested by preparing an analog of the beta-turn mimetic that cannot form these bonds, for example Ala-Phe-Trp-Lys-Ala-Ala (SEQ ID NO: 33).

Or for example, if there multiple conformations and the associated topologies are possible for a constrained peptide, identification and significance of a particular conformation or topology or related structures that are essential for a specific biological activity can be determined by synthesizing different topological isomers of the constrained peptide. For example, five different topological dispositions of the same b-turn forming pharmacophore tetra peptide FWKT (SEQ ID NO: 28) in somatostatin hormones are responsible for activating the different human somatostatin receptors 1-5 and hence induce various responses in the G-protein signal cascade that result in several physiological functions including the regulation of growth hormone stimulation and insulin expression. Specific topological mimics of the constrained b-turn analogues of somatostatin are excellent for selectively inducing the different above mentioned responses in cells (for illustrative examples see *J. Med. Chem.*, 1998, 42:919-929; *J. Med. Chem.*, 1998, 42:1146-1154; *J. Med. Chem.*, 1998, 42:2175-2179; *J. Med. Chem.*, 1998, 42:2679-2685; *J. Med. Chem.*, 1998, 42:2686-2692; *J. Med. Chem.*, 1998, 42:4693-4705; *J. Med. Chem.*, 1998, 51(5):1223-1230; and *J. Med. Chem.*, 2005, 48(21):6643-6652). Similarly, Topological mimics of the specific topological isoforms of the MSH tetrapeptide pharmacophore are good leads for various responses in cells. For examples of MSH analogues, see *Peptides*, 2005, 26(10):1687-1689;

In another aspect of the technology, constrained peptides that are structural analogues of sheet forming peptides with antimicrobial activity can be synthesized. For example, the β-sheet forming cyclic decapeptide homodimer Gramicidin-S has two turns and an antiparallel β-sheet in it and is an excellent antimicrobial peptides. But the natural peptide is digested in a very short time in the human system and hence nonpeptide analogues a of gramicidin-S are sort after. The technology can be used to synthesize several nonpeptide reverse turn/sheet analogues of the gramicidin-S as antimicrobial drug leads.

Synthetic nonpeptide molecules can then be produced based upon information obtained from nuclear magnetic resonance (NMR) to determine binding interactions and bound-state conformations of these structures; and employing molecular modeling to interpret the NMR data and to predict improved synthetic nonpeptide structures.

NMR conformational analysis for small peptide and peptide analog systems in solution is straightforward and well known in the art. For e.g., Bax, *Two-Dimensional Nuclear Magnetic Resonance in Liquids*, D. Reidel Publishing Co., Boston, 1982; Wuthrich, *NMR of Proteins and Nucleic Acids*, Wiley-Interscience, New York, 1986; Ernst et al., *Principles of Nuclear Magnetic Resonance in One and Two Dimensions*, Oxford University Press, New York, 1987.

NMR along with computer-assisted molecular modeling allows the identification of ligand-receptor interactions required for binding. Identifying the interactions required for binding facilitates preparation of synthetic molecules that are capable of similar binding, and therefore of acting as agonists or antagonists. Once a single stable binding conformation is known, the design and preparation of a synthetic therapeutic molecule capable of acting as an agonists or antagonist is thus brought within the ability of one skilled in the art, without requiring undue experimentation.

Thus, in another aspect, the technology provides synthetic therapeutic molecules capable of acting as agonists or antagonists, wherein such molecules are based upon structural features of a conformationally restricted beta-turn mimetic that is capable of binding to the receptor. Particularly likely candidates for the development of such therapeutics include synthetic molecules based upon one or more structural features of a binding conformation of a peptide hormone, lymphokine, growth factor, enzyme inhibitor, or viral binding protein.

The alpha-helix mimetics of this technology have broad utility in a variety of naturally occurring or synthetic peptides and proteins.

In another aspect, the technology provides helical-turns of the type, $3_{10}$-helical, α-helical, π-helical, or larger helical motifs having both variable sizes and bond angles and variable side chain and backbone constituents. The peptides may contain such helical-turn mimetics internally, in one or multiple numbers, or at either end, i.e., the N- or the C-terminal, or for constraining a peptide end-to-end. The sequence of the native peptide being mimicked in the biological system is itself the drug lead and is constrained by this technology without mutation to any of its structural features. Hence, also, the molecular recognition surface of the natural substrate is completely retained.

Such helical-turn mimetics, or peptides containing the same, are conformationally restricted, and as such are useful for the design and synthesis of conformationally restricted peptides that bind to specific protein or enzyme receptors inside or on the surface of cells and hence trigger a biological stimulus. For example, the $^{72}$GQVGRQLAIIGDDINR$^{87}$ (SEQ ID NO: 1) hexadecapeptide representing the BH3 helical domain of the Bak enzyme, binds to the Bcl-xl enzyme, which event is crucial for regulation and irreversible launch of apoptotic activity selectively in cancerous cells (for mechanistic studies see *J. Cell Biol.*, 2005, 168(5):723-734), and which also render the cells sensitive to a variety of apoptotic stimuli, can be constrained into a helical conformation by the technology, resulting in a constrained helical peptide. Helical mimics of the BH3 helical domain $^{72}$GQVGRQLAIIGD-DINR$^{87}$ (SEQ ID NO: 1) hexadecapeptide Bak enzyme have been shown to bind to the bcl-xl enzyme and trigger apoptotic response (*Angew. Chem. Int. Ed.*, 2005, 44:6525-6529); Helical mimics of the BH3 helical domain peptide EDIIRNIAR-HLAQVGDSN$_L$DRSIW (SEQ ID NO: 4) of Bid enzyme have also been shown to bind to the Bcl-xl enzyme and trigger similar apoptotic responses. See *Science*, 2004, 305:1466-1470.

In another example, cell permeable derivatives of the STAT3 $2^{nd}$ helix, directly and specifically bind to STAT3 (and not STAT1) and potently induce apoptotic death in breast cancer cells (not normal breast cells and STAT3 deficient cells). Constrained helical analogues of the helix are good drug candidates and are tools for studying mechanism of STAT transcription factors (A.C.S. *Chem. Biol.*, 2007, 2(12): 799-809). In another aspect, the technology can be used to synthesize the contained helical analogues of the STAT 3-$2^{nd}$ helical peptide.

In another aspect, the technology can be used to synthesize constrained analogues of amphipathic helical peptides. Helical amphipathic peptides can self associate and perturb phospholipids bilayers, leading to functions like membrane fusion, channel formation, translocation of proteins. *J. Cell Sci.*, 1998, 111:2171-2180, several amphipathic helices in toxins form channels in phospholipids bilayers e.g., bee-venom meletin, *E. coli* colicin toxin (*J. Biol. Chem.*, 1995, 270:1048-1056).

In another aspect, the technology can be used to synthesize constrained helical analogues of pore forming helical peptides. For example, a viral helical peptide FGFKDIIRAI-RRIAVPVVSTLF (SEQ ID NO: 13) is the active helical pore-forming domain that deforms and perforates biological membranes. *J. Biol. Chem.*, 2007, 282(28):10774-20784.

In another aspect, the technology can be used to synthesize constrained helical analogues of antimicrobial peptides. For example, Phylloseptins (12-20 a.a.s) exhibit antimicrobial activities against a wide range of pathogenic bacteria and fungi. They form helical structures. The helical arrangement allows them to intercalate into the bilayer interface and to develop antimicrobial activity by membrane permeabilization. *Peptides*, 2008, 29:1633-1644. In another example, a short helical peptide (hSHP-I) has been reported with antimicrobial, anti tumor and immune stimulating activity. PCT-Int. Appl. (2007) PIXXD2 WO 2007142381, AI 20071213.

In another aspect, the technology can be applied for synthesizing constrained helical mimics of helical domains of motifs that recognize and bind to DNA, resulting in engineered switching on or off of gene expression in vivo in cells; inhibition of HIV-1 expression or disruption of the infectious cycle of infection by herpes simplex virus; activating expression of VEGF-A (Vascular endothelial growth factor-A) in monkey and human cell line and animal models; regulation of Zn-finger expression by small molecules. For example, the helical domain peptides of the type $^{-1}$QXXN$^3$XXK$^6$ of Zn-finger motifs bind to a specific triplet nucleic acid sequence in DNA and regulate a number of gene expression related activities. Constrained heptapeptide helical analogues of the helical domain of Zn-finger motifs are known to bind to specific triplet nucleic acid sequences in DNA and regulate similar set of activities, for example, see *J. Mol. Biol.*, 1995, 252:1-5; *Nucl. Acids Res.*, 2005, 33(18):5978-5990; PNAS 1996, 93, 12834-12839. Note: the constrained helical heptapeptide will not require the Zn-binding helical sequence of the Zn-finger peptide motif for its stability.

In another aspect of the technology, constrained RNA-binding helical peptides can be synthesized for regulation of transcription or translation of RNA. The helical conformation of the ARM (Arg rich motif) of HRP-L7, that binds to Rev-response element (RRE) of HIV-1 in vitro, is crucial for the RNA binding activity. *Eur. J. Biochem.*, 1997, 245:549-556. Constrained helical analogues of the ARM (Arg rich motif) of HRP-L7 and other RNA-binding domains (*Biochem. Biophys. Res. Commun.*, 1999, 258:530-536) and the Rev-response element (RRE) of RNA binding protein domains (see *International Reviews of Immunology*, 1999, 18(5-6):429-448) can be synthesized using the technology.

In another aspect, the technology provides the constraining of peptide sequences made of either natural or unnatural amino acids.

Table 1 lists illustrative peptides that can be modified with one or more hydrogen bond mimics disclosed herein to provide compounds of the technology. Table 1 also includes the biological targets that such compounds would act upon.

TABLE 1

| Seq ID. No. | Peptide | Target Domain/Cell | Therapeutic target | Reference |
|---|---|---|---|---|
| | | Helical | | |
| 1. | $^{72}$GQVGRQLAIIGDDINR$^{87}$ | Bcl-xL/Bak (BH3 domain) - | Cancer cells nti cancer | J. Cell Biol., 2005, 168(5): 723-734; Science, 1997, 275: 983-986 |
| 2. | GQVGRQLAII | | | |
| 3. | GRQLAIIGDDINR | | | |
| 4. | EDIIRNIARHLAQVGDSN$_L$DRSIW N$_L$ = Norleucine | Bcl-xL/Bid (BH3 domain) - | Cancer cells, nti cancer | Science, 2004, 305: 1466-1470 |
| | Zinc finger recognition helices- | Specific triplet base recognition in DNA | | Proteins, 1992, 12: 101-104; Proteins, 1992, 12: 272 (erratum) |
| 5 | $^{-1}$QSSNLQK$^6$ | DNA | | J. Mol. Biol., 1995, 252, : 1-5 |
| 6 | $^{-1}$QSSDLQK$^6$ | DNA | Gene off/on, repair, | |
| 7 | Met repressor VKKITVSIXXXXISVTIKKV (X-any amino acid) | DNA/RNA | Gene (DNA/RNA) | Ann. New York Acad. Sci., 1994, 726: 105-117; SEQ ID NO: 26 in Table 1 of U.S. Pat. No. 7,202,332 B2 |
| 8 | Arc repressor PQFNLRTXXTRLNFQP (X = any amino acid) | DNA | Gene (DNA/RNA) | Ann. Rev. Biochem,. 1984, 52: 293-321 (general review); Specific example in: SEQ ID No: 27 in Table 1 of U.S. Pat. No. 7,202,332 B2- Methods for preparing internally constrained peptides and peptidomimetics - SEQ ID NO: 27 |
| | Human ribosomal protein L7 (HRP-L7) | | RRE (rev response element) RNA | (For review see the following: Int. Rev. Immun., 1999, 18(5-6): 429-448 |
| 9 | ELKIKRLRKKFAQMLRKARRK (= ARM - Arg rich motif) (of HRP-L7) | RRE of HIV-1 | Rev response response of HIV-1 | Eu. J. Biochem., 1997, 245: 549-556 |
| 10 | TRQARRNRRRRWRERQR | | | |
| | STAT3 - 2$^{nd}$ helix | | Cell-permeable | 5 |
| 11 | DTRYLEQLHKLYS | Cell membrane | Apoptotic peptides | A. C. S. Chem. Biol., 2007, 2(12): 799-809 |
| | Amphipathic helical peptides | | Antimicrobial | |

TABLE 1-continued

| Seq ID. No. | Peptide | Target Domain/Cell | Therapeutic target | Reference |
|---|---|---|---|---|
| 12 38 39 | FLSLIPHAINAVSAIAKHN-NH$_2$ (c-terminal amide) FLSLIPHAINAVSTLVHHF-NH2 FLSLIPHAINAVSTLANHG-NH$_2$ | Pathogenic bacteria or fungi | Phylloseptins - self association & membrane permeablization | Peptides, 2008, 29: 1633-1644 |
| 13 | FGFKDIIRAIRRIAVPVVSTLF (Pep-22) | Deformation and preforation of biological membranes | Viral peptide | J. Biol. Chem. 2007, 282(28): 10774-10784 |
| 14 | WDFFPAGDCFRKQYEDQLS (CTT19S) | Ryanodine receptor Ca$^{2+}$ release channel | Modulation of Homer | Int. J. Cell Biol., 2006, 38(10): 1700-1715 |
| 15 | KWKVFKKIEKVFSNIRDGI (CecropinA analogue) | Cell membrane | anticancer | Inflammation, 2004, 28(6): 337-343 |
|  | Short helical peptide-1 |  | Anti viral, tumor, Immune stimulating agent, | PCT-Int. Appl. (2007) PIXXD2 WO2007142381, AI 20071213 |
| 16 | SQETFSDLWKLLPENNV |  | P53/MDM2 | Mini Rev. Med. Chem., 2003, (3): 257-270 |
| 17 | QQLEEDLKGYLDWITQ |  | Calcium ion channel (AID) | SEQ ID NO: 15 in Table 1 of U.S. Pat. No. 7,202,332 |
| 18 | RIARLEEKVK |  | Jun/Fos | SEQ ID NO: 16 in Table 1 of U.S. Pat. No. 7,202,332 B2 |
| 19 | Hex-RIARLEEKVK |  | Jun/Fos | SEQ ID NO: 17 in Table 1 of U.S. Pat. No. 7,202,332 B2 |
| 20 | ELASTANALRE |  | Jun/Fos | SEQ ID NO: 18 in Table 1 of U.S. Pat. No. 7,202,332 B2 |
| 21 | QVAQLKQKVA |  | Jun/Fos | SEQ ID NO: 19 in Table 1 of U.S. Pat. No. 7,202,332 B2 |
| 22 | ELASTANALREQVAQLKQKVAAY |  | Jun/Fos | SEQ ID NO: 20 in Table 1 of U.S. Pat. No. 7,202,332 B2 |
| 23 | RIARLEEKVKTLKAQN |  | Jun/Fos | SEQ ID NO: 21 in Table 1 of U.S. Pat. No. 7,202,332 B2 |
| 24 | EVAQLEDEKSALQ |  | Jun/Fos | SEQ ID NO: 22 in Table 1 of U.S. Pat. No. 7,202,332 B2 |
| 25 | WAAWDREINNYT |  | HIV gp41 | SEQ ID NO: 23 in Table 1 of U.S. Pat. No. 7,202,332 B2 |
| 26 | WAAWDREIN |  | HIV gp41 | SEQ ID NO: 24 in Table 1 of U.S. Pat. No. 7,202,332 B2 |
| 27 | GRKKRRNRRR (carrier peptides or cell penetrating peptides) |  | HIV TAR RNA | Proc. Natl. Acad. Sci. USA, 1994, 91: 8248-8252 |
|  | N-terminal helical domain (22 a.a.) |  | MCRs - melanocortin receptors 1-5 | J. Med. Chem., 1998, 41(14): 2614-2620 |
| | β-turn/β-hairpin/β-sheet | | | |
| | Somatostatin | | | |
| 28 | FWKT | Human somatostatin receptor | G-protein signal cascade | (Examples of analogues containing FWKT (SEQ ID NO: 28)) J. Med. Chem., 1998, 42: 919-929; 1146-1154; 2175-2179; 2679-2685; 2686-2692; 4693-4705; J. Med. Chem., 2005, 48(21): 6643-6652; J. Med. Chem., 2008, 51(5): 1223-1230 |

TABLE 1-continued

| Seq ID. No. | Peptide | Target Domain/Cell | Therapeutic target | Reference |
|---|---|---|---|---|
| 29 | F$^D$WKT | Human somatostatin receptor | G-protein cascade | PNAS USA 1998, 95, 1794-1799; PNAS USA 1998, 95, 10836-10841; Cancer Res. 1998, 58, 4132-4137; J. Am. Chem. Soc. 1998, 120, 1368-1373; J. Med. Chem. 1998, 42-pages-919-929; 1146-1154; 2175-2179; 2679-2685; 2686-2692; 4693-4705; J. Med. Chem. 2008, 51(5), 1223-1230; J. Med. Chem. 2005, 48(21), 6643-6652 |
|  | Gramidicin-S | Cell membrane | Antimicrobial | For a few analogues of GS see: J. Med. Chem. (ASAP) Jan. 8, 2009, DOI: 10, 1021/jm800886n; Biochem. 1987, 26(21), 6604-6612; |
| 30 | Analogues of $_{cyclo}$[$^D$FPVOL]$_2$ | Cell membrane | Antimicrobial | Biophysical Journal, 2008, 95(7): 3306-3321; Peptide Science, 2007, 44: 255-256; Journal of Antibiotics, 2006, 59(6): 370-372 |
| 34 | NPNA-Circumsporozite surface protein of the malarial parasite-P. falciparum-β-turn |  | T-cell epitope in multiple antigen peptide | J. Am. Chem. Soc., 1998, 120: 7439-7449 |
| 35 | HFRW-pharmacophores in MSH and ACTH (G-protein coupled receptors) | MCHs-hormones for melanocortin receptors 1-5 | Pigmentation, anti obesity, cardiovascular regulation | Peptides, 2005, 26(10): 1687-1689 |
|  | Met repressor-β-sheet peptides (in E. coli) | dsDNA | DNA recognition and Gene regulation | Nature, 1992, 359(6394): 431-433; Nature, 1992, 359(6394): 387-393; J. Nol. Biol., 1992, 226(4): 1257-1270 |
| 31 36 | MpaYFQNCP$^D$RG-NH$_2$ (Desmopressin)-Int. J. Pept. 561-574-a drug analogue of Vasopressin CFYQNCPRG-NH$_2$ (a neurohypophyseal peptide hormone)-J. Am. Chem. Soc. 1953, 75, 4880 ± 4881 Note the modified sequence. | γ-turn | Antidiuretic, treatment of mild haemophilia A, von Willebrand's disease and thrombocyte disfunction | For example of an analogue-Chem. Eur. J., 1999, 5(8): 2241-2253 |
| 37 | GPG(R/Q)PGQ-β-hairpin; V3 loop of gp120 (HIV-1) PND (principle Neutralizing domain) |  | HIV-1 | Biochemistry, 2006, 45(13): 4284-4294 |
| 40 | SQEPPISLDLTFHLLREMLEMAKAEQEAE QAALNRLLLEEA (N-terminal helical domain of Corticotropin releasing factor) |  | MCRs-melanocortin receptors 1-5 | J. Med. Chem., 1998, 41(14): 2614-2620 |

In a further aspect of this technology, methods for screening compounds disclosed herein for bioactivity and isolating bioactive compounds are disclosed. Compounds of the present technology may be screened for bioactivity by a variety of techniques and methods. Generally, the screening assay may be performed by (1) contacting a compound or a library (i.e., collection or group) of such compounds with a biological target of interest, such as a receptor, and allowing binding to occur between the compound or members of the library and the target, and (2) detecting the binding event by an appropriate assay, such as by the colorimetric assay disclosed by Lam et al. (*Nature*, 1991, 354:82-84) or Griminski et al. (*Biotechnology*, 1994, 12:1008-1011) (both of which are incorporated herein by reference). In one embodiment, the library members are in solution and the target is immobilized on a solid phase. Alternatively, the library may be immobilized on a solid phase and may be probed by contacting it with the target in solution.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

EXAMPLES

The present technology is further illustrated by the following examples, which should not be construed as limiting in any way.

The following abbreviations are used throughout the present disclosure with respect to chemical terminology:
ACN: Acetonitrile
AcOH: Acetic acid
Aib: α-aminoisobutyric acid
Ala Alanine
Boc: N-tert-Butoxycarbonyl
Bop Benzotriazole-1-yl-oxy-tris-(dimethylamino)-phosphonium hexafluorophosphate
Bn: Benzyl
Bu: Butyl
Cbz or Z: Benzoyloxycarbonyl
DCC: Dicyclohexylcarbodiimide
DCM Dichloromethane
DEAD Diethyl azodicarboxylate
DIAD Diisopropyl azodicarboxylate
DIEA Diisopropylethylamine
DIPEA Diisopropyl ethylamine
DMAP: N,N-dimethyl-4-aminopyridine
DMF: N,N-Dimethylformamide
ECF Ethyl chloroformate
Et: Ethyl
EtOAc: Ethyl acetate
EtOH: Ethanol
Fmoc: Fluorenyl-methoxy-carbonyl
HATU: O-(7-Azabenzotriazole-1-yl)-N,N,N'N'-tetramethyluronium hexafluorophosphate
HBTU: O-(1H-Benzotriazole-1-yl)-N,N,N',N'-tetramethyluronium hexafluorophosphate
HOBt: 1-Hydroxybenzotriazole
HOSu Hydroxy-succinimide
HPLC: High Pressure Liquid Chromatography
IPA: Iso-propyl alcohol
$K_2CO_3$ Potassium carbonate
LiOH Lithium hydroxide
Me: Methyl
MS (ESI): Electrospray ionization mass spectrometry
$Na_2CO_3$ Sodium carbonate
$NaHCO_3$ Sodium bicarbonate
Nosyl (Ns) 4-nitrobenzenesulfonyl
NMM: N-Methylmorpholine
NMR: Nuclear Magnetic Resonance
Ph: Phenyl
$PPh_3$ Triphenyl phosphine
PhSH Thiophenol
r.t. Room temperature
SLC: Side-chain linked
SPPS: Solid phase peptide synthesis
tBu: tert-butyl
TFA: Trifluoroacetic acid
THF: Tetrahydrofuran
TLC Thin layer chromatography Materials and Methods:

All solvents were dried prior to use according to literature methods (as in: D. D. Perrin and W. L. F. Armarego, *Purification of Laboratory Chemicals*, Pergamon Press, Oxford, 3rd Ed., 1988). Unless otherwise mentioned, all reagents were purchased from different sources, from either of Aldrich, SD Fine chemicals, Spectrochem, or Kemphasol. Analytical TLC was performed on silica gel 60-F254 (Merck) with detection by fluorescence, or $I_2$ and/or by charring following immersion in 5% solution of $H_2SO_4$/EtOH, or in 5% solution of ninhydrin in EtOH. Silica gel (100-200 mesh) was used for column chromatography. Melting points are uncorrected. $^1H$ and $^{13}C$ NMR spectra were recorded either on a spectrometer operating at 300 and 75 MHz, respectively, or a spectrometer operating at 400 and 100 MHz, respectively (JEOL 300 MHz-JNM-LA300, or Bruker AVANCE 400 MHz or Varian (AV400) 400 MHz spectrometers were used). Tetramethylsilane or residual solvent signal formed the internal reference for the NMR spectra. The following abbreviations were used to denote the signal multiplicities: s, singlet; d, doublet; t, triplet; m, multiplet; dd, doublet of doublet; br, broad; bs, broad singlet; H, proton; Hz, Hertz. FTIR spectra were recorded in one of either a Perkin-Elmer IR spectrometer (PE Spectrum BX or PE Spectrum GX) or a JASCO IR spectrometer (FTIR-410). Mass spectra were recorded either on a Shimadzu GCMS-GC-17A or on a Waters Q-TOF Micromass Spectrometer.

Example 1

Solution Phase Synthesis of Boc-Ala-Ala-NH-$(CH_2)_3$—Br

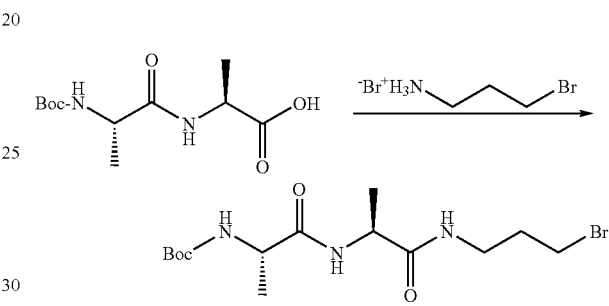

Step I: Synthesis of 3-bromopropan-1-aminium bromide

A mixture of 3-amino 1-propyl alcohol (1 ml, 13.3 mmol) and 48% HBr (10 ml, 40 mmol) were placed in a round-bottom flask and refluxed for 15 h. Then water and HBr were distilled out of the mixture under vacuum. The mixture was further dried under vacuum through a $KOH/CaCl_2$ tower to give the desired product (2.95 gm, 100%) as a brown solid (m.p. 172° C.).

IR (KBr) ν: 3450, 3176, 3011, 2916, 1579, 1503, 1237, 1113, 1037, 950 $cm^{-1}$. $^1H$ NMR (400 MHz, $CDCl_3$) δ ppm: 3.4 (t, J=6.3 Hz, 2H), 3.01 (t, J=7.5 Hz, 2H), 2.08 (t, J=6.9 Hz, 2H). HRMS (EI) m/z calculated for $C_3H_9Br_2N$: 216.9102 found: 137.9911 $[M-Br]^+$.

Step II: Synthesis of Boc-Ala-OH

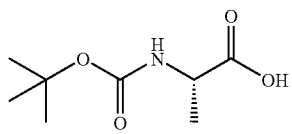

$K_2CO_3$ (3.1 g, 22.46 mmol) and alanine (1 g, 11.23 mmol) were dissolved in minimum amount of water (8 ml) maintained at 0° C. A solution of ditertiarybutyl dicarbonate (2.57 g, 11.8 mmol) in THF (4 ml) was slowly added to the aqueous solution and stirred. Additional amounts of K₂CO₃ were added, if needed, to the mixture in order to maintain the pH of the solution between 10-12. After stirring at 0° C. for 30 minutes, the mixture was warmed to r.t. After eight hours THF was removed under reduced pressure and the aqueous portion was washed with diethyl ether, acidified (to pH 2) with citric acid and extracted with ethyl acetate (3×10 ml). The organic layer was dried over Na₂SO₄ and concentrated under vacuum to give a white solid (m.p. 77-79° C.) in quantitative yields (2.12 g).

HRMS (EI) m/z calculated for $C_8H_{15}NNaO_4$—212.0899, Found—212.0899.

Step III: Synthesis of ClH.AlaOMe

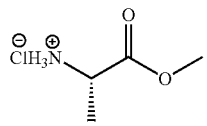

To a suspension of alanine (650 mg, 7.29 mmol) in methanol (8 ml) at 0° C. was added SOCl₂ (0.54 ml, 8.02 mmol) drop wise at a rate so that the temperature of the reaction mixture does not exceed 4° C. 5 min after complete addition, the ice bath was removed and the reaction mixture was stirred at 25° C. for 8 hrs, followed by removal of the solvent under vacuum through a KOH/CaCl₂ tower to get the desired methyl alaninate hydrochloride as white hygroscopic solid in quantitative yield (1.01 g).

IR (NaCl, neat) ν: 3414.6, 2959.2, 1747.3, 1616.3, 1515.7, 1459, 1252, 1215.9, 1118 cm⁻¹; LRMS (EI) m/z calculated for $C_4H_9NO_2$-103.0633, Found—104 [M+H]⁺ (100%); 207 [2M+H]⁺ (100%).

Step IV: Synthesis of Boc-Ala-Ala-OMe

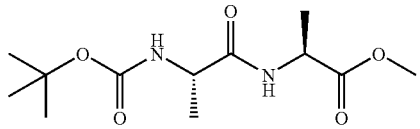 [SMILES: COC(=O)[C@H](C)NC(=O)[C@H](C)NC(=O)OC(C)(C)C]

To a cold (−15° C.) solution of Boc-Ala-OH (1.034 g, 5.47 mmol) and NMM (901 μl, 8.20 mmols) in THF (15 ml) was added ECF (538 μl, 5.63 mmols) under N₂ atmosphere and vigorously stirred. After 2 min of stirring, a solution of methyl alaninate hydrochloride (840 mg, 6.01 mmols) in a mixture of solvents THF:DMF (4 mL: 3 mL) was added to the reaction mixture followed by NMM (1.5 ml, 13.67 mmols) and stirred. After 10 min the mixture was warmed to 25° C. and stirred for further 8 h. THF was removed under reduced pressure and the resulting viscous solution was diluted with water (10 mL) and thoroughly extracted with ethyl acetate. The combined organic extracts were washed with saturated citric acid (10 mL), saturated NaHCO₃ (10 mL) and dried over by Na₂SO₄ and concentrated under reduced pressure to give a residue, which was purified by silica gel flash column chromatograph (EtOAc:Hexane—3:17) to give the desired product as a solid (m.p. 107-108° C.) in good yields (1.48 g, 98.6%). (TLC: EtOAc:Hexanes 7:3—$R_f$—0.55).

IR (NaCl, neat) ν: 3315, 2982, 2938, 1746, 1693, 1668, 1533, 1249, 1213, 1167, 1070, 1054 cm⁻¹. ¹H NMR (400 MHz, CDCl₃) δ ppm: 6.69 (bs, 1H), 5.05 (bs, 1H), 4.56 (quint, J=7.2 Hz, 1H), 4.20-4.10 (m, 1H), 3.74 (s, 3H), 1.44 (s, 9H), 1.39 (d, J=7.2 Hz, 3H), 1.35 (d, J=7.1 Hz, 3H). ¹³C NMR (100 MHz, CDCl₃) δ ppm: 173.2 (2C), 172.2, 80.1, 52.5, 49.9, 48.0, 28.3, 18.3, 18.2. HRMS (EI) m/z calculated for C12H22N2NaO5: 297.1426, Found: 297.1432[M+Na]⁺.

Step V: Synthesis of Boc-Ala-Ala-OH

To a solution of LiOH.H₂O (275 mg, 6.56 mmol) in a mixture of solvents MeOH: H₂O (10.9 mL: 3.6 mL) was added Boc-Ala-Ala-OMe (1.2 g, 4.38 mmol) and stirred for 4 hours at r.t. The solution was acidified to pH 2 with saturated aqueous solution of citric acid and the mixture was extracted with EtOAc (3×20 mL). The organic layer was dried over Na₂SO₄ and concentrated under vacuum to give the desired product Boc-Ala-Ala-OH as a highly viscous and hygroscopic oil in quantitative yields (1.14 g). The product was taken for further reactions directly without any purification.

Step VI: Synthesis of Boc-Ala-Ala-NH—(CH₂)₃—Br

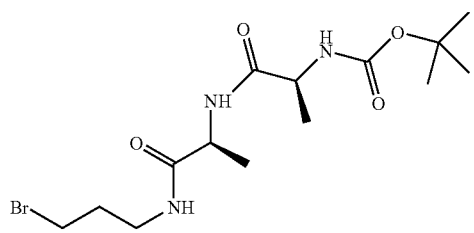 [SMILES: C[C@H](NC(=O)OC(C)(C)C)C(=O)N[C@@H](C)C(=O)NCCCBr]

To a cold (−15° C.) solution of Boc-Ala-Ala-OH (908 mg, 3.5 mmol) and NMM (570 μl, 5.23 mmols) in THF (15 ml) was added ECF (341 μl, 3.6 mmols) under N₂ atmosphere and vigorously stirred. After 2 min of stirring, a solution of 1-amino-3-propylbromide hydrobromide (976 mg, 4.90 mmols) in a mixture of THF:DMF (4 mL: 3 mL) was added to the mixture followed by NMM (951 μl, 8.73 mmols) and stirred. After 10 min the mixture was warmed to 25° C. and stirred for further 8 h. THF was removed under reduced pressure and the resulting viscous solution was diluted with water (10 mL) and thoroughly extracted with ethyl acetate. The combined organic extracts were washed with 5 ml saturated citric acid, 5 ml saturated NaHCO₃ and dried over by Na₂SO₄ and concentrated to give a residue, which was purified by silica gel flash column chromatograph (EtOAc:Hexane—3:7) to give the desired product as a solid (m.p. 146° C.) in good yields (1.022 g, 78%). (TLC:EtOAc—$R_f$—0.39).

IR (NaCl, neat) ν: 3304, 2978, 2927, 1697, 1640, 1538, 1447, 1365, 1252, 1167, 1050 cm⁻¹. ¹H NMR (300 MHz, CDCl₃) δ ppm: 6.8 (bs, 1H), 6.66 (d, J=6.9 Hz, 1H), 5.0 (d, J=5.4 Hz, 1H), 4.44 (qui, J=7.2 Hz, 1H), 4.10 (qui, J=6.9 Hz, 1H), 3.5-3.28 (m, 4H), 2.08 (qui, J=6.6 Hz, 2H), 1.46 (s, 9H), 1.39 (d, J=6.9 Hz, 3H), 1.37 (d, J=6.9 Hz, 3H). ¹³C NMR (75 MHz, CDCl₃) δ ppm: 173, 172, 155, 81, 50, 49, 38, 32, 30, 28, 17. HRMS (EI) m/z calculated for $C_{14}H_{26}BrN_3O_4$: 379.1107, Found: 402.100 [M+Na]⁺.

Example 2

Synthesis of Nosyl-Ala-Ala-NH-(CH$_2$)$_3$—Br

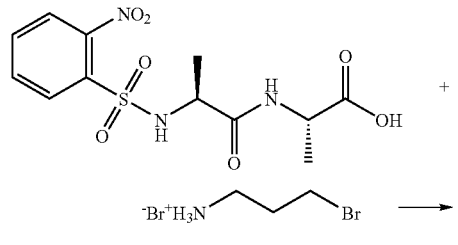

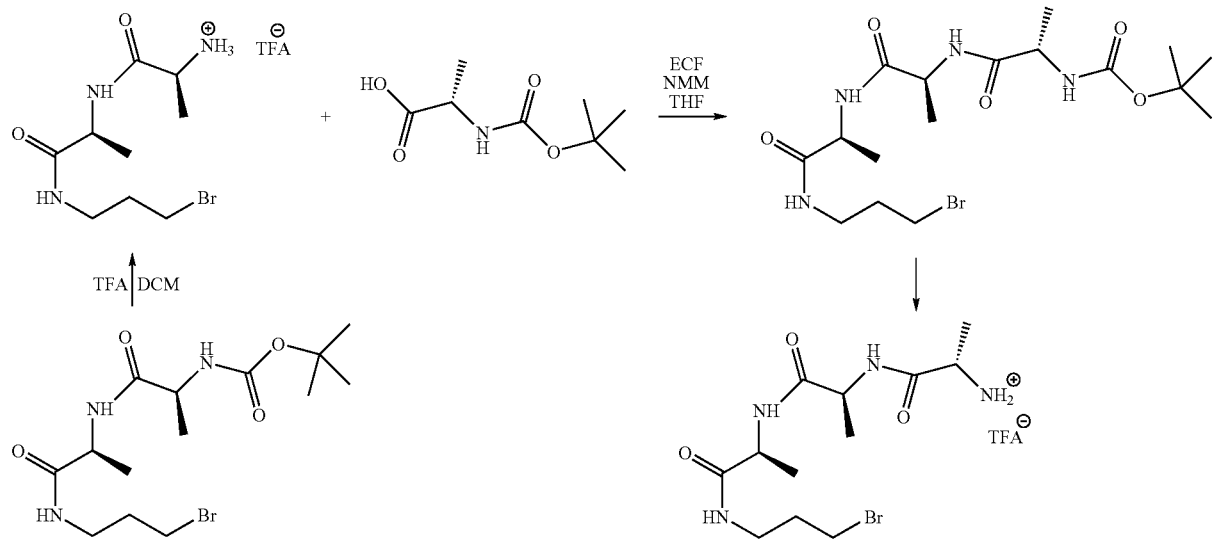

-continued

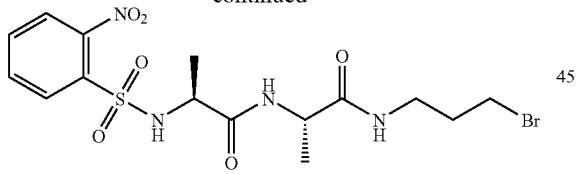

To a stirring cooled (−15° C.) solution of N-Nosyl-dialaninyl acid (650 mg, 1.88 mmol) and NMM (304 μl, 2.86 mmol), in THF (10 mL) under nitrogen atmosphere was added ethyl chloroformate (186 μl, 1.97 mmol) and stirred. After 2 minutes, a solution of Bromo 1-ammonium N-propyl-3-bromide (3.75 mmol) in DMF:THF (1:2) solvent mixture (4.5 mL) was added. The mixture was warmed to room temperature and stirred for a further 12 h. THF was removed under reduced pressure and the resulting residue was diluted with water and extracted with ethyl acetate. The organic extracts were washed with saturated aqueous citric acid solution followed by saturated aqueous NaHCO$_3$, dried over anhydrous sodium sulfate and concentrated under vacuum to yield a residue. The residue was purified by silica gel column chromatography (eluting solvent:EtOAc:Hexanes—1:2) to give the desired compound (392 mg, 45%) as a solid (m.p. 131° C.). TLC (EtOAc; R$_f$—0.44).

IR (KBr) ν: 3399.9, 3259.5, 3154, 2872, 1676, 1637.3, 1543, 1446, 1374, 1323, 1169, 1153 cm$^{-1}$. $^1$H NMR (300 MHz CDCl$_3$) δ ppm: 8.16-8.19 (m, 1H), 7.94-7.97 (m, 1H), 7.78-7.84 (m, 2H), 7.06 (d, J=7.8 Hz, 1H), 6.82 (d, J=5.1 Hz, 1H), 4.42 (qui, J=7.2 Hz, 1H), 3.38-3.46 (m, 4H), 2.05-2.16 (m, 2H), 1.41 (d, J=7.2 Hz, 3H), 1.37 (d, J=7.2 Hz, 3H). $^{13}$C NMR (75 MHz CDCl$_3$) δ ppm: 171.90, 171.04, 134.34, 133.14, 131.56, 125.82, 53.76, 49.30, 38.11, 32.03, 30.68, 19.01, 17.93. HRMS (EI) m/z calculated for C$_{15}$H$_{21}$BrN$_4$O$_6$S—464.0365, observed—487.0267 [M+Na]$^+$.

Example 3

Solution Phase Synthesis of TFA.Ala-Ala-Ala-NH—(CH$_2$)$_3$—Br

Step I: Synthesis of TFA.Ala-Ala-NH—(CH$_2$)$_3$—Br

To an ice cold solution of Boc-Ala-Ala-NH-(CH$_2$)$_3$—Br (300 mg, 0.79 mmol) in DCM (18 mL) was added TFA acid (2 mL) and stirred for 3 h when TLC indicated complete consumption of the starting carbamate. The solvent was removed and the residue was concentrated under vacuum to yield the desired TFA salt in good yield (311 mg, 100%), which was taken up directly for coupling in the next reaction. TLC (MeOH: DCM—1:4; R$_f$—0.34). M.p., 142° C.

IR (KBr) ν: 3319, 3064 (br), 2731.6, 2616.7, 2518.7, 1690.9, 1652.2, 1535.5, 1509.4, 1203.2, 1179, 1141.4, 844.3 cm$^{-1}$. $^1$H NMR (300 MHz, D$_2$O) δ ppm: 4.11 (q, J=7.2 Hz, 1H), 3.92 (q, J=6.9 Hz, 1H), 3.31 (t, J=6.6 Hz, 1H), 3.12 (m, 1H), 1.89 (qui, J=6.6 Hz, 1H), 1.37 (d, J=7.2 Hz, 3H), 1.22 (d, J=7.2 Hz, 3H). $^{13}$C NMR (300 MHz, CDCl$_3$) δ ppm: 176, 172.9, 51.6, 50.6, 39.3, 32.87, 23.7, 18.5, 18.1. LRMS (EI)

m/z calculated 279.0582, found 280 [M+H]$^+$, 302 [M+Na]$^+$, 304 [M+Na]$^+$(Br$^{81}$), 138, 140 [M−3H]$^{2+}$.

Step II: Synthesis of Boc-Ala-Ala-Ala-NH—(CH$_2$)$_3$—Br

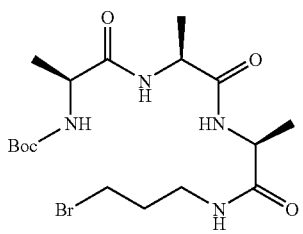 [SMILES: C[C@H](NC(=O)OC(C)(C)C)C(=O)N[C@@H](C)C(=O)N[C@@H](C)C(=O)NCCCBr]

To a cold (−15° C.) solution of Boc-Ala-OH (118 mg, 0.63 mmol) and NMM (103 μl, 1.03 mmol) in THF (8 mL) was added ECF (61 μl, 0.64 mmol) and stirred vigorously. After 2 min. a solution of the TFA salt of Ala-Ala-NH(CH$_2$)$_3$—Br (270 mg, 0.69 mmol) in a mixture of THF:DMF (4 mL: 2 mL) was added to it followed by NMM (170 μL, 1.7 mmol) and stirred for further 30 minutes. The mixture was warmed to r.t. and stirred for 6 h. The solvent was removed under reduced pressure to give a residue which was diluted with EtOAc and washed with saturated citric acid, saturated NaHCO$_3$ and the organic layer was dried over Na$_2$SO$_4$ and concentrated under vacuum to give a residue, which was purified by silica gel flash column chromatography (EtOAc:Hexanes—9:1) to give the desired product as a solid (m.p.—decomposed at 192° C.) in moderate yields (137 mg, 54%). TLC (MeOH:DCM—1:9; R$_f$—0.44).

IR (NaCl, neat) ν: 3432, 3275, 2977, 2929, 1661, 1634, 1535, 1366, 1251, 1166 cm$^{-1}$. $^1$H NMR (300 MHz, CDCl$_3$) δ ppm: 7.24 (bs, 1H), 6.89 (bs, 1H), 6.55 (bs, 1H), 5.02 (s, 1H), 4.45 (q, J=7.5 Hz, 1H), 4.26 (q, J=6.3 Hz, 1H), 3.45-3.29 (m, 4H), 2.10 (q, J=6.9 Hz, 2H), 1.43 (s, 9H), 1.42-1.34 (m, 9H). HRMS (EI) m/z calculated for C$_{17}$H$_{31}$BrN$_4$O$_5$: 450.1478, Found: 473.1378 [M+Na]$^+$, 475.1359 [M+2+Na]$^+$.

Step III: Synthesis of TFA.Ala-Ala-Ala-NH—(CH$_2$)$_3$—Br

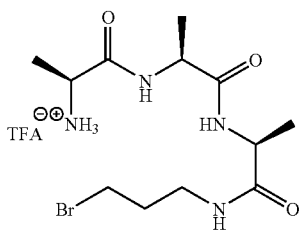 [SMILES: "TFA" ; C[C@H]([NH3+])C(=O)N[C@@H](C)C(=O)N[C@@H](C)C(=O)NCCCBr]

The desired compound (TFA.(Ala)$_3$-NH—(CH$_2$)$_3$—Br) was synthesized by the general procedure for Boc-deprotection (described earlier) of the corresponding Boc-protected peptide precursor. A typical experiment at 65 μmol scale was complete in 3.5 h and yielded the desired product (100%) without any purification after removal of solvent under high vacuum. The resulting residue was taken up directly for coupling in the next step. TLC (MeOH:DCM 1:4; R$_f$—0.53).

$^1$H NMR (300 MHz, CDCl$_3$) δ ppm: 4.18 (q, J=7.2 Hz, 1H), 4.04 (q, J=7.2 Hz, 1H), 3.92 (q, J=7.2 Hz, 1H), 3.30 (t, J=6.6 Hz, 2H), 3.20 (m, 2H), 1.88 (quin, J=6.3 Hz, 2H), 1.36 (d, J=7.2 Hz, 3H), 1.22 (t, J=6.9 Hz, 6H). IR (Heptane Gell) ν: 2992, 2885, 2810, 1696, 1529, 1445, 1337, 1205, 968 cm$^{-1}$.

Example 4

Alternative Solution Phase Synthesis of Boc-Ala-Ala-NH—(CH$_2$)$_3$—Br and Boc-Ala-Ala-Ala-NH—(CH$_2$)$_3$—Br

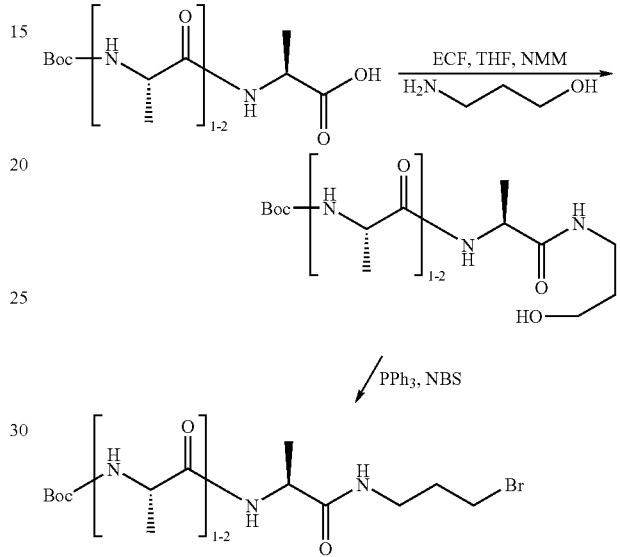

Step I: Synthesis of Boc-Ala-Ala-NH—(CH$_2$)$_3$—OH and Boc-Ala-Ala-Ala-NH—(CH$_2$)$_3$—OH A. Synthesis of Boc-Ala-Ala-NH—(CH$_2$)$_3$—OH To a vigorously stirring solution of Boc-(Ala)$_2$-OH (1.55 gm, 5.96 mmol) and NMM (0.98 mL, 8.9 mmol) in THF (15 mL) cooled to −15° C. was added under an atmosphere of N$_2$ ethyl chloroformate (ECF) (587 μL, 6.14 mmol). After stirring for 2 min, a solution of H$_2$N(CH$_2$)$_3$OH (546 uL, 7.2 mmol) in THF (5 mL) was added to the mixture followed by NMM (1.64 mL, 14.9 mmol) and the mixture was warmed to r.t. and stirred until silica gel TLC indicated complete consumption of the starting acid (eluting solvent-MeOH:DCM—1:10, R$_f$—0.5) (~8 h). The solvent was evaporated, and the residue was diluted with EtOAc and washed with brine, water, saturated solutions of citric acid and NaHCO$_3$, and the organic layer was dried using NaHSO$_4$, and the solvent was removed under vacuum to yield a residue which was purified using silica gel flash column chromatography—Hexanes:EtOAc—1:4; to give the desired product in 84% yield (1.59 g) as a solid, m.p.—142° C.

IR (KBr) ν: 3310, 2979, 2937.6, 2880, 1694, 1660, 1537.6, 1452.8, 1368, 1254, 1168, 1069, 1050 cm$^{-1}$. $^1$HNMR (400 MHz, CDCl$_3$) δ ppm: 7.10 (b, 1H), 6.89 (d, J=6.4 Hz, 1H), 5.21 (d, J=5.6 Hz, H), 4.46 (quin, J=7.2 Hz, 1H), 4.12 (b, 1H), 3.61 (b, 2H), 3.40 (m, 2H), 2.00 (b, 1H), 1.68 (qui, J=5.6 Hz, 2H), 1.44 (s, 9H), 1.38 (d, J=7.2 Hz, 3H), 1.16 (d, J=7.2 Hz, 3H). $^{13}$C NMR (100 MHz, CDCl$_3$) δ ppm: 173, 172.7, 80.72, 59.15, 50.8, 48.98, 36.12, 32, 28.25, 18.31, 17.99. HRMS (EI) m/z calculated for $C_{14}H_{27}N_3O_5$—317.1951, Found—330.1848 [M+Na]$^+$, 240.1327 [M-Boc]$^+$.

B. Synthesis of Boc-Ala-Ala-Ala-NH—(CH$_2$)$_3$—OH

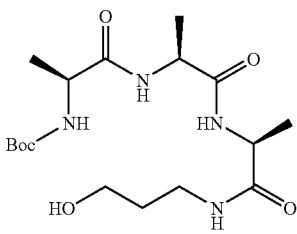 [SMILES: C[C@H](NC(=O)OC(C)(C)C)C(=O)N[C@@H](C)C(=O)N[C@@H](C)C(=O)NCCCO]

The desired compound was synthesized by the procedure of Example 4 using Boc-Ala-Ala-Ala-OH and H$_2$N—(CH$_2$)$_3$—OH except that the solvent was a mixture of THF and DMF (8 h). In a typical reaction of 4.59 mmol scale, the desired product was obtained in good yields, (1.401 gm, 79%) as a solid (m.p.—201° C.) after purification by silica gel flash column chromatography (MeOH:EtOAc—1:25). TLC (MeOH:DCM—1: 3; R$_f$—0.53).

IR (KBr) v: 3340, 2986, 2858, 1692, 1532, 1468, 1074 cm$^{-1}$. $^1$H NMR (400 MHz, D$_2$O) δ ppm: 4.2-4.03 (m, 2H), 3.87 (m, 1H), 3.43 (t, J=6.4 Hz, 2H), 3.10 (m, 2H), 1.56 (q, J=6.8 Hz, 2H), 1.24 (s, 9H), 1.22-1.19 (m, 6H), 1.14 (d, J=6.8 Hz, 3H). $^{13}$C NMR (75 MHz, CDCl$_3$) δ ppm: 174.74, 81.48, 58.95, 50.55, 49.9, 49.2, 36.10, 30.75, 27.5, 16.53, 16.46, 16.19. HRMS (EI) m/z calculated for $C_{11}H_{19}BrF_3N_3O_4$—393.0511, Found—411.2200 [M+Na]$^+$, 427.1905 [M+K]$^+$.

Step II: Synthesis of Boc-Ala-Ala-NH—(CH$_2$)$_3$—Br and Boc-Ala-(Ala)$_2$-NH—(CH$_2$)$_3$—Br A. Synthesis of Boc-Ala-Ala-NH—(CH$_2$)$_3$—Br To a solution of Boc-Ala-Ala-NH—(CH$_2$)$_3$—OH (1.2 gm, 3.78 mmol) and PPh$_3$ (1.98 gm, 7.56 mmol) in THF (15 mL) at −15° C. was added a solution of NBS (802 mg, 6.80 mmol) in THF (5 mL) and stirred until TLC (EtOAc—R$_f$—0.37) indicated complete consumption of the starting amino alcohol (50 min). The solvent was evaporated under vacuum and the residue was diluted with ethyl acetate and washed with water. The organic layer was dried over Na$_2$SO$_4$ and concentrated to give a residue that was purified by silica gel flash column chromatography—EtOAc:Hexanes-3:10, to yield the desired bromide as a solid (m.p. 146° C.) in 81% yield (1.16 gm).

IR (NaCl, neat) v: 3304, 2978, 2927, 1697, 1640, 1538, 1447, 1365, 1252, 1167, 1050 cm$^{-1}$. $^1$H NMR (300 MHz, CDCl$_3$) δ ppm: 6.8 (bs, 1H), 6.66 (d, J=6.9 Hz, 1H), 5.0 (d, J=5.4 Hz, 1H), 4.44 (qui, J=7.2 Hz, 1H), 4.10 (qui, J=6.9 Hz, 1H), 3.5-3.28 (m, 4H), 2.08 (qui, J=6.6 Hz, 2H), 1.46 (s, 9H), 1.39 (d, J=6.9 Hz, 3H), 1.37 (d, J=6.9 Hz, 3H). $^{13}$C NMR (75 MHz, CDCl$_3$) δ ppm: 173, 172, 155, 81, 50, 49, 38, 32, 30, 28, 17. HRMS (EI) m/z calculated for $C_{14}H_{26}BrN_3O_4$—379.1107, Found—402.100 [M+Na]$^+$.

Step III: Synthesis of TFA.Ala-Ala-Ala-NH—(CH$_2$)$_3$—Br

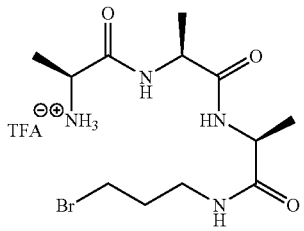 [SMILES: "TFA" ; C[C@H]([NH3+])C(=O)N[C@@H](C)C(=O)N[C@@H](C)C(=O)NCCCBr]

The desired compound (TFA.(Ala)$_3$-NH—(CH$_2$)$_3$—Br) was synthesized by the general procedure for Boc-deprotection (described earlier) of the corresponding Boc-protected peptide precursor. A typical experiment at 65 μmol scale was complete in 3.5 h and yielded the desired product (100%) without any purification after removal of solvent under high vacuum. The resulting residue was taken up directly for coupling in the next step. TLC (MeOH:DCM 1:4; R$_f$—0.53).

$^1$H NMR (300 MHz, CDCl$_3$) δ ppm: 4.18 (q, J=7.2 Hz, 1H), 4.04 (q, J=7.2 Hz, 1H), 3.92 (q, J=7.2 Hz, 1H), 3.30 (t, J=6.6 Hz, 2H), 3.20 (m, 2H), 1.88 (quin, J=6.3 Hz, 2H), 1.36 (d, J=7.2 Hz, 3H), 1.22 (t, J=6.9 Hz, 6H). IR (Heptane Gell) v: 2992, 2885, 2810, 1696, 1529, 1445, 1337, 1205, 968 cm$^{-1}$.

Example 5

Cyclization to [Ala-Ala-NH—(CH$_2$)$_3$]$_{cyclo}$

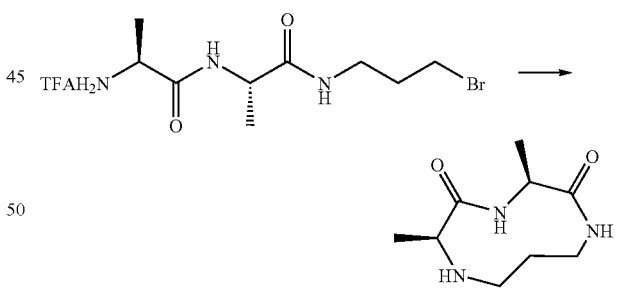

Method 1: H$_2$O/NaHCO$_3$

To a solution of the TFA salt of H$_2$N-Ala-Ala-NH—(CH$_2$)$_3$—Br (403 mg, 1.02 mmol) in double deionized water (16 mL), cooled to 0° C., was added K$_2$CO$_3$ (260 mg, 3.08 mmol) and stirred for 10 minutes, when TLC indicated the complete consumption of the salt and formation of the acyclic free amine. The mixture was allowed to warm to r.t. and stirred further until TLC indicated the complete disappearance of the acyclic free amine from the reaction mixture (MeOH:DCM—1:4, R$_f$—0.22) (80 h). The mixture was quenched with 3 equivalents of ammonium chloride and the mixture was lyophilized. The resulting residue was diluted with MeOH (5 mL), filtered over celite and the organic layer was concentrated under vacuum to yield the desired cyclized product in high purity (>95% by $^1$H NMR) and yield (100%-$^1$H NMR). The spectral data for the major conformer and the minor conformer are as presented below Major conformer: $^1$H NMR (300 MHz, D$_2$O), δ ppm: 4.44 (q, J=7.2 Hz, 1H), 4.11 (q, J=7.2 Hz, 1H), 3.53 (t, J=6.3 Hz, 2H), 3.26 (t, J=6.9 Hz, 2H), 1.76 (quint, J=6.6 Hz, 2H), 1.47 (d, J=7.2 Hz, 3H), 1.43 (d, J=7.2 Hz, 3H). $^{13}$C NMR (75 MHz, D$_2$O), δ ppm: 170.2 160.9, 158.9, 50.6, 48.2, 39.3, 29.1, 22.1, 19.4. HRMS (EI) m/z calculated-199.1321, found 200.1398 [M+H]$^+$, IR (neat) ν: 3422, 2923, 1680, 1453, 1203, 1134 cm$^{-1}$.

The peaks that are visible in the $^1$H NMR of the minor conformer are: $^1$H NMR (300 MHz, D$_2$O), δ ppm: 4.01 (q, J=6.6 Hz, 1H), 3.56 (t, J=6.3 Hz, 2H), 2.95 (t, J=7.2 Hz, 2H), 1.91 (quint, J=6.3 Hz, 2H), 1.32 (d, J=6.9 Hz, 3H).

Method 2: MeOH/K$_2$CO$_3$

To a solution of the TFA salt of H$_2$N-Ala-Ala-NH—(CH$_2$)$_3$—Br (20 mg, 50.9 μmol) in dry methanol (5 mL) (0.01 M), cooled to 0° C., was added K$_2$CO$_3$ (14 mg, 101.7 μmol) and stirred for 10 minutes. The mixture was allowed to warm to r.t. and stirred further until TLC indicated the complete disappearance of the starting TFA salt from the reaction mixture (MeOH:DCM—1:4, R$_f$=0.22) (80 h). The mixture was filtered over celite and washed with MeOH (5 mL) and the organic layer was concentrated under vacuum to yield the desired cyclized product in high purity (TLC R$_f$ matched with the previously synthesized products) and yield (100%).

The above cyclization reaction of H-Ala-Ala-NH—(CH$_2$)$_3$—Br was performed at 25° C. using a variety of solvents and a variety of bases as shown in Table 2. Table 2 also provides the yields for each reaction. The progress of several of these reactions was monitored using NMR. The NMR spectra showed the formation of the desired cyclized peptide as the main product of the reaction, with almost no soluble alkyl byproducts. For example, NMR spectra were recorded at various times (15 min, 24 hr, 38.5 hr, and 47 hr) for reaction No. 2 in Table 2. The spectra showed that the cyclized β-turn mimic exists in two distinct conformations in solution, with about 90% the peptides existing in the major conformation. The ratios of conformational populations can be calculated from the $^1$H NMR spectra of the cyclized product.

TABLE 2

Reaction conditions and yields for the cyclization of H-Ala-Ala-NH—(CH$_2$)$_3$—Br (at 25° C.)

| No. | Scale (mg) | Solvent | Base | Equiv. (M) | Consumption (%) | Period (h) | Method | Yield (%) |
|---|---|---|---|---|---|---|---|---|
| 1 | 10 | D$_2$O | K$_2$CO$_3$ | 2 | 100 | 90 | NMR | >95 |
| 2 | 20 | D$_2$O | NaHCO$_3$ | 2 | 100 | 83 | NMR | 100 |
| 3 | 400 | H$_2$O | NaHCO$_3$ | 2 | 100 | 89 | Column | >96 |
| 4 | 10 | CD$_3$OD | K$_2$CO$_3$ | 2 | 100 | 93 | NMR | >95 |
| 5 | 200 | CH$_3$OH | K$_2$CO$_3$ | 2 | 100* | 86 | NMR | >95 |
| 6 | 10 | CH$_3$CN | K$_2$CO$_3$ | 2 | 100 | 80 | TLC | — |

M), cooled to 0° C., was added K$_2$CO$_3$ (14 mg, 101.7 μmol) and stirred for 10 minutes, when TLC indicated the complete consumption of the salt and formation of the acyclic free amine. The mixture was allowed to warm to r.t. and stirred further until TLC indicated the complete disappearance of the acyclic free amine from the reaction mixture (MeOH:DCM—1:4, R$_f$=0.22) (83 h). The mixture was filtered over celite and washed with MeOH (5 mL) and the organic layer was concentrated under vacuum to yield the desired cyclized product in high purity (>95% by $^1$H NMR) and yield (100%-$^1$H NMR).

Method 3: CH$_3$CN/K$_2$CO$_3$

To a solution of the TFA salt of H$_2$N-Ala-Ala-NH—(CH$_2$)$_3$—Br (20 mg, 50.9 μmol) in dry acetonitrile (5 mL)

Example 6

Cyclization to [Ala-Ala-Ala-NH—(CH$_2$)$_3$]$_{cyclo}$

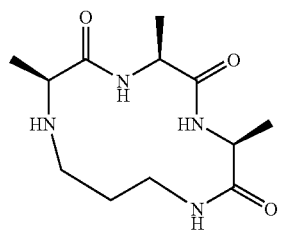 [SMILES: C[C@@H]1NCCCNC(=O)[C@H](C)NC(=O)[C@H](C)NC1=O]

To a solution of the TFA salt of H$_2$N-Ala-Ala-Ala-NH—(CH$_2$)$_3$—Br (80 mg, 160 μmol) in dry methanol (15 mL), cooled to 0° C., was added K$_2$CO$_3$ (69 mg, 500 μmol) and stirred for 10 minutes, when TLC indicated the complete consumption of the salt and formation of the acyclic free amine. The mixture was allowed to warm to r.t. and stirred further until TLC indicated the complete disappearance of the acyclic free amine from the reaction mixture TLC (MeOH: DCM—3:7; $R_f$—0.25) (70 h). The mixture was filtered over celite and washed with MeOH (5 mL) and the organic layer was concentrated under vacuum to yield the desired cyclized product (39 mg, 87%) in high purity (>95% by EI HRMS).

IR (NaCl, neat) ν: 3439(b), 2972, 2920, 1688, 1680, 1660, 1587, 1545, 1462, 1441, 1351, 1206, 1143 cm$^{-1}$. $^1$H NMR (300 MHz, D$_2$O) δ ppm: 4.10 (m, 4H), 3.54-3.35 (m, 3H), 3.11 (m, 2H), 1.58 (quin, J=6.6 Hz, 2H), 1.22-1.11 (m, 9H). HRMS (EI) m/z calculated for C$_{12}$H$_{22}$N$_4$O$_3$: 270.1692, observed: 293.1574 [M+Na]$^+$ (100%), 309.1329 [M+K]$^+$, 327.1416 [M+K+H$_2$O]$^+$, 341.1575 [M+K+MeOH]$^+$.

Example 7

Independent Synthesis of Potential Solvolysis Products

In the cyclization reactions of Examples 5 and 6, mass spectral analysis exhibited both the desired m/z fragment for the cyclized product and the m/z fragment ions for the corresponding water adducts. The latter adducts could arise during the cyclization (see scheme) or during the mass spectral analysis.

Confirmation of non existence of the possible Competing solvolysis reaction

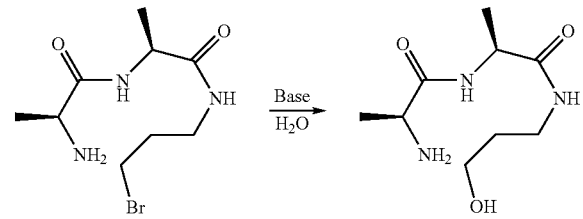

To prove that the cyclic products had been formed predominantly instead of the possible product from solvolysis, the corresponding Ala-(Ala)$_{1-2}$-NH—(CH$_2$)$_3$—OH compounds were independently synthesized as follows and their NMR and mass spectra compared to those for the cyclization products to confirm the structure of the cyclic products.

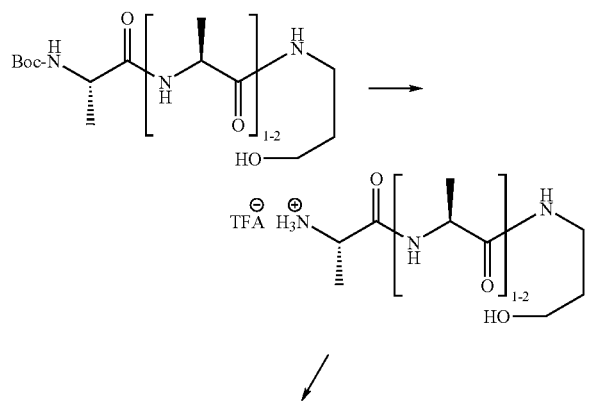

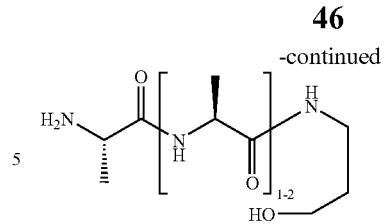

A. Synthesis of TFA.Ala-Ala-NH—(CH$_2$)$_3$—OH

TFA (1 mL) was added to an ice cold solution of Boc-Ala-Ala-NH—(CH$_2$)$_3$—OH (80 mg, 0.25 mmol) in DCM (9 mL) and stirred for 3.5 h, at which point TLC indicated complete consumption of the starting carbamate. The solvent was removed and the residue was concentrated under vacuum to yield the corresponding TFA salt in good yield (83 mg, 100%), as a solid (m.p. 163-164° C.) which was taken up directly for the next reaction. TLC (MeOH:DCM—1:3; $R_f$—0.31).

IR (KBr) ν: 3272.8, 3090, 2926.3, 2854.4, 1790.6, 1544.7, 1200, 1177.9, 1134.4, 838.8, 723.1 cm$^{-1}$. $^1$H NMR (400 MHz, D2O) δ ppm: 4.24 (t, J=6.8 Hz, 0.7H), 4.18 (q, J=7.2 Hz, 1H), 3.99 (q, J=7.2 Hz, 1H), 3.52 (t, J=6.4 Hz, 1.3H), 3.9-3.12 (m, 2H), 1.89 (qui, J=6.4 Hz, 0.7H), 1.66 (qui, J=6.8 Hz, 1.3 Hz), 1.45 (d, J=6.8 Hz, 3H), 1.29 (d, J=7.2 Hz, 3H). $^{13}$C NMR (100 MHz, CDCl$_3$) δ ppm: 174.6, 170.5, 162.8 (q), 59, 50, 48.83, 36.2, 30.8, 16.43.

B. Synthesis of TFA.Ala-Ala-Ala-NH—(CH$_2$)$_3$—OH

The desired compound (TFA.Ala-(Ala)$_2$-NH—(CH$_2$)$_3$—OH) was synthesized by the general procedure for Boc-deprotection (described in the previous example) of the corresponding Boc-protected peptide precursor. A typical experiment at 210 μmol scale was complete in 3.5 h and yielded the desired product (100%) as a solid (m.p.—183-184° C.) without any purification after removal of solvent under high vacuum. The resulting residue was taken up directly for the next step. TLC (MeOH:DCM—1:9; $R_f$—0.28).

IR (KBr) ν: 3281.7, 2924.1, 2855.1, 1790.48, 1679.4, 1637.9, 1528.7, 1448.1, 1361.1, 1203.9, 1179.9 cm$^{-1}$. $^1$H NMR (300 MHz, D$_2$O) δ ppm: 4.11 (q, J=6.9 Hz, 1H), 3.99 (q, J=6.9 Hz, 1H), 3.86 (q, J=6.9 Hz, 1H), 3.38 (t, J=6.6 Hz, 2H), 3.06 (m, 2H), 1.52 (quin, J=6.0 Hz, 2H), 1.31 (d, J=7.2 Hz, 3H), 1.17 (t, J=7.2 Hz, 6 Hz). $^{13}$C NMR (75 MHz, CDCl$_3$) δ ppm: 175.6, 175.2, 171.4, 60.1, 50.9, 50.6, 49.9, 37.20, 31.9, 17.62, 17.57, 17.43.

C. Synthesis of Ala-Ala-NH—(CH$_2$)$_3$—OH

To a solution TFA.Ala-Ala-NH—(CH$_2$)$_3$—OH (50 mg, 0.15 mmol) in D$_2$O (600 μL) in an NMR tube was added NaHCO$_3$ (13 mg, 0.15 mmol) and stirred at r.t. for 5 min when the TLC indicated complete consumption of the starting TFA salt and the NMR for the solution was recorded. TLC (MeOH:DCM—1:3; $R_f$—0.22).

$^1$H NMR (400 MHz, D$_2$O) δ ppm: 4.15 (quin, J=9.2 Hz, 1H), 3.90 (m, 1H), 3.49 (t, J=6.0 Hz, 2H), 3.13 (m, 2H), 1.62 (m, 2H), 1.40 (d, J=7.2 Hz, 1H), 1.26 (d, J=7.2 Hz, 3H), 1.19 (d, J=7.2 Hz, 2H). $^{13}$C NMR (100 MHz, CDCl$_3$) δ ppm: 171.8, 175.1, 174.7, 171.3, 59.12, 59.03, 51.74, 50.1, 49.8, 48.9, 36.3, 36.2, 30.8, 17.2, 16.8, 16.6. HRMS (EI) m/z calculated for C$_9$H$_{19}$N$_3$O$_3$-217.1426 found-240.1303 [M+Na]$^+$.

D. Synthesis of Ala-Ala-Ala-NH—(CH₂)₃—OH

To a solution of TFA.Ala-(Ala)₂-NH—(CH₂)₃—OH (50 mg, 0.125 mmol) in D₂O (600 μL) in an NMR tube was added NaHCO₃ (11 mg, 0.125 mmol) and shaken at r.t. for 5 min and the NMR spectrum for the solution was recorded.

¹H NMR (300 MHz, D₂O) δ ppm: 4.17 (q, J=6.6 Hz, 1H), 4.05 (q, J=7.2 Hz, 1H), 3.87 (m, 1H), 3.44 (t, J=6.3 Hz, 2H), 3.11 (m, 2H), 1.57 (quin, J=6.6 Hz, 2H), 1.35 (d, J=6.6 Hz, 2H), 1.23 (t, J=6.6 Hz, 6H), 1.14 (d, J=7.5 Hz, 1H). ¹³C NMR (75 MHz, CDCl₃) δ ppm: 175.7, 175.34, 161.1, 60.1, 50.9, 50.6, 50.0, 37.2, 31.8, 18.17, 17.4. HRMS (EI) m/z calculated for C₁₂H₂₄N₄O₄—288.1798, Found—311.1693 [M+Na]⁺.

Example 8

Solution Phase Synthesis of a β-Turn Mimic for Pro-Gly

A. Synthesis of Boc-Pro-Gly-NH—(CH₂)₃—OH

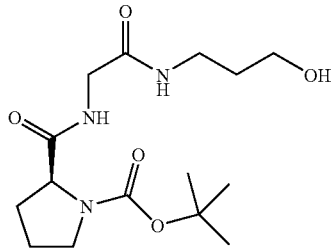 [SMILES: CC(C)(C)OC(=O)N1CCC[C@H]1C(=O)NCC(=O)NCCCO]

To a cold (−15° C.) solution of Boc-Pro-Gly-OH (610 mg, 2.24 mmol) and NMM (369 μl, 3.36 mmol) in THF (8 mL) was added ECF (2201 μl, 2.3 mmol) and stirred vigorously. After 2 min. a solution of 1-amino-3-propyl alcohol (220 mg, 2.68 mmol) in THF (2 mL) was added to it followed by NMM (505 mg, 5 mmol) and stirred for further 30 minutes. The mixture was warmed to r.t. and stirred for 8 h. The solvent was removed under reduced pressure to give a residue which was diluted with EtOAc and washed with saturated citric acid, saturated NaHCO₃ and the organic layer was dried over Na₂SO₄ and concentrated under vacuum to give a residue, which was purified by silica gel flash column chromatography (EtOAc:MeOH—50:1) to give the desired product as a thick oil in good yields (633 mg, 80%). TLC (MeOH:DCM—1:4; R_f—0.5).

IR (NaCl, neat) ν: 3423 (br), 2979, 2878, 1650, 1414, 1164.35 cm⁻¹. ¹H NMR (300 MHz, CDCl₃) δ ppm: 7.46 (S, 1H), 7.15 (S, 1H), 3.8-4.02 (m, 4H), 3.57-3.58 (t, J=5.2 Hz, 2H), 1.66 (quin, J=5.6 Hz, 2H), 1.43 (s, 9H), 1.12 (t, J=7.2 Hz, 1H). ¹³C NMR (100 MHz, CDCl₃) δ ppm: 173.13, 170.27, 155 (C=O), 80, 61, 60, 59, 49, 47, 44, 42, 36, 31, 30, 29, 24, 17, 14. HRMS (EI) m/z calculated for C₁₅H₂₇N₃O₅-329.1951, Found—352.1836 [M+Na]⁺, 252.1289 [M+Na-Boc]⁺.

B. Synthesis of Boc-Pro-Gly-NH—(CH₂)₃—Br

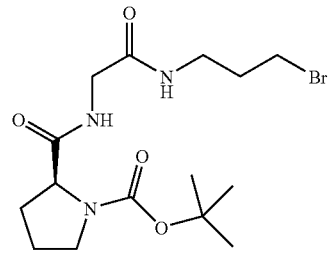 [SMILES: CC(C)(C)OC(=O)N1CCC[C@H]1C(=O)NCC(=O)NCCCBr]

The desired compound (Boc-Pro-Gly-NH—(CH₂)₃—Br) was synthesized by the general procedure for the NBS bromination (described earlier) of the corresponding alcohol precursor. A typical experiment at 0.85 mmol scale was complete in 45 min. and yielded the desired product (86%) after purification by silica gel flash column chromatography (EtOAc:Pet. Ether—4:1). TLC (MeOH:DCM—1:4; R_f—0.53).

IR (NaCl, neat) ν: 3306.4, 2983.3, 2938, 1654.6, 1527.4, 1351.9, 1172.5, 943 cm⁻¹. ¹H NMR (300 MHz, CDCl₃) δ ppm: 7.40 (s, 1H), 7.32 (s, 1H), 4.2-3.7 (m, 3H), 3.4-3.3 (m, 6H), 2.10-1.78 (m, 6H), 1.40 (S, 9H). HRMS (EI) m/z calculated for C₁₅H₂₆BrN₃O₄-391.1107, Found—414.1010 [M+Na]⁺, 212.1405 [M-Boc-HBr]⁺.

C. Synthesis of TFA.Pro-Gly-NH—(CH₂)₃—Br

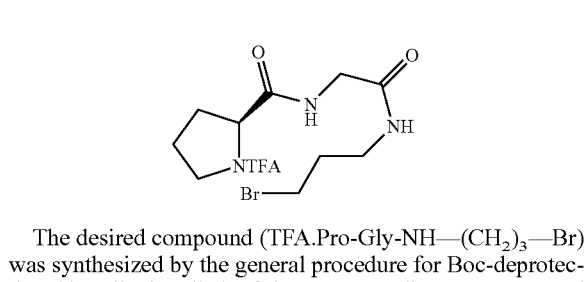

The desired compound (TFA.Pro-Gly-NH—(CH₂)₃—Br) was synthesized by the general procedure for Boc-deprotection (described earlier) of the corresponding Boc-protected peptide precursor. A typical experiment at 76 μmol scale was complete in 3.5 h and yielded the desired product (100%) without any purification after removal of solvent under high vacuum. TLC (MeOH:DCM—1:4; R_f—0.41). The resulting residue was taken up directly for coupling in the next step.

¹H NMR (300 MHz, CDCl₃) δ ppm: 4.31 (m, 1H), 3.81 (d, J=5.7 Hz, 2H), 3.35-3.17 (m, 6H), 2.32 (m, 1H), 2.02-1.86 (m, 5H). ¹³C NMR (75 MHz, CDCl₃) δ ppm: 171.99, 171.2, 163.8, 64.1, 60.7, 47.53, 42.3, 37.8, 30.6, 26.8, 24.7. HRMS (EI) m/z calculated for C₁₂H₁₈BrF₃N₃O₄—404.0433, Found—314.0474 [M+Na-TFA]⁺, 292.0630 [M+H-TFA]⁺.

D. Cyclization of H-Pro-Gly-NH—(CH₂)₃—Br

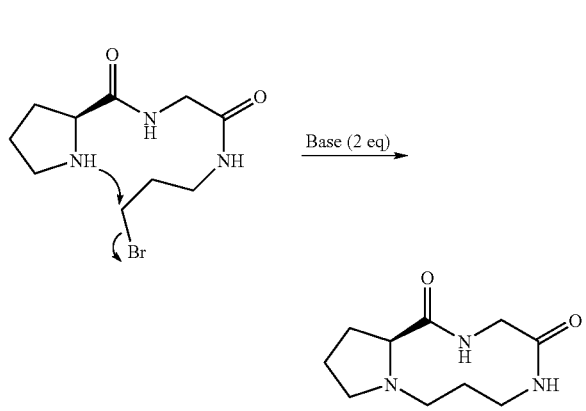

To a solution of the TFA salt of H₂N-Pro-Gly-NH—(CH₂)₃—Br (525 mg, 1.3 mmol) in double deionized water (25 mL), cooled to 0° C., was added NaHCO₃ (219 mg, 2.60 mmol) and stirred for 10 minutes, when TLC indicated the complete consumption of the salt and formation of the acyclic free amine. The mixture was allowed to warm to r.t. and stirred further until TLC indicated the complete disappearance of the acyclic free amine from the reaction mixture (MeOH:DCM—2:3, R_f=0.34) (27 h). The mixture was quenched with 3 equivalents of ammonium chloride and lyophilized. The resulting residue was diluted with MeOH (5 mL), filtered over celite and the organic layer was concentrated under vacuum to yield the desired cyclized product (274 mg, 100%) (>95% by HRMS-EI).

¹H NMR (300 MHz, CDCl₃) δ ppm: 4.28 (m, 1H), 4.02, 3.71 (dd, J=6.6 Hz, 1H), 3.54 (m, 3H), 3.39 (m, 3H), 2.97 (t, J=7.8 Hz, 1H), 2.30-1.72 (m, 6H). ¹³C NMR (75 MHz, CDCl₃) δ ppm: 172.14, 161.18, 61.34, 59.7, 49.1, 46.56, 42.3, 38.6, 32.3, 28.9, 28.2, 23.4. HRMS (EI) m/z calculated for C₁₀H₁₇N₃O₂-211.1321, Found—212.1406 [M+H]⁺.

Example 9

Independent Synthesis of Potential Solvolysis Products

To prove that the cyclic product of Example 8 had been formed predominantly instead of the possible product from solvolysis, the corresponding Pro-Gly-NH—(CH₂)₃—OH compound was independently synthesized as follows and its mass spectrum compared to that for the cyclization product to confirm the cyclic structure.

Confirmation of non existence of the possible Competing solvolysis reaction

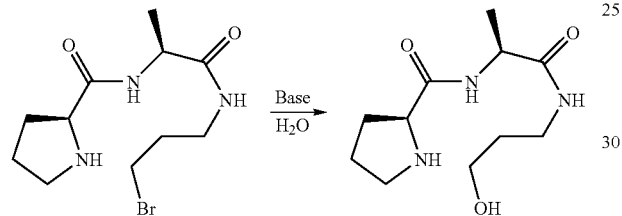

A. Synthesis of TFA.Pro-Gly-NH—(CH₂)₃—OH

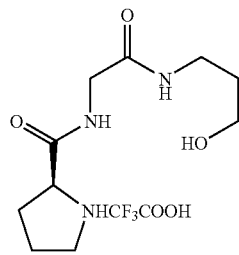

The desired compound (TFA.Pro-Gly-NH—(CH₂)₃—OH) was synthesized by the general procedure for Boc-deprotection (described earlier) of the corresponding Boc-protected peptide precursor. A typical experiment at 300 μmol scale was complete in 3.5 h and yielded the desired product (100%) without any purification after removal of solvent under high vacuum. The resulting residue was taken up directly for coupling in the next step.

IR (KBr) ν: 3322.80, 3080.8, 2979, 2935, 2881, 1673.91, 1668.35, 1548.4, 14097, 1367.9, 1247, 1163.93, 1134.1, 774.9, 734.2 cm⁻¹. ¹H NMR (300 MHz, D₂O) δ ppm: 4.13 (bs, 1H), 3.64 (d, J=6.6 Hz, 2H), 3.30 (t, J=6.6 Hz, 2H), 3.12 (m, 2H), 2.97 (t, J=6.9 Hz, 2H), 2.17 (m, 2H), 1.76 (m, 3H), 1.43 (quin, J=6.6 Hz, 2H). ¹³C NMR (75 Mhz, D₂O) δ ppm: 171.6, 171.1, 163.4, 60.9, 60.3, 47.6, 43.7, 37.5, 31.87, 30.6, 30.5, 24.8. HRMS (EI) m/z calculated for C₁₂H₁₉F₃N₃O₅-343.1355, Found—230.1503 [M+H−TFA]⁺, 252.1319 [M+Na−TFA]⁺, 459.2953 [2M+H−2TFA]⁺, 481.2787 [2M+Na−2TFA]⁺.

B. Synthesis of H-Pro-Gly-NH—(CH₂)₃—OH

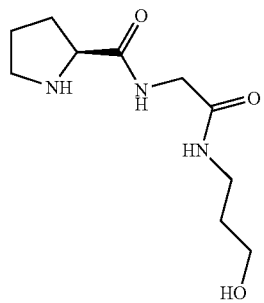 [SMILES: O=C(CNC(=O)[C@@H]1CCCN1)NCCCO]

To a solution of TFA.Pro-Gly-NH—(CH₂)₃—OH (50 mg, 0.145 mmol) in D₂O (600 μL) in an NMR tube was added NaHCO₃ (12 mg, 0.145 mmol) and shaken at r.t. for 5 min and the NMR for the solution was recorded.

¹H NMR (300 MHz, CDCl₃) δ ppm: 4.3 (b, 1H), 3.81 (d, J=6.9 Hz, 2H), 3.46 (t, J=6 Hz, 2H), 3.26 (m, 2H), 3.13 (t, J=6.6 Hz, 2H), 2.31 (m, 1H), 1.93 (m, 3H), 1.59 (quin, J=6.6 Hz, 2H). ¹³C NMR (75 MHz, CDCl₃) δ ppm: 171.6, 171.3, 60.9, 60.1, 47.56, 43.7, 37.4, 31.87, 30.54, 24.8. HRMS (EI) m/z calculated for C₁₀H₁₉N₃O₃-229.1426, Found: 252.1319 [M+Na]⁺.

Example 10

Solution Phase Synthesis of a β-Turn Mimic Using Macrolactamization of Ns-Protected β-sheet Mimic Step I: Intramolecular N-alkylation of N-nosyl Protected Amines A. Synthesis of Boc-Ala-Ala-NH-propyl-(N-Ns)-Ala-OMe

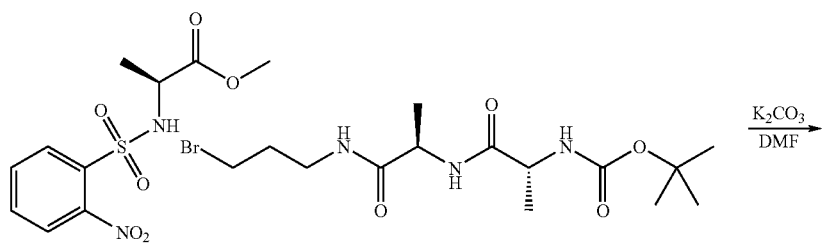

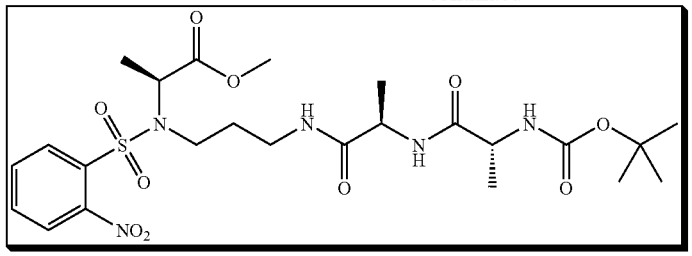

Nosyl-Ala-OMe (113 mg, 0.34 mmol) and K$_2$CO$_3$ (73 mg, 0.53 mmol) were dissolved in dry DMF (1.5 ml) at r.t. and stirred for 0.5 h, then Boc-Ala-Ala-NH—(CH$_2$)$_3$—Br (100 mg, 2.64 mmol) was added and stirred for 36 h. DMF was removed under reduced pressure to give a residue which was diluted with EtOAc and filtered over celite on a cintered crucible. The filtrate was concentrated under vacuum to give a residue which was purified by silical gel column chromatography (EtOAc) to give the desired product (118 mg, 84%) as a viscous oil. (TLC:EtOAc; R$_f$ 0.41).

IR (NaCl, neat) v: 3314, 3092, 2980, 2936, 2880, 1745, 1666, 1545, 1454, 1371, 1164.72, 1069, 991, 915, 852 cm$^{-1}$. $^1$H NMR (300 MHz, CDCl$_3$) δ ppm: 8.03 (m, 1H), 6.66 (m, 2H), 7.54 (m, 1H), 6.93 (t, J=5.7 Hz, 1H), 6.88 (d, J=7.2 Hz, 1H), 5.23 (d, J=6.6 Hz, 1H), 4.70 (q, J=7.2 Hz, 1H), 4.41 (qui, J=6.9 Hz, 1H), 4.10 (m, 1H), 3.54 (s, 3H), 3.43 (m, 1H), 3.13-3.31 (m, 3H), 1.81 (qui, J=7.8 Hz, 2H), 1.46 (d, J=7.8 Hz, 3H), 1.39 (s, 9H), 1.33 (d, J=6.6 Hz, 3H), 1.30 (d, J=6.9 Hz, 3H). $^{13}$C NMR (75 MHz, CDCl$_3$) δ ppm: 173, 172.2, 171.6, 155.71, 148, 133.5, 131.6, 131, 124, 80.4, 56, 52.3, 50.7, 49.1, 43.6, 36.7, 30.4, 28.2, 18.1, 18, 16.6. HRMS (EI) m/z calculated for C$_{24}$H$_{37}$N$_5$O$_{10}$S—587.6431, Found—610.2157 [M+Na]+.

B. General Procedure for Synthesis of Bromopropyl-(N-Ns)-Ala-OMe

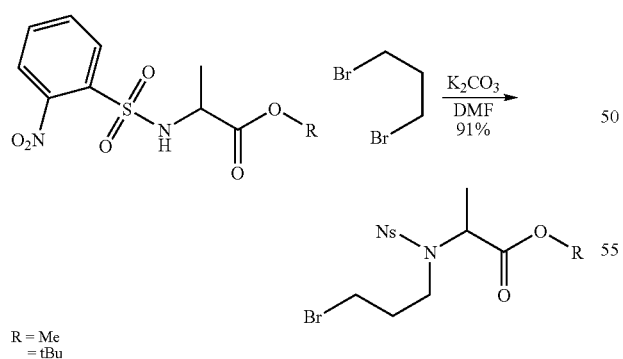

R = Me
= tBu

To a solution of the N-nosyl protected alkyl alaninate (1 equivalent) in dry DMF (0.2 M) was added K$_2$CO$_3$ (2 equivalents) and 1,3-dibromopropane (4 equivalents) and stirred at 25° C. The mixture was monitored for progress by TLC (developing system ethyl acetate/hexanes: 1:1) until complete consumption of the N-nosyl sulfonamide protected alkyl alaninate (9 h). After completion of the reaction, the mixture was diluted with water and thoroughly washed with ether. The combined organic extracts were dried over Na$_2$SO$_4$ and concentrated in vacuum to give a residue, which was purified by silica gel column chromatography (EtOAc:hexanes-1:6) to yield the desired product in >90% yield.

The following products were synthesized using the above processes.

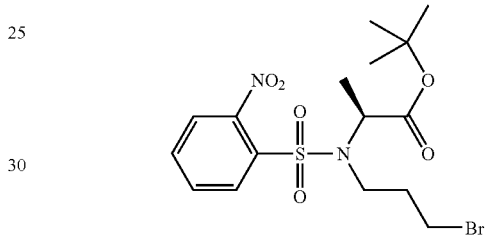

Yellow solid: m.p. 40-42° C. $^1$H NMR (300 MHz, CDCl$_3$) δ ppm: 1.34 (s, 9H), 1.51 (d, J=7.5 Hz, 3H), 2.12-2.39 (m, 2H), 3.28-3.65 (m, 3H), 3.54-3.65 (m, 1H), 4.67 (q, J=7.5 Hz, 1H), 7.57-7.62 (m, 1H), 7.66-7.72 (m, 2H), 8.05-8.08 (m, 1H). $^{13}$C NMR (75 MHz, CDCl$_3$) δ ppm 16.9, 27.7, 30.5, 33.7, 45.0, 56.8, 82.2, 124.0, 131.1, 131.5, 133.5, 170.14. HRMS (EI) m/z calculated for [C$_{16}$H$_{23}$BrN$_2$O$_6$S+Na]- 473.0358 found-473.0345, 475.0318 [M+Na]$^+$. IR (neat) v: 2979 (C—H), 1732 (C=O), 1370 (S=O), 1149 (C—O) cm$^{-1}$.

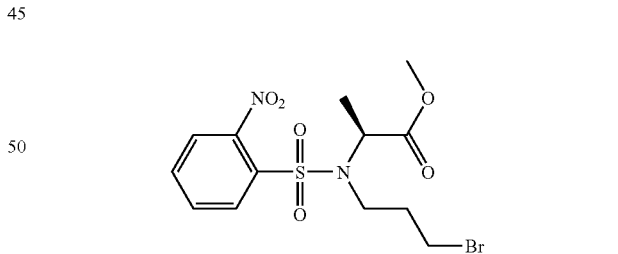

Yellow oil. $^1$H NMR (300 MHz, CDCl$_3$) δ ppm: 1.55 (d, J=7.2 Hz, 3H), 2.10-2.39 (m, 2H), 3.33-3.45 (m, 3H), 3.52-3.63 (m, 1H), 3.63 (s, 3H), 4.8 (q, J=7.2 Hz, 1H), 7.59-7.68 (m, 1H), 7.68-7.73 (m, 2H), 8.06-8.09 (m, 1H). $^{13}$C NMR (75 MHz, CDCl$_3$) δ ppm: 16.6 (CH$_3$), 30.4 (CH$_2$—CH$_2$—CH$_2$—Br), 33.4 (CH$_2$—Br), 44.9 (N—CH$_2$), 52.44 (C$_α$), 56.17 (OCH$_3$), 124, 131.1, 131.6, 133.6 (Ar), 171.7 (C=O). HRMS (EI) m/z calcd for [C$_{13}$H$_{17}$BrN$_2$O$_6$SNa]: 430.9888 found: 430.9888, 432.9882 [M+Na]$^+$ (100%), 351.0580 (35%). IR (v, cm$^{-1}$) neat, CH$_2$Cl$_2$: 2953 (C—H), 1742 (C=O), 1544 (N—O), 1373 (S=O), 1154 (C—O).

Step II: Macrolactamization of N-alkylated-N-nosyl Protected Peptides

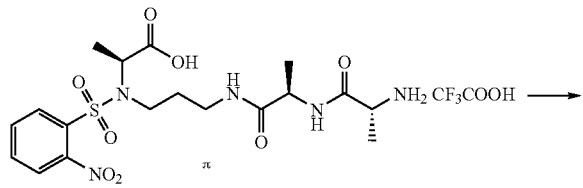

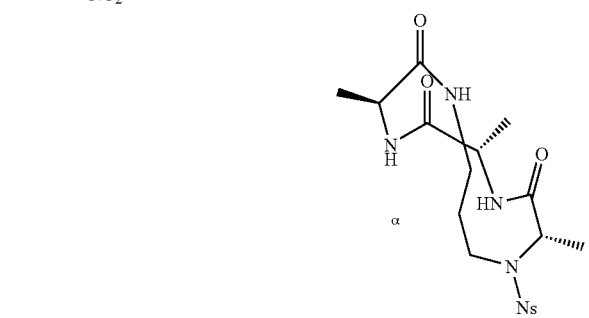

To an ice cold solution of the TFA salt of the amino peptidic acid (π) (57 mg, 0.104 mmols) in DMF (2.5 ml) was added HOBT (21.2 mg, 0.156 mmols) and stirred for 10 min. EDCl (30 mg, 0.16 mmols) was added and the mixture was stirred for further 0.5 h. Then DIPEA (55 µl, 0.312 mmols) was added and the mixture was warmed to room temperature and stirred for 36 h. DMF was removed under vacuum and the resulting residue was diluted with EtOAc and the organic solution was washed with brine, 1N HCl, saturated NaHCO$_3$ solution, dried over Na$_2$SO$_4$ and concentrated under vacuum to give the desired product as a thick viscous oil (34 mg, 82%). Spectral analysis (EI HRMS) of the crude residue indicated high level of purity. However, during purification using silica gel column chromatography (EtOAc:Hexanes—9:1) there was significant lose of compound on the column, resulting poor yields (14 mg, 34%). Efforts are on to purify the product by HPLC. (TLC-MeOH:EtOAc—1:10; R$_f$—0.36).

HRMS (EI) m/z calculated for [M+Na]$^+$—478.1372, observed—478.1369; calculated for [2M+Na]$^+$—933.2847, observed—933.2876. IR (NaCl, neat) ν: 3400.5 (br), 3076.9, 2937.6, 2984, 1665.4, 1544.4, 1374.4, 1345.9, 1162.7, 1050.9, 1027.2, 1006.6 cm$^{-1}$.

Step III: Nosyl deprotection of N-alkylated-Protected Peptides

The nosyl-protected β-turn mimic can be deprotected either prior to cyclization or post cyclization using arylthiols and a base as demonstrated by the next reaction.

A. Synthesis of HO—(CH$_2$)$_3$-Ala-OtBu

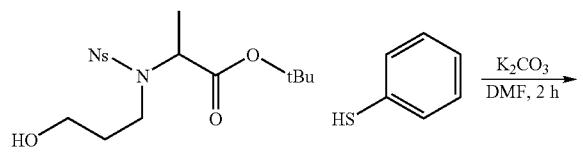

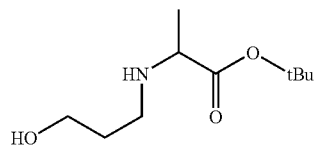

To a solution of N-alkyl N-nosyl t-butyl alaninate (97 mg, 0.25 mmols) in dry DMF (1.66 ml, 0.15 M) was added K$_2$CO$_3$ (103 mg, 0.37 mmol) and PhSH (31 µL, 0.3 mmols) and stirred at room temperature. After 30 minutes of stirring, further portions of PhSH (31 µl, 0.3 mmols) and K$_2$CO$_3$ (51.7 mg, 0.19 mmols) were added to the reaction mixture and stirred. The mixture was monitored for progress by TLC (developing system ethyl acetate/hexanes: 7:3) until complete consumption of the N-alkyl N-nosyl t-butyl alaninate (2 h). After completion of the reaction, the mixture was quenched with water (250 µL) and the DMF was evaporated under high vacuum. The resulting residue was acidified with 2 N HCl by stirring for 5 minutes at 25° C. and then washed with copious amounts of diethyl ether to remove all the organic impurities. The aqueous part was the basified to pH 8-9 with solid NaHCO$_3$ and thoroughly extracted with ethyl acetate. The organic extract was dried (over Na$_2$SO$_4$) and concentrated under vacuum to yield the desired N-(hydroxypropyl) t-butyl alaninate (50.6 mg, 100%) as a oil, which was used for peptide coupling without further purification.

Example 11

Solution Phase Synthesis of a Cyclic Peptide Using the Macrolactamization Reaction

Step I: Synthesis of 1-(N-tert-Butyl carbamato)-amino-3-bromo propane

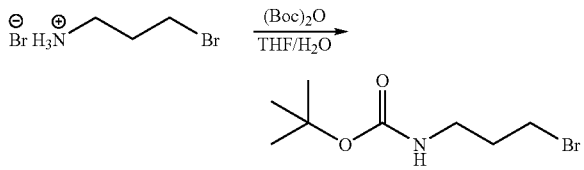

To a cold (0° C.) stirring mixture of 1-amino-3-propyl bromide hydrobromide (1 gm, 4.63 mmol) and ditertiarybutyl dicarbonate (1 gm, 4.63 mmol) in dichloromethane (5 mL) was added triethyl amine (1.018 mL, 9.26 mmol) and the mixture was warmed to r.t. and stirred for further 10 h. The mixture was diluted with dichloromethane (10 mL), washed with water (2×5 mL), dried over Na$_2$SO$_4$ and concentrated under vacuum to get a residue which was purified using silica gel flash column chromatography (EtOAc: Pet. Ether—1:24) to get the desired product as a viscous oil in high yields (978 mg, 89%). (TLC-R$_f$=0.41; EtOAc:Pet. Ether—3:7).

$^1$H NMR (400 MHz, CDCl$_3$) δ ppm: 4.73 (bs, 1H), 3.44 (t, J=6.5 Hz, 2H), 3.27 (q, J=6.1 Hz, 2H), 2.04 (quint, J=6.4 Hz), 1.44 (s, 9H). $^{13}$C NMR (100 MHz, CDCl$_3$) δ ppm: 155.9, 85.1, 38.9, 32.6, 30.8, 28.3.

Step II: Synthesis of N-Nosyl-N-alkyl-N'-Boc protected peptido ester

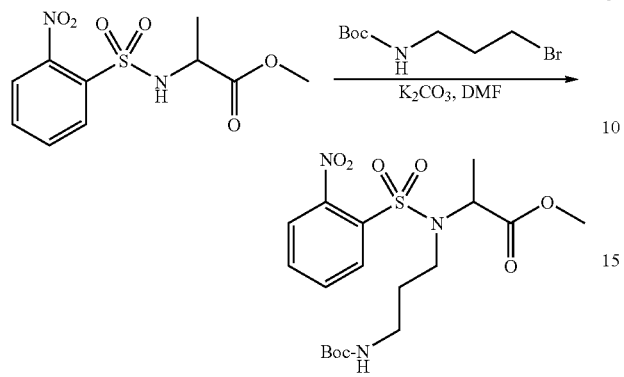

A mixture of N-Nosyl-methyl alaninate (860 mg, 2.99 mmol) and $K_2CO_3$ (824 mg, 5.97 mmol) in dry DMF (10 ml) was stirred for 30 minutes followed by the addition of N-Boc-1-amino propyl-3-bromide (850 mg, 3.59 mmol) and stirred vigorously for further 36 h at r.t. The mixture was diluted with water (5 mL) and extracted with ethyl acetate (3×15 mL) and the organic extracts were dried over $Na_2SO_4$ and concentrated under vacuum to get a residue, which was subjected to silica gel flash column chromatography (EtOAc:Pet. Ether—3:7) to get the desired product in high yields (987 mg, 74.3 mg). (TLC-$R_f$=0.31; EtOAc:Pet. Ether—1:1).

IR (NaCl, neat) ν: 3418, 3097, 2978, 2956, 1732, 1746, 1714, 1700, 1547, 1539, 1520, 1455, 1392, 1368, 1353, 1251, 1166, 1127 cm$^{-1}$. $^1$H NMR (300 MHz, CDCl$_3$) δ ppm: 8.10-8.02 (m, 1H), 7.76-7.69 (m, 2H), 7.67-60 (m, 1H), 4.77 (q, J=7.2 Hz, 1H), 3.61 (s, 3H), 3.45 (dd, J=6.0, 4.0 Hz, 1H), 3.25 (dd, 6.0, 4.0 Hz, 1H), 3.20-3.16 (m, 2H), 1.91-1.79 (m, 1H), 1.52 (d, J=7.2 Hz, 3H), 1.44 (s, 9H). HRMS (EI) m/z calculated for [M-Boc+H]$^+$=346.1073, Found=346.1086 (100%); calculated for $C_{18}H_{27}NaN_3O_8S$-[M+Na]$^+$=468.1417, Found=468-1415; calculated for $C_{18}H_{27}KN_3O_8S$-[M+K]$^+$=484.1156, Found=484.1302.

Step III: Synthesis of N-Nosyl N-alkyl N'-Boc protected peptido acid

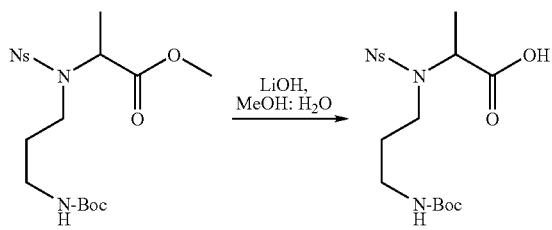

To a solution of LiOH (113 mg, 2.70 mmol) in water (2 mL) at r.t. was added a solution of the N-Nosyl protected N-alkyl methyl alaninate derivative (800 mg, 1.80 mmol) in methanol (6 mL) followed by a solution of LiOH (113 mg, 2.70 mmol) in water (2 mL) and stirred until TLC (EtOAc) indicates complete consumption of the starting ester (1 h). The mixture was concentrated under vacuum to remove methanol followed by acidification with 1N HCl until pH of the solution turned 2 and the mixture was extracted with EtOAc (3×10 mL) to get the corresponding carboxylic acid as a residue (820 mg, >100%) which was characterized by $^1$H NMR (confirmation of hydrolysis of the methyl ester) and directly taken up for the next reaction without any further purification. (TLC—$R_f$=0.31; EtOAc).

$^1$H NMR (300 MHz, CDCl$_3$) δ ppm: 8.06-8.01 (m, 1H), 7.78-7.67 (m, 2H), 7.63-7.61 (m, 1H), 6.50-6.10 (bs, 1H), 6.24 (d, J=8.1 Hz, 1H), 4.76 (q, J=7.2 Hz, 1H), 15.0, 5.7 Hz, 1H), 3.29-3.10 (m, 3H), 1.95-1.70 (m, 2H), 1.51 (d, J=7.2 Hz, 3H), 1.43 (s, 9H).

Step IV: Synthesis of the TFA salt of N-Nosyl N-alkyl peptido amino acid

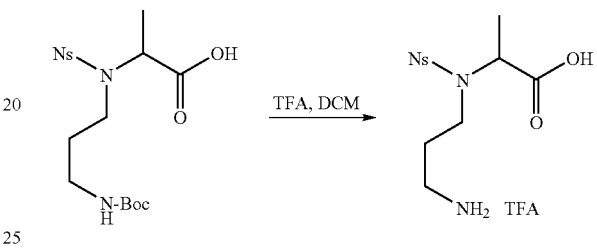

To the residue from the above reaction (200 mg, 0.46 mmol) was added a solution of TFA (1 mL) in DCM (9 mL) and stirred for 3 h, when TLC (EtOAc:MeOH—9:1) showed complete consumption of the starting material. The solution was concentrated under vacuum to get a residue (194 mg, 94%), which was used directly for synthesis in the next step.

Step V: Macrolactamization of N-nosyl N-alkyl peptido amino acid

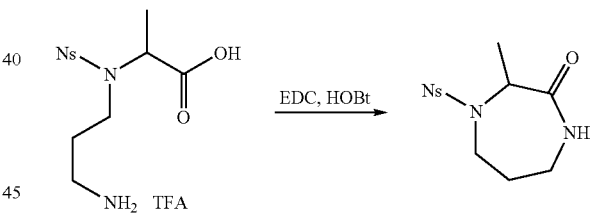

To a cold (0° C.) solution of the TFA salt of the peptido amino acid derivative (190 mg, 0.43 mmol) and HOBT (173 mg, 1.28 mmol) in dry DMF (20 mL) was added EDCl (245 mg, 1.28 mmol) followed by DIPEA (372 μL, 2.135 mmol). The mixture was slowly warmed to r.t. and stirred for 40 h, till TLC (EtOAc) indicated complete consumption of the starting material. The mixture was then quenched with water (5 mL), DMF was removed under vacuum and the resulting residue was diluted with EtOAc (25 mL). The organic solution was washed with brine (5 mL), 1N HCl solution (5 mL), saturated NaHCO$_3$ (5 mL), dried over Na$_2$SO$_4$ and concentrated under vacuum to get a residue which was purified by silica gel flash column chromatography (EtOAc:Pet. Ether—19:1) to get the desired product as a crystalline solid (m.p. 142-145° C.), in good yields (103 mg, 77%). (TLC-$R_f$=0.25, EtOAc).

IR (NaCl, neat) ν: 3370, 3298, 3094, 2952, 2926, 1669, 1662, 1654, 1648, 1542, 1369, 1341, 1162, 1127 cm$^{-1}$. $^1$H NMR (300 MHz, CDCl$_3$) δ ppm: 8.15-8.11 (m, 1H), 7.75-7.66 (m, 3H), 6.09 (t, J=5.1 Hz, 1H), 4.59 (q, J=7.2 Hz, 1H), 4.03 (td, J=15.0, 7.5 Hz, 1H), 3.49 (dddd, J=14.4, 9.6, 4.8, 2.1

Hz, 1H), 3.44-3.37 (m, 1H), 3.26 (ddquint, J=9.9, 7.5, 2.1 Hz, 1H), 2.12 (dsext, J=7.5, 2.1 Hz, 1H), 1.96 (dddt, 14.4, 9.3, 4.8, 2.4 Hz, 1H), 1.42 (d, J=7.2 Hz, 3H). $^{13}$C NMR (75 MHz, CDCl$_3$) δ ppm: 174.8, 147.7, 133.9, 133.3, 132, 131.3, 124.4, 57.1, 43.2, 40.2, 29.6, 15.4. HRMS (EI) m/z calculated for $C_{12}H_{16}N_3O_5S$ [M+H]$^+$—314.0811, Found: 314.0821; calculated for $C_{12}H_{15}N_3NaO_5S$ [M+Na]$^+$—336.0630, Found: 336.0636 (100%).

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A compound of formula I

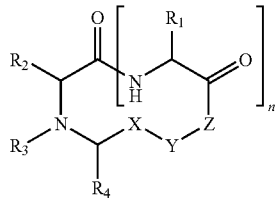

and stereoisomers, tautomers and pharmaceutically acceptable salts thereof, wherein
Z is —$NR_5$
X is —$CR_aR_b$—;
Y is —$CR_cR_d$—;
$R_a$, $R_c$, $R_b$, and $R_d$ are independently —H or a substituted or unsubstituted alkyl or aralkyl group;
$R_1$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, $R_1$ together with the carbon to which it is attached and the adjacent nitrogen, forms a substituted or unsubstituted pyrrolidine, oxazolidine, thiazolidine, imidazolidine, or piperidine ring;
$R_2$ is —H or a substituted or unsubstituted alkyl, cycloalkyl, cycloalkylalkyl, alkenyl, aryl, aralkyl, heterocyclyl, heterocyclylalkyl, heteroaryl or heteroaralkyl group; or $R_2$ and $R_3$ together with the atoms to which they are attached form a substituted or unsubstituted pyrrolidine, oxazolidine, thiazolidine, imidazolidine, or piperidine ring;
$R_3$ is —H, $PG_3$, or a substituted or unsubstituted alkyl, cycloalkyl, cycloalkylalkyl, alkenyl, aryl, aralkyl, heterocyclyl, heterocyclylalkyl, heteroaryl or heteroaralkyl group; wherein $PG_3$ is a protecting group; or $R_2$ and $R_3$ together with the atoms to which they are attached form a substituted or unsubstituted pyrrolidine, oxazolidine, thiazolidine, imidazolidine, or piperidine ring;
$R_4$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, or a $CHR_1$—NH—$R_6$ group;
$R_5$ is a —H, a substituted or unsubstituted alkyl, aryl, aralkyl, heteroaryl or a heteroaralkyl group, or a —NH—$CHR_1$—C(O)—$R_7$ group;
$R_6$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, C(O)$R_{10}$, —C(O)O$R_{10}$, —[C(O)—$CHR_1$—NH]$_m$—$R_{10}$, —[C(O)—$CHR_1$—NH]$_m$—C(O)$R_{10}$, or —[C(O)—$CHR_1$—NH]$_m$—C(O)$R_{10}$;
$R_7$ is a substituted or unsubstituted alkyl, cycloalkyl, cycloalkylalkyl, alkenyl, aryl, aralkyl, heterocyclyl, heterocyclylalkyl, heteroaryl or heteroaralkyl group, —O$R_{10}$, $NR_{10}R_{10}$, or —[NH—$CHR_{10}$—C(O)]$_m$—;
$R_{10}$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group;
m at each occurrence is independently an integer from 1 to 20; and
n is an integer from 1 to 20.

2. The compound of claim 1 wherein $R_a$ is a substituted or unsubstituted $C_{1-6}$ alkyl group, $R_c$ is a substituted or unsubstituted $C_{1-6}$ alkyl group, or both $R_a$ and $R_c$ are substituted or unsubstituted $C_{1-6}$ alkyl groups.

3. The compound of claim 1 wherein $R_b$ is —H, $R_d$ is —H, or both $R_b$ and $R_d$ are —H.

4. The compound of claim 1 wherein X is —$CH_2$—, Y is —$CH_2$—, or X and Y are —$CH_2$—.

5. The compound of claim 1 wherein $R_1$ at each occurrence and $R_2$ are independently —H, benzyl optionally substituted with one or more OH or halogen, imidazolylmethyl, indolylmethyl, or a $C_{1-6}$ alkyl group optionally substituted with one or more substituents selected from —F, —Cl, —Br, —I, —OH, —O-$PG_1$, —SH, —S-$PG_2$, —$NH_2$, —NH-$PG_3$, —C(O)OH, —C(O)O-$PG_4$, —C(O)$NH_2$, or —NHC(NH)$NH_2$; and wherein
$PG_1$ is a hydroxyl protecting group;
$PG_2$ is a thiol protecting group;
$PG_3$ is an amino protecting group; and
$PG_4$ is a carboxyl protecting group.

6. The compound of claim 1 wherein $R_1$ at each occurrence and $R_2$ are independently selected from the group consisting of —H, methyl, isopropyl, isobutyl, sec-butyl, hydroxymethyl, 1-hydroxyethyl, thiomethyl, 4-aminobutyl, 3-guanidinopropyl, benzyl, 4-hydroxybenzyl, indolylmethyl, methylthioethyl, carboxymethyl, carboxyethyl, carboxamidomethyl, carboxamidoethyl, and imidazolylmethyl.

7. The compound of claim 1 wherein $R_3$ is —H or $PG_3$.

8. The compound of claim 1 wherein $R_2$ and $R_3$ together form an unsubstituted pyrrolidine group.

9. The compound of claim 1 wherein $R_4$ is a —$CHR_1$—NH—$R_6$ group.

10. The compound of claim 9 wherein $R_6$ is —H, —C(O)$R_{10}$, —C(O)O$R_{10}$, —[C(O)—$CHR_1$—NH]$_m$—$R_{10}$, or —[C(O)—$CHR_1$—NH]$_m$—C(O)$R_{10}$.

11. The compound of claim 1 wherein $R_5$ is a —$CHR_1$—C(O)—$R_7$ group.

12. The compound of claim 11 wherein $R_7$ is —O$R_{10}$, —$NR_{10}R_{10}$, or —[NH—$CHR_1$—C(O)]$_m$—.

13. The compound of claim 1 wherein n is 1, 2, or 3.

14. A method of preparing a compound of claim 1 comprising cyclizing a compound of Formula III,

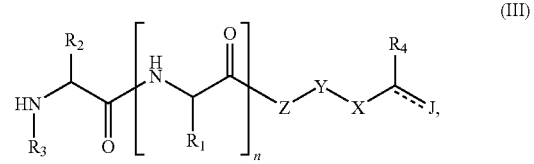

to produce the compound of Formula I,

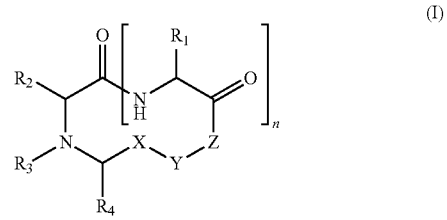

wherein
Z is $NR_5$;
X is —$CR_aR_b$—;
Y is —$CR_cR_d$—;

J is a leaving group or an oxo group, and the dashed line indicates a single or double bond to the leaving group or oxo group, respectively;

$R_a$, $R_c$, $R_b$, and $R_d$ are independently —H or a substituted or unsubstituted alkyl or aralkyl group;

$R_1$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, $R_1$ together with the carbon to which it is attached and the adjacent nitrogen, forms a substituted or unsubstituted pyrrolidine, oxazolidine, thiazolidine, imidazolidine, or piperidine ring;

$R_2$ is —H or a substituted or unsubstituted alkyl, cycloalkyl, cycloalkylalkyl, alkenyl, aryl, aralkyl, heterocyclyl, heterocyclylalkyl, heteroaryl or heteroaralkyl group; or $R_2$ and $R_3$ together with the atoms to which they are attached form a substituted or unsubstituted pyrrolidine, oxazolidine, thiazolidine, imidazolidine, or piperidine ring;

$R_3$ is —H, $PG_3$, or a substituted or unsubstituted alkyl, cycloalkyl, cycloalkylalkyl, alkenyl, aryl, aralkyl, heterocyclyl, heterocyclylalkyl, heteroaryl or heteroaralkyl group; wherein $PG_3$ is an amino protecting group; or $R_2$ and $R_3$ together with the atoms to which they are attached form a substituted or unsubstituted pyrrolidine, oxazolidine, thiazolidine, imidazolidine, or piperidine ring;

$R_4$ is a substituted or unsubstituted alkyl, cycloalkyl, cycloalkylalkyl, alkenyl, aryl, aralkyl, heterocyclyl, heterocyclylalkyl, heteroaryl or heteroaralkyl group, or a —$CHR_1$—NH—$R_6$ group;

$R_5$ is a —H, a substituted or unsubstituted alkyl, aryl, aralkyl, heteroaryl or a heteroaralkyl group, or a —$CHR_1$—C(O)—$R_7$ group;

$R_6$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —C(O)$R_{10}$, —C(O)O$R_{10}$, —[C(O)—$CHR_1$—NH]$_m$—$R_{10}$, —[C(O)—$CHR_1$—NH]$_m$—C(O)$R_{10}$, or —[C(O)—$CHR_1$—NH]$_m$—C(O)—O$R_{10}$;

$R_7$ is a substituted or unsubstituted alkyl, cycloalkyl, cycloalkylalkyl, alkenyl, aryl, aralkyl, heterocyclyl, heterocyclylalkyl, heteroaryl or heteroaralkyl group, —O$R_{10}$, —N$R_{10}R_{10}$, or —[NH—$CHR_1$—C(O)]$_m$—;

$R_{10}$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group;

m is an integer from 1 to 20; and n is an integer from 1 to 20.

15. The method of claim 14 wherein the compound of Formula III is selected from a compound of Formula IIIA, a compound of Formula IIIB, or a compound of Formula IIIC,

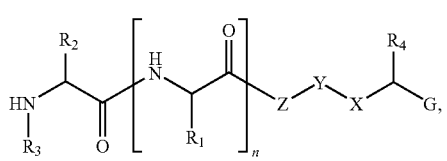
(IIIA)

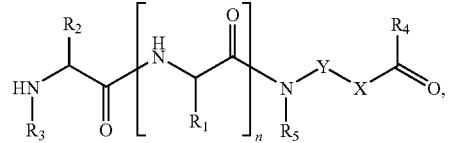
(IIIB)

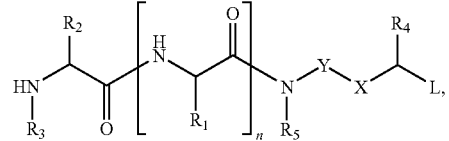
(IIIC)

wherein G is a halogen and L is a leaving group.

16. The method of claim 15 further comprising coupling a compound of Formula IV

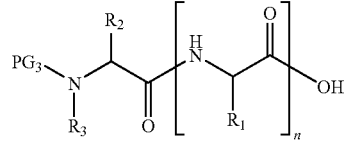
(IV)

with a compound of Formula VA or VB,

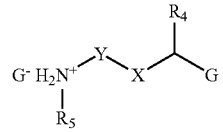
(VA)

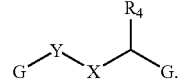
(VB)

and removing the amino-protecting group $PG_3$ to provide the compound of Formula IIIA.

17. A method of making a compound of claim 1 comprising cyclizing a compound of Formula IX,

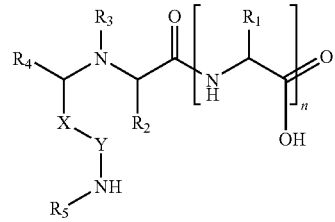
(IX)

to produce a compound of Formula I,

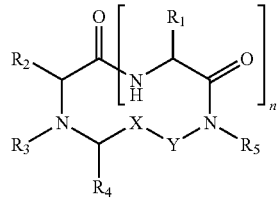
(I)

wherein

X is —$CR_aR_b$—;

Y is —$CR_cR_d$—;

$R_a$, $R_c$, $R_b$, and $R_d$ are independently —H or a substituted or unsubstituted alkyl or aralkyl group;

$R_1$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, $R_1$ together with the carbon to which it is attached and the adjacent nitrogen, forms a substituted or unsubstituted pyrrolidine, oxazolidine, thiazolidine, imidazolidine, or piperidine ring;

$R_2$ is —H or a substituted or unsubstituted alkyl, cycloalkyl, cycloalkylalkyl, alkenyl, aryl, aralkyl, heterocyclyl, heterocyclylalkyl, heteroaryl or heteroaralkyl group; or $R_2$ and $R_3$ together with the atoms to which they are attached form a substituted or unsubstituted pyrrolidine, oxazolidine, thiazolidine, imidazolidine, or piperidine ring;

$R_3$ is —H, —$PG_3$, or a substituted or unsubstituted alkyl, cycloalkyl, cycloalkylalkyl, alkenyl, aryl, aralkyl, heterocyclyl, heterocyclylalkyl, heteroaryl or heteroaralkyl group; wherein $PG_3$ is an amino protecting group; or $R_2$ and $R_3$ together with the atoms to which they are attached form a substituted or unsubstituted pyrrolidine, oxazolidine, thiazolidine, imidazolidine, or piperidine ring;

$R_4$ is a substituted or unsubstituted alkyl, cycloalkyl, cycloalkylalkyl, alkenyl, aryl, aralkyl, heterocyclyl, heterocyclylalkyl, heteroaryl or heteroaralkyl group, or a —$CHR_1$—NH—$R_6$ group;

$R_5$ is a —H, a substituted or unsubstituted alkyl, aryl, aralkyl, heteroaryl or a heteroaralkyl group, or a —$CHR_1$—C(O)—$R_7$ group;

$R_6$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —$C(O)R_{10}$, —$C(O)OR_{10}$, —[C(O)—$CHR_1$—NH]$_m$—$R_{10}$, —[C(O)—$CHR_1$—NH]$_m$—$C(O)R_{10}$, or —[C(O)—$CHR_1$—NH]$_m$—C(O)—$OR_{10}$;

$R_7$ is a substituted or unsubstituted alkyl, cycloalkyl, cycloalkylalkyl, alkenyl, aryl, aralkyl, heterocyclyl, heterocyclylalkyl, heteroaryl or heteroaralkyl group, —$OR_{10}$, —$NR_{10}R_{10}$, or —[NH—$CHR_1$—C(O)]$_m$—;

$R_{10}$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group;

m is an integer from 1 to 20; and n is an integer from 1 to 20.

18. A compound of formula I

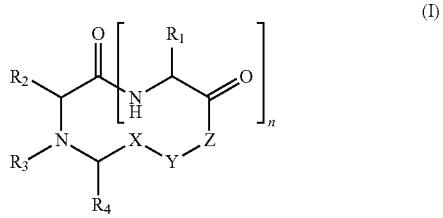

(I)

and stereoisomers, tautomers and pharmaceutically acceptable salts thereof, wherein Z is O or —$NR_5$ X is —$CR_aR_b$—;

Y is —$CR_cR_d$;

$R_a$, $R_b$, $R_c$, and $R_d$ are independently —H or a substituted or unsubstituted alkyl or aralkyl group;

$R_1$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, $R_1$ together with the carbon to which it is attached and the adjacent nitrogen, forms a substituted or unsubstituted pyrrolidine, oxazolidine, thiazolidine, imidazolidine, or piperidine ring;

$R_2$ is —H or a substituted or unsubstituted alkyl, cycloalkyl, cycloalkylalkyl, alkenyl, aryl, aralkyl, heterocyclyl, heterocyclylalkyl, heteroaryl or heteroaralkyl group; or $R_2$ and $R_3$ together with the atoms to which they are attached form a substituted or unsubstituted pyrrolidine, oxazolidine, thiazolidine, imidazolidine, or piperidine ring;

$R_3$ is —H, $PG_3$, or a substituted or unsubstituted alkyl, cycloalkyl, cycloalkylalkyl, alkenyl, aryl, aralkyl, heterocyclyl, heterocyclylalkyl, heteroaryl or heteroaralkyl group; wherein $PG_3$ is a protecting group; or $R_2$ and $R_3$ together with the atoms to which they are attached form a substituted or unsubstituted pyrrolidine, oxazolidine, thiazolidine, imidazolidine, or piperidine ring;

$R_4$ is —H $R_5$ is a —H, a substituted or unsubstituted alkyl, aryl, aralkyl, heteroaryl or a heteroaralkyl group, or a —NH—$CHR_1$—C(O)—$R_7$ group;

$R_6$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, $C(O)R_{10}$, —$C(O)OR_{10}$, —[C(O)—$CHR_1$—NH]$_m$—$R_{10}$, —[C(O)—$CHR_1$—NH]$_m$—$C(O)R_{10}$, or —[C(O)—$CHR_1$—NH]$_m$—$C(O)R_{10}$;

$R_7$ is a substituted or unsubstituted alkyl, cycloalkyl, cycloalkylalkyl, alkenyl, aryl, aralkyl, heterocyclyl, heterocyclylalkyl, heteroaryl or heteroaralkyl group, —$OR_{10}$, $NR_{10}R_{10}$, or —[NH—$CHR_{10}$—C(O)]$_m$—;

$R_{10}$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group;

m at each occurrence is independently an integer from 1 to 20; and n is an integer from 1 to 20.

19. The compound of claim 18 wherein Z is —$NR_5$ and $R_5$ is —H.

20. The composition of claim 18 wherein the compounds is

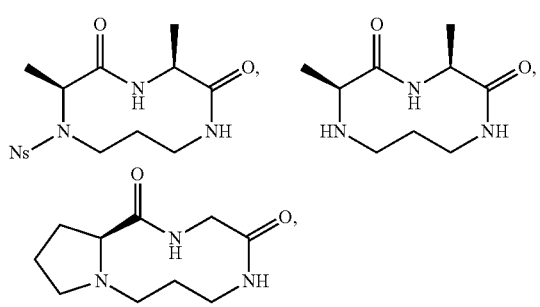

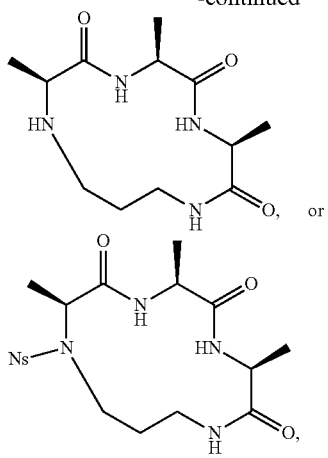
or stereoisomers, tautomers, or pharmaceutically acceptable salts thereof.
* * * * *

UNITED STATES PATENT AND TRADEMARK OFFICE
CERTIFICATE OF CORRECTION

PATENT NO.        : 8,835,602 B2
APPLICATION NO.   : 12/550977
DATED             : September 16, 2014
INVENTOR(S)       : Prabhakaran It is certified that error appears in the above-identified patent and that said Letters Patent is hereby corrected as shown below:

On the Title Page, Item (56), under "OTHER PUBLICATIONS", in Column 2, Line 17, delete "y-Turns" and insert -- γ-Turns --, therefor.

On Title Page 2, Item (56), under "OTHER PUBLICATIONS", in Column 1, Line 13, delete "337-343" and insert -- 337-343. --, therefor.

On Title Page 2, Item (56), under "OTHER PUBLICATIONS", in Column 2, Line 50, delete "rececptor" and insert -- receptor --, therefor.

On Title Page 3, Item (56), under "OTHER PUBLICATIONS", in Column 1, Line 2, delete "α-Strands$^a$,"" and insert -- β-Strands$^a$," --, therefor.

On Title Page 3, Item (56), under "OTHER PUBLICATIONS", in Column 1, Line 5, delete "α-strands,"" and insert -- β-strands," --, therefor.

On Title Page 3, Item (56), under "OTHER PUBLICATIONS", in Column 1, Line 63, delete "et al., et al.," and insert -- et al., --, therefor.

On Title Page 3, Item (56), under "OTHER PUBLICATIONS", in Column 2, Lines 54-56, delete "Lehmler, H. et al., "Synthesis and structure of environmentally relevant perfluorinated sulfonamides," Journal of Fluorine Chemistry, 128:595-607 (2007).".

On Title Page 4, Item (56), under "OTHER PUBLICATIONS", in Column 1, Line 8, delete "anti-y-N-" and insert -- anti-γ-N- --, therefor.

In the Specification

In Column 1, below Title, insert -- CROSS REFERENCE TO RELATED APPLICATIONS

Signed and Sealed this
Seventh Day of April, 2015

Michelle K. Lee
*Director of the United States Patent and Trademark Office*

CERTIFICATE OF CORRECTION (continued)

The present application claims priority to a corresponding patent application filed in India and having application number 505/CHE/2009, filed on Mar. 6, 2009, the entire contents of which are herein incorporated by reference. --.

In Column 7, Line 36, delete "methythiomethyl" and insert -- methylthiomethyl --, therefor.

In Column 7, Line 51, delete "4-nitrobenzenesulonyl," and insert -- 4-nitrobenzenesulfonyl, --, therefor.

In Column 10, Line 6, delete "$R_a$, $R_c$, $R_b$," and insert -- $R_a$, $R_b$, $R_c$, --, therefor.

In Column 18, Line 4, delete "$R_a$, $R_c$, $R_b$," and insert -- $R_a$, $R_b$, $R_c$, --, therefor.

In Column 20, Line 65, delete "PPh3," and insert -- $PPh_3$, --, therefor.

In Column 21, Lines 4-5, delete "  ", therefor.

In Column 25, Line 2, delete "1687-1689;" and insert -- 1687-1689. --, therefor.

In Column 25, Line 10, delete "a of" and insert -- of --, therefor.

In Column 26, Line 35, delete "meletin," and insert -- melittin, --, therefor.

In Column 26, Lines 49-50, delete "permeablization." and insert -- permeabilization. --, therefor.

In Columns 29 & 30, in Table 1, under "Target Domain/Cell", Line 6, delete "preforation" and insert -- perforation --, therefor.

In Columns 29 & 30, in Table 1, under "Therapeutic target", Line 4, delete "permeablization" and insert -- permeabilization --, therefor.

In Columns 31 & 32, in Table 1, under "Peptide", Line 2, delete "Gramidicin-S" and insert -- Gramicidin-S --, therefor.

In Columns 31 & 32, in Table 1, under "Peptide", Line 4, delete "Circumsporozite" and insert -- Circumsporozoite --, therefor.

In Column 40, Line 2, delete "Gel1)" and insert -- Gel) --, therefor.

In Column 42, Line 32, delete "Gel1)" and insert -- Gel) --, therefor.

In Column 43, Line 7, delete "below" and insert -- below. --, therefor.

In Column 46, Line 24, delete "D2O)" and insert -- $D_2O$) --, therefor.

In Column 51, Line 20, delete "cintered" and insert -- sintered --, therefor.

In Column 51, Line 23, delete "silical" and insert -- silica --, therefor.

In Column 54, Line 28, delete "a oil," and insert -- an oil, --, therefor.

In Column 56, Line 8, delete "15.0," and insert -- 3.43 (dt, J=15.0, --, therefor.

In the Claims

In Column 75, Line 21, in Claim 1, delete "$R_a$, $R_c$, $R_b$," and insert -- $R_a$, $R_b$, $R_c$, --, therefor.

In Column 77, Line 4, in Claim 14, delete "$R_a$, $R_c$, $R_b$," and insert -- $R_a$, $R_b$, $R_c$, --, therefor.

In Column 78, Line 37, in Claim 16, after Equation "(VB)", delete ".".

In Column 78, Line 66, in Claim 17, delete "$R_a$, $R_c$, $R_b$," and insert -- $R_a$, $R_b$, $R_c$, --, therefor.

In Column 79, Lines 41-42, in Claim 17, delete "[NH—$CHR_1$—C(O)]—$_m$—;" and insert -- —[NH—$CHR_1$—C(O]$_m$—; --, therefor.

In Column 80, Line 1, in Claim 18, delete "Rd" and insert -- $R_d$ --, therefor.

In Column 80, Line 26, in Claim 18, delete "—H" and insert -- —H; --, therefor.

In Column 80, Line 52, in Claim 20, delete "composition" and insert -- compound --, therefor.